US009974844B2

(12) United States Patent
Myc et al.

(10) Patent No.: US 9,974,844 B2
(45) Date of Patent: May 22, 2018

(54) CANCER VACCINE COMPOSITIONS AND METHODS OF USING THE SAME

(75) Inventors: Andrzej Myc, Ann Arbor, MI (US); Ilona Kryczek, Ann Arbor, MI (US); James R. Baker, Jr., Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1080 days.

(21) Appl. No.: 13/129,795

(22) PCT Filed: Nov. 17, 2009

(86) PCT No.: PCT/US2009/064822
§ 371 (c)(1),
(2), (4) Date: Jul. 29, 2011

(87) PCT Pub. No.: WO2010/057197
PCT Pub. Date: May 20, 2010

(65) Prior Publication Data
US 2011/0280911 A1 Nov. 17, 2011

Related U.S. Application Data

(60) Provisional application No. 61/115,421, filed on Nov. 17, 2008.

(51) Int. Cl.
A61K 39/00 (2006.01)
A61P 37/04 (2006.01)
A61P 35/00 (2006.01)
A61K 9/00 (2006.01)
A61K 9/107 (2006.01)
A61K 31/00 (2006.01)
A61K 31/7088 (2006.01)
A61K 39/39 (2006.01)
A61P 35/04 (2006.01)

(52) U.S. Cl.
CPC ........ *A61K 39/0011* (2013.01); *A61K 9/0043* (2013.01); *A61K 9/1075* (2013.01); *A61K 31/00* (2013.01); *A61K 31/7088* (2013.01); *A61K 39/39* (2013.01); *A61K 2039/5152* (2013.01); *A61K 2039/543* (2013.01); *A61K 2039/55566* (2013.01)

(58) Field of Classification Search
None
See application file for complete search history.

(56) References Cited

U.S. PATENT DOCUMENTS

| | | |
|---|---|---|
| 3,854,480 A | 12/1974 | Zaffaroni |
| 3,864,472 A | 2/1975 | Pensak et al. |
| 3,912,666 A | 10/1975 | Spitzer et al. |
| 3,968,250 A | 7/1976 | Boucher |
| 4,020,183 A | 4/1977 | Asculai et al. |
| 4,262,007 A | 4/1981 | Sherrill |
| 4,350,707 A | 9/1982 | Keith et al. |
| 4,451,267 A | 5/1984 | Schwab et al. |
| 4,452,775 A | 6/1984 | Kent |
| 4,596,556 A | 6/1986 | Morrow et al. |
| 4,596,792 A | 6/1986 | Vyas |
| 4,599,088 A | 7/1986 | Davis et al. |
| 4,599,230 A | 7/1986 | Milich et al. |
| 4,599,231 A | 7/1986 | Milich et al. |
| 4,601,903 A | 7/1986 | Frasch |
| 4,675,189 A | 6/1987 | Kent et al. |
| 4,790,824 A | 12/1988 | Morrow et al. |
| 4,886,670 A | 12/1989 | Horrobin |
| 4,895,452 A | 1/1990 | Yiournas et al. |
| 4,935,439 A | 6/1990 | Kashman et al. |
| 4,940,460 A | 7/1990 | James et al. |
| 4,941,880 A | 7/1990 | Burns |
| 5,064,413 A | 11/1991 | McKinnon et al. |
| 5,073,372 A | 12/1991 | Turner et al. |
| 5,075,109 A | 12/1991 | Tice et al. |
| 5,103,497 A | 4/1992 | Hicks |
| 5,108,660 A | 4/1992 | Michael |
| 5,112,844 A | 5/1992 | Paradies |
| 5,118,808 A | 6/1992 | Paradies |
| 5,133,974 A | 7/1992 | Paradissis et al. |

(Continued)

FOREIGN PATENT DOCUMENTS

| | | |
|---|---|---|
| CN | 1159158 A | 9/1997 |
| CN | 1647821 | 8/2005 |

(Continued)

OTHER PUBLICATIONS

Vyas and Gupta (Expert Review of Vaccines, 2007, vol. 6, pp. 401-408).*
Larregina and Falo (Human Gene Therapy, 2000, vol. 11, pp. 2301-2305).*
Thorbecke and Keuning (Journal of Immunology, 1953, vol. 70, pp. 129-134).*
The abstract of Sun (Chinese Journal of Cellular and Molecular Immunology, 2005, vol. 21, pp. 69-71).*
Bielinska et al (AIDS Research and Human Retroviruses, 2008, vol. 24, pp. 271-281).*
Marshall et al (Cancer Immunology Immunotherapy, 2005, vol. 54, pp. 1082-1094).*
Wheeler (Salud p'ublica de M'exico, (1997, vol. 39, pp. 283-287).*
Bielinska et al (Infection and Immunity, 2007, vol. 75. pp. 4020-4029).*

(Continued)

*Primary Examiner* — Karen A. Canella
(74) *Attorney, Agent, or Firm* — Casimir Jones S.C.; Tyler J. Sisk

(57) ABSTRACT

The present invention provides methods and compositions for the stimulation of immune responses. In particular, the present invention provides nanoemulsion compositions and methods of using the same for the induction of immune responses (e.g., innate and adaptive immune responses (e.g., for generation of host immunity against an environmental pathogen)). Compositions and methods of the present invention find use in, among other things, clinical (e.g. therapeutic and preventative medicine (e.g., vaccination)) and research applications.

10 Claims, 22 Drawing Sheets

(56) References Cited

U.S. PATENT DOCUMENTS

| | | |
|---|---|---|
| 5,188,822 A | 2/1993 | Viccaro et al. |
| 5,284,656 A | 2/1994 | Platz et al. |
| 5,312,335 A | 5/1994 | McKinnon et al. |
| 5,334,144 A | 8/1994 | Alchas et al. |
| 5,339,163 A | 8/1994 | Homma et al. |
| 5,366,983 A | 11/1994 | Lattin et al. |
| 5,368,837 A | 11/1994 | Baker et al. |
| 5,380,530 A | 1/1995 | Hill |
| 5,383,851 A | 1/1995 | McKinnon et al. |
| 5,405,602 A | 4/1995 | Simmons et al. |
| 5,405,604 A | 4/1995 | Hall |
| 5,407,686 A | 4/1995 | Patel et al. |
| 5,451,569 A | 9/1995 | Wong et al. |
| 5,466,220 A | 11/1995 | Brenneman |
| 5,480,381 A | 1/1996 | Weston |
| 5,503,627 A | 4/1996 | McKinnon et al. |
| 5,510,104 A | 4/1996 | Allen |
| 5,520,639 A | 5/1996 | Peterson et al. |
| 5,536,502 A | 7/1996 | Mulder |
| 5,547,677 A | 8/1996 | Wright |
| 5,549,901 A | 8/1996 | Wright |
| 5,569,189 A | 10/1996 | Parsons |
| 5,576,016 A | 11/1996 | Amselem et al. |
| 5,599,302 A | 2/1997 | Lilley et al. |
| 5,618,840 A | 4/1997 | Wright |
| 5,649,912 A | 7/1997 | Peterson |
| 5,651,959 A | 7/1997 | Hill et al. |
| 5,656,280 A | 8/1997 | Herb et al. |
| 5,662,932 A | 9/1997 | Amselem et al. |
| 5,662,957 A | 9/1997 | Wright |
| 5,698,219 A | 12/1997 | Valdivia et al. |
| 5,700,679 A | 12/1997 | Wright |
| 5,704,911 A | 1/1998 | Parsons |
| 5,709,879 A | 1/1998 | Barchfield et al. |
| 5,716,637 A | 2/1998 | Anselem et al. |
| 5,736,152 A | 4/1998 | Dunn |
| 5,855,872 A | 1/1999 | Libin |
| 5,893,397 A | 4/1999 | Peterson et al. |
| 5,985,309 A | 11/1999 | Edwards et al. |
| 5,993,412 A | 11/1999 | Deily et al. |
| 5,997,848 A | 12/1999 | Patton et al. |
| 6,015,832 A | 1/2000 | Baker, Jr. et al. |
| 6,051,256 A | 4/2000 | Platz et al. |
| RE37,053 E | 2/2001 | Hanes et al. |
| 6,294,204 B1 | 9/2001 | Rossling et al. |
| 6,423,344 B1 | 7/2002 | Platz et al. |
| 6,436,443 B2 | 8/2002 | Edwards et al. |
| 6,447,753 B2 | 9/2002 | Edwards et al. |
| 6,503,480 B1 | 1/2003 | Edwards et al. |
| 6,506,803 B1 | 1/2003 | Baker, Jr. et al. |
| 6,518,239 B1 | 2/2003 | Kuo et al. |
| 6,559,189 B2 | 5/2003 | Baker, Jr. et al. |
| 6,592,883 B1 | 7/2003 | Gers-Barlag et al. |
| 6,592,904 B2 | 7/2003 | Platz et al. |
| 6,635,283 B2 | 10/2003 | Edwards et al. |
| 6,635,676 B2 | 10/2003 | Baker, Jr. et al. |
| 6,651,655 B1 | 11/2003 | Licalsi et al. |
| 7,402,317 B2 | 7/2008 | Bystryn |
| 2002/0045667 A1 | 4/2002 | Baker, Jr. et al. |
| 2002/0155084 A1 | 10/2002 | Roessler et al. |
| 2002/0187154 A1* | 12/2002 | Rappuoli .................... 424/184.1 |
| 2003/0194412 A1 | 10/2003 | Baker, Jr. et al. |
| 2004/0043041 A1 | 3/2004 | Baker, Jr. et al. |
| 2005/0281843 A1 | 12/2005 | Singh et al. |
| 2006/0286115 A1 | 12/2006 | Agadjanyan et al. |
| 2007/0191386 A1* | 8/2007 | Fancelli .............. C07D 471/04 514/252.06 |
| 2009/0291095 A1* | 11/2009 | Baker, Jr. ............... A61K 39/07 424/184.1 |

FOREIGN PATENT DOCUMENTS

| | | |
|---|---|---|
| EP | 0517565 | 12/1992 |
| EP | 0832649 A1 | 4/1998 |
| EP | 0278996 A1 | 8/1998 |
| EP | 1092444 | 4/2001 |
| EP | 1655021 A1 | 5/2006 |
| GB | 1321579 A | 6/1973 |
| GB | 2220211 | 1/1990 |
| JP | S63-221835 | 9/1988 |
| JP | H05-124910 | 5/1993 |
| JP | H06-279268 | 10/1994 |
| JP | A Hei 7-67893 | 3/1995 |
| JP | H07-102294 | 4/1995 |
| JP | H10-87428 | 4/1997 |
| JP | 2001-549664 | 12/2000 |
| WO | WO 91/13909 | 9/1991 |
| WO | WO 91/14439 | 10/1991 |
| WO | WO 94/00153 | 1/1994 |
| WO | WO 94/21292 | 9/1994 |
| WO | WO 94/26252 A1 | 11/1994 |
| WO | WO 94/28120 | 12/1994 |
| WO | WO 95/17210 | 6/1995 |
| WO | WO 95/31966 | 10/1995 |
| WO | WO 95/31956 | 11/1995 |
| WO | WO 96/02555 | 2/1996 |
| WO | WO 96/23409 A1 | 8/1996 |
| WO | WO 96/33725 | 10/1996 |
| WO | WO 96/33739 | 10/1996 |
| WO | WO 96/40144 | 12/1996 |
| WO | WO 97/11957 | 4/1997 |
| WO | WO 97/13537 | 4/1997 |
| WO | WO 97/37705 | 10/1997 |
| WO | WO 97/48440 | 12/1997 |
| WO | WO 98/20734 | 5/1998 |
| WO | WO 98/28037 | 7/1998 |
| WO | WO 98/29090 | 7/1998 |
| WO | WO 99/27961 | 6/1999 |
| WO | WO 99/34850 | 6/1999 |
| WO | WO 00/028821 | 5/2000 |
| WO | WO00/33869 | * 6/2000 |
| WO | WO 00/53155 | 9/2000 |
| WO | WO 01/13977 | 3/2001 |
| WO | WO02/30434 | * 4/2002 |
| WO | WO2007/118660 | * 10/2007 |
| WO | WO2007/120860 | * 10/2007 |
| WO | WO2008/147482 | * 12/2008 |

OTHER PUBLICATIONS

Adjei, et al., Bioavailability of leuprolide following intratracheal administration to beagle dogs, Int. J. Pharmaceutics 1990; 63:135-144.

Adjei, et al., Pulmonary delivery of peptide drugs: effect of particle size on bioavailability of leuprolide acetate in healthy male volunteers, Pharm Res. Jun. 1990;7(6):565-9.

Alasri et al., "Sporicidal properties of peracetic acid and hydrogen peroxide, alone and in combination, in comparison with chlorine and formaldehyde for ultrafiltration membrane disinfection." 1993 Can. J. Microbiol 39: 52-60.

Anichini et al., Melanoma cells and normal melanocytes share antigens recognized by HLA-A2-restricted cytotoxic T cell clones from melanoma patients, J Exp Med. Apr. 1, 1993;177(4):989-98.

Baragi et al., "Transplantation of transdiced Chondrocytes protects articular cartilage from intedeukin 1-induced extracellular matrix degradation." 1995 J Clin Invest 96: 2454-2460.

Barrett and Inglis "Growth purification and titration of influenza viruses." In: Mahy WJ. ed. Virology. a Practical approach. IRL. Press, 1985; 119•151. This reference is a book and is not being submitted at this time but if the Examiner requests the reference it will be submitted.

Beauchamp et al., "A Critical review of the toxicology of glutaraldphyde." 1992 Crit. Rev. ToxicoL 22:143-174.

Berkelman et al., "Emerging infectious diseases in the United States, 1993." 1994 J Infect Dis. 170(2):272-7.

Braquet, et al., Effect of endothelin-1 on blood pressure and bronchopulmonary system of the guinea pig, J Cardiovasc Pharmacol. 1989;13 Suppl 5:S143-6; discussion S150.

Burdon and Wende "On the differentiation of anthrax bacilli from Bacillus cereus." 1960 J. Infect. Dis. 107: 224-234.

(56) References Cited

OTHER PUBLICATIONS

Burdon et al., "Experimental infection of mice with Bacillus cereus: studies of pathogenesis and pathologic changes." 1967 J. Infect. Dis. 117:307-316.

Chatlyyne et al., "A lipid emulsion with effective virucidal activity against H IV-I and other common viruses." Foundation for Retrovirology and Human Health, 3rd Conference on Retroviruses and Opportunistic Infections, Washington D.C., U.S.A., 1996; Abstract#351. This reference is a book and is not being submitted at this time but if the Examiner requests the reference it will be submitted.

Corbett et al., Tumor induction relationships in development of transplantable cancers of the colon in mice for chemotherapy assays, with a note on carcinogen structure, Cancer Res. Sep. 1975;35(9):2434-9.

Dalgleish, Cancer vaccines, Br J Cancer. May 2000;82(10):1619-24.

Dobson et al. "Herpes simplex virus type 1 and Alzheimer,s disease," in Neurobiology of Aging 20 (1999) 457-465.

Dragon and Rennie "The ecology and anthrax spores: Tough but not invincible." 1995 Can. Vet. J. 36: 295-301.

Drobniewski "Bacillus cereus and related species." 1993 Clin. Microbiol. Rev. 6: 324-338.

Eriksson et al., "Virus validation of plasma-derived products produced by Pharmacia, with particular reference to immuno Globulins." Blood Coagulation and Fibtinolysis 1994; 5 (Suppl. 3): S37-S44.

Falo et al., Targeting antigen into the phagocytic pathway in vivo induces protective tumour immunity, Nat Med 1995, 1(7):649-653.

Florence "Non-ionic surfactant vesicles: preparation and characterization." In: Gregoriadis G. ed. Liposome Technology. Liposome Preparations and Related Techniques. 2nd cd. vol. I. CRC Press, 1993. This reference is a book and is not being submitted at this time but if the Examiner requests the reference it will be submitted.

Foster and Johnstone "Pulling the trigger: the mechanism of bacterial spore germination." 1990 MolecularMicrobiology 4:137-141.

Franz et al., "Clinical recognition and management of patients exposed to biological warfare agents." JAMA 1997; 278: 399-411.

Fritz et al., "Pathology of experimental anthrax in'the rhesus monkey." 1995 Lab. Invest. 73: 691-702.

Ge et al: "MAGE-1/Heat shock protein 70/MAGE-3 fusion protein vaccine in nanoemulsion enhances cellular and humoral immune responses to MAGE-1 or MAGE-3 in vivo", Cancer Immunology, Immunotherapy, Springer, Berlin, DE, vol. 55, No. 7, Jul. 1, 2006 (Jul. 1, 2006), pp. 841-849, XP019333259, ISSN: 1432-0851, DOI: 10.1007/S00262-005-0073-Y http://dx.doi.org/10.1007/s00262-005-0073-y.

Ge et al: "The antitumor immune responses induced by nanoemulsion-encapsulated MAGE1-HSP70/SEA complex protein vaccine following peroral administration route", Cancer Immunology, Immunotherapy, Springer, Berlin, DE, vol. 58, No. 2, Jun. 4, 2008 (Jun. 4, 2008), pp. 201-208, XP019654580, ISSN: 1432-0851.

Goodman's & Gilman's "The Pharmacological Basis of Therapeutics" Eds. Hardman et 01., 9th Edition, Pubi. McGraw Hill, 1996; chapters 43 through 50. This reference is a book and is not being submitted at this time but if the Examiner requests the reference it will be submitted.

Graham et al., "Characteristics of a human cell line transformed by DNA from human adenovirus type 5." 1977 J Gen Virol 36: 59-74.

Halvorson and Church, Biochemistry of Spores of Aerobic Bacilli with Special Reference to Germination, Bacteriol Rev 1957, 21:112.

Hamouda et al., "A novel surfactant nanoemulsion with broad-spectrum sporicidal activity against *Bacillus* species" 1999 Journal Infectious Disease 180:1939-1949.

Hamouda et al., "Microbicidal Effects of Lipsome-Like Nanoemulsion on Pathogenic Gram Negative Bacteria" 98th ASM General Meeting, Atlanta, Abstract # A-52 p. 47, American Society for Microbiology, 1998.

Hayden et al., "Plaque inhibition assay for drug susceptibility testing of influenza viruses." Antimicrob Agents Chemother. 1980 17: 865-870.

Henrickson "Viral Pneumonia in Children" 1998 Seminars in Pediatric Infectious Disease vol. 9 No. 3 pp. 217-233.

Herlocher et al., "Sequence comparison of AIAA/6/60 influenza viruses: mutations, which may contribute to attenuation." Virus Res. 1996; 42:11-25.

Hermonat et al., "The spermicide nonoxynol-9 does not inactivate papillomavirus." Sexually Trans Dis 1992; 19: 203-205.

Hess et al., "Epidermal toxicity of disinfectants." Amer. J. Dent. 1991; 4: 51-56.

Hills, Chemical Factors in the Germination of Spore-bearing Aerobes: Observations on the Influence of Species, Strain and Conditions of Growth, 1950, J Gen Microbiol 4:38.

Horowitz et al., "Solvent/detergent-treated plasma: a vi rus-in activated substitute for fresh frozen plasma" 1992 Blood 79: 826-831.

Huang et al., "Antiviral activity of some natural and synthetic sugar analogues." 1991 FEBS Letters. 291: 199-202.

Hubbard, et al., Anti-neutrophil-elastase defenses of the lower respiratory tract in alpha 1-antitrypsin deficiency directly augmented with an aerosol of alpha 1-antitrypsin, (1989) Annals of Internal Medicine, vol. III, pp. 206-212.

Ilium et al., Hyaluronic acid ester microspheres as a nasal delivery system for insulin, J. Controlled Rel., 1994, 29:133-141.

Itoh, K. et al., Interleukin 2 activation of cytotoxic T-lymphocytes infiltrating into human metastatic melanomas, (1986), Cancer Res. 46:3011-3017.

Ivins et al., "Experimental anthrax vaccines: efficacy of adjuvants combined with protective antigen against an aerosol Bacillus anthracis spore challenge in guinea pigs." 1995 Vaccine 13: 1779-1784.

Jackson et al., "PCR analysis of tissue samples from the 1979 Sverdlovsk anthrax victims: The presence of multiple Bacillus anthracis strains in 10 different victims." PNAS 1998; 95:1224-1229.

Karaivanova and Spiro "Sulphation of N-linked oligosacchaddes of vesicular stomatitis and influenza virus envelope glycoproteins: host cell specificity, subcellular localization and identification of substituted saccharides." Bioch J 1998; 329: 511-518.

Kawakami et al, T-cell recognition of human melanoma antigens, (1993) J. Immunother. 14:88-93.

Kawakami et al., Shared human melanoma antigens. Recognition by tumor-infiltrating lymphocytes in HLA-A2.1-transfected melanomas, (1992) J. Immunol. 148:638-643.

Lamanna and Jones "Lethality for mice of vegetative and spore forms of Bacillus cereus and Bacillus cereus-like insect pathogens injected intraperitoneally and subcutaneously." J. Bact. 1963; 85: 532-535.

Lamb and Krug "Orthomyxoviride: The viruses and their replication." In: Fields BN. Knipe DM. Howley PM. eds. Fields Virology, 3rd ed., Philadelphia Pennsylvania, U.S.A., Lippincoft-Raven Publishers, 1996; 1353-1395.

Lambert et al., TCR vaccines against a murine T cell lymphoma: a primary role for antibodies of the IgG2c class in tumor protection, J Immunol 2004, 172(2):929-936.

Lee "Review: in vitro spermicidal tests." Contraception 1996; 54: 131-147.

Lim and Chae "A simple assay for DNA transfection by incubation of the cells in culture dishes with substrates for beta-galactosidase." 1989 Biotechniques 7: 576-579.

Lin et al: "Immunization of C58 Mice to Line Ib Leukemia", Cancer Research, vol. 29, Jan. 1, 1969 (Jan. 1, 1969), pp. 2157-2162, XP055079628.

Lineaweaver et al., "Topical antimicrobial toxicity." Arch. Surg. 1985; 120: 267-270.

Maha and Igarashi "The effect of nonionic detergent on dengue and Japanese encephalitis virus antigens in antigen detection ELISA and IgM-capture ELISA." Southeast Asian J Trop Med Pub Health 1997; 28: 718-722.

(56) References Cited

OTHER PUBLICATIONS

Mammen et al., "Effective inhibitors of hemagglutination by influenza virus synthesized from polymers having active ester groups. Insight into mechanism of inhibition." 1995 J Med Chem 38: 4179-4190.
Martin, Remington's Pharmaceutical Sciences, 15th Ed., Mack Publ. Co., Easton, Pa. (1975).
Mascola, Herpes Simplex Virus Vaccines—Why Don't Antibodies Protect?, JAMA, vol. 282, No. 4, pp. 379-380, 1999.
Mendel et al., "Oral administration of a prodrug of the influenza virus neuraminidase inhibitor GS 4071 protects mice and ferrets against influenza infection" 1998 Antimicrob Agents Chemother 42: 640-646.
Meselson et al., "The Sverdlovsk anthrax outbreak of 1979." Science 1994; 266:1202-1208.
Mestecky, The common mucosal immune system and current strategies for induction of immune responses in external secretions, Journal of Clinical Immunology, 7:265-276, 1987.
Mobley "Biological warfare in the twentieth century: lessons from the past, challenges for the future." Military Med. 1995; 160: 547-553.
Morgan "A brief review of formaldehyde carcinogenesis in relation to rat nasal pathology and human health risk assessment." ToxicoL PathoL 1997; 25: 291-307.
Mosmann and Coffman, TH1 and TH2 cells: different patterns of lymphokine secretion lead to different functional properties, (1989) Annual Review of Immunology, 7, p. 145-173.
Mosmann, Rapid colorimetric assay for cellular growth and survival: Application to proliferation and cytotoxicity assays, J. Immun. Methods 1983, 65, 55-63.
Muul et al., Identification of specific cytolytic immune responses against autologous tumor in humans bearing malignant melanoma, (1987), J. Immunol. 138:989-995.
O'Hagan "Recent advances in vaccine adjuvants for systemic and mucosal administration." J Pharmacy Pharmacol 1997; 50: 1-10.
O'Neil et al., Detection of shared MHC-restricted human melanoma antigens after vaccinia virus-mediated transduction of genes coding for HLA, (1993) J. Immunol. 151:1410-1418.
Oswein, et al. "Aerosolization of Proteins", 1990; Proceedings of Symposium on Respiratory Drug Delivery II Keystone, Colorado.
Pardoll, Therapeutic vaccination for cancer, 2000 Clin. Immunol. 95 (1): S44-S62.
Pietersz et al., Generation of cellular immune responses to antigenic tumor peptides, 2000 Cell. Mol. Life Sci. 57:290-310.
Pile et al., "Anthrax as a potential biological weapon." Arch. Intern. Med. 1998; 158: 429-434.
Portocala et al., "Immunoelectrophoretic characterization of Sendai virus antigens." Virologie 1976; 27: 261-264.
Remington: The Science and Practice of Pharmacy, Mack Publishing Company, Easton, Pa., 19th edition, 1995.
Russell "Bacterial spores and chemical sporicidal agents." Clin. Micro 1990; 3: 99-119.
Sadovski, Varicella-zoster and herpes simplex virus infections—Tips from other Journals, in American Family Physician, Sep. 15, 1997.
Schulze "Effects of glycolysation on the properties and functions of influenza virus hemagglutinin." J Infect Dis 1997; 176 (Suppl. 1): S24-28.
Sensi et al., T cell receptor (TCR) structure of autologous melanoma-reactive cytotoxic T lymphocyte (CTL) clones: tumor-infiltrating lymphocytes overexpress in vivo the TCR beta chain sequence used by an HLA-A2-restricted and melanocyte-lineage-specific CTL clone, (1993) J. Exp. Med. 178:1231-1246.
Shibata "Germination of inactivated spores of Bacillus cereus T. Effect of preincubation with L-alanine or inosine on the subsequent germination." Japan. J. Microbiol. 1976; 20: 529-535.
Smith et al., "Dihydropyrancarboxamides related to Zanamivir: a new series of inhibitors of influenza virus sialidases. 1. Discovery, synthesis biological activity, and structure-activity relationships of 4-guanidino and 4-amino-4H-pyran-6-carboxamides." J Med Chem 1998; 41: 787-797.
Smith, et al., Pulmonary deposition and clearance of aerosolized alpha-1-proteinase inhibitor administered to dogs and to sheep, J. Clin. Invest. 1989;84:1145-1146.
Solbrig, C. M., Saucier-Sawyer, J. K., Cody, V., Saltzman, W. M., & Hanlon, D. J. (2007). Polymer nanoparticles for immunotherapy from encapsulated tumor-associated antigens and whole tumor cells. Molecular pharmaceutics, 4(1), 47-57.
Tanigawa et al., Effects of tumor necrosis factor-alpha on the in vitro maturation of tumor-reactive effector T cells, J Immunother 2000, 23(5):528-535.
Tarbox et al., "Benzalkonium chloride" 1998 Clinical Orthopaedics and Related Research, 346:255-261.
Titball and Manchee "Factors affecting the germination of spores of Bacillus anthracis." J. Appi. Bact. 1987; 62: 269-273.
Topalian et al., Tumor-specific cytolysis by lymphocytes infiltrating human melanomas, (1989) J. Immunol. 142:3714-3725.
Wadhams et al., "Efficacy of a Surfactant Allantoin and Benzalkonium Chloride Solution for Onychomycosis" Journal of the American Podiatric Medical Association 89(3): 124-130, 1999.
Waghorn and Goa, "Zanamivir." Drugs 1998; 55: 721-725.
Wainberg et al., "Effect of Benzokonium Chloride on HIV and Related Infection on other Infectious Agents" 1987 Arch. AIDS Res., 1:57-68.
Welkos and Friedlander "Pathogenesis and genetic control of resistance to the Sterne strain of Bacillus anthracis." Microb. Path. 1988; 4: 53-69.
Welkos et al., "Differences in susceptibility of inbred mice to Bacillus anthracis" Infect. Immun. 1986; 51: 795-800.
Yanagita, Biochemical Aspects on the Germination of Conidiospores of Aspergillus niger, 1957, Arch Mikrobiol 26:329-344.
Yoshikawa et al: Development of amphiphillic [gamma]—PGA-nanoparticle based tumor vaccine: Potential of the nanoparticulate cytosolic protein delivery carrier, Biochemical and Biophysical Research Communications, vol. 366, No. 2, Dec. 31, 2007 (Dec. 31, 2007), pp. 408-413,XP055079640, ISSN: 0006-291X, DOI: 10.1016/j.bbrc.2007.11.153 http://dx.doi.org/10.1016/j.bbrc.2007.11.153.
Zeitlin et al., "Tests of vaginal microbicides in the mouse genital herpes model." Contraception 1997; 56: 329-335.

* cited by examiner

FIGURE 1

|  | Treatment | 45102 Probsets | | |
|---|---|---|---|---|
|  |  | Up | Down | > 2 fold change over ctrl |
| 6 hrs | $W_{80}5EC$ | 898 | 514 | 1412 |
|  | $W_{80}5EC + rPA$ | 730 | 504 | 1234 |
|  | $P_{407}5EC$ | 18 | 116 | 134 |
|  | $P_{407}5EC + rPA$ | 31 | 329 | 360 |
|  | rPA | 14 | 13 | 27 |
|  | PMA/Iono | 1346 | 766 | 2112 |
|  |  |  |  |  |
| 24hr | $W_{80}5EC$ | nd | nd | nd |
|  | $W_{80}5EC + rPA$ | 1934 | 3273 | 5207 |
|  | $P_{407}5EC$ | 548 | 390 | 938 |
|  | $P_{407}5EC + rPA$ | 531 | 31 | 562 |
|  | rPA | 549 | 6 | 555 |
|  | PMA/Iono | 829 | 4556 | 1285 |

| 6 hrs | Change | | Common with PMA/Iono | |
|---|---|---|---|---|
| Treatment | Up | Down | Up | Down |
| $W_{80}$ | 30 | 8 | 12 | 4 |
| $W_{80}$ + rPA | 23 | 10 | 14 | 4 |
| $P_{407}$ | 0 | 2 | na | 0 |
| $P_{407}$ + rPA | 0 | 12 | na | 0 |
| rPA | 0 | 0 | na | na |
| PMA/Iono | 49 | 18 | | |

C

| 24 hrs | Change | | Common with PMA/Iono | |
|---|---|---|---|---|
| Treatment | Up | Down | Up | Down |
| $W_{80}$ | X | X | X | X |
| $W_{80}$ + rPA | 52 | 49 | 8 | 7 |
| $P_{407}$ | 9 | 13 | 7 | 3 |
| $P_{407}$ + rPA | 9 | 0 | 3 | na |
| rPA | 8 | 0 | 7 | na |
| PMA/Iono | 15 | 8 | | |

FIGURE 4

|       | W80  |       | P407 |       | PMA  |       |
|-------|------|-------|------|-------|------|-------|
|       | 6hrs | 24hrs | 6hrs | 24hrs | 6hrs | 24hrs |
| CD1a  | ns   | ns    | ns   | ns    | ns   | ns    |
| CD14  | ns   | -1.64 | ns   | ns    | ns   | ns    |
| CD40  | ns   | ns    | ns   | ns    | ns   | ns    |
| CD80  | ns   | -2.6  | ns   | ns    | ns   | ns    |
| CD83  | 3.33 | 3.98  | ns   | 1.1   | 1    | 1     |
| CD86  | ns   | 1.16  | ns   | ns    | ns   | ns    |
| MHCII | ns   | ns    | ns   | ns    | ns   | ns    |

9 Week Serum Screen for IgG by ELISA

| | Emulsion | Zeta Potential (mV) | Standard Deviation |
|---|---|---|---|
| | W805EC | 16.4 | 5.43 |
| | W805E | -8.26 | 4.44 |
| OVA | P4075EC | 28 | 7.81 |

9 Week Serum Screen for IgG by ELISA

|  | Emulsion | Zeta Potential (mV) | Standard Deviation |
|---|---|---|---|
|  | W805EC | 42.7 | 6.24 |
|  | W805E | -2.83 | 4.27 |
| BSA | P4075EC | 37.1 | 15.5 |

2 Week Serum Screen for IgG by ELISA

| | Emulsion | Zeta Potential (mV) | Standard Deviation |
|---|---|---|---|
| | W805EC | 50.1 | 5.96 |
| | W805E | -5.25 | 4.13 |
| Lys | P4075EC | 32.3 | 6.5 |

A.

Nanoemulsion: $W_{80}5EC$ $P_{407}5EC$ (-) PMA/Iono

Antigen (PA)  (-) (+) (+) (-) (+) (-)
PMA/Iono

B.

$W_{80}5EC$ $P_{407}5EC$

Healthy lung

Lung with MC-38 metastases

Intranasal vaccination reduces number of metastases in mice lungs

A

B

CANCER VACCINE COMPOSITIONS AND METHODS OF USING THE SAME

CROSS-REFERENCE TO RELATED APPLICATIONS

The present application is a national phase application under 35 U.S.C. § 371 of PCT International Application No. PCT/US2009/064822, filed on Nov. 17, 2009, which claims priority to U.S. Provisional Patent Application Ser. No. 61/115,421, filed on Nov. 17, 2008, the contents of which are each hereby incorporated by reference in their entireties.

FIELD OF THE INVENTION

The present invention provides methods and compositions for the stimulation of immune responses. In particular, the present invention provides nanoemulsion compositions (e.g., vaccines) and methods of using the same for the induction of immune responses (e.g., innate and adaptive immune responses (e.g., for generation of host immunity against cancer (e.g., a tumor))). Compositions and methods of the present invention find use in, among other things, clinical (e.g. therapeutic and preventative medicine (e.g., vaccination)) and research applications.

BACKGROUND

Success in cancer therapy has conventionally been accomplished by surgical reduction of a tumor mass and subsequent chemo- and/or radiotherapy. This strategy can reduce the tumor and, in less advanced stages, often results in complete remission. Unfortunately, the prognosis for more advanced tumors has changed little over the past 50 years and a significant proportion of cancer-related deaths are caused by subsequent metastases. New prophylactic and therapeutic treatments are needed to combat the increasing occurrence of cancer.

SUMMARY OF THE INVENTION

The present invention provides methods and compositions for the stimulation of immune responses. In particular, the present invention provides nanoemulsion compositions (e.g., vaccines) and methods of using the same for the induction of immune responses (e.g., innate and adaptive immune responses (e.g., for generation of host immunity against cancer (e.g., a tumor))). Compositions and methods of the present invention find use in, among other things, clinical (e.g. therapeutic and preventative medicine (e.g., vaccination)) and research applications.

In accordance with an aspect of the present invention, there is provided a composition for stimulating a cancer specific immune response comprising: a nanoemulsion; and a cancer immunogen. The invention is not limited to any particular nanoemulsion. Indeed, a variety of nanoemulsions may be utilized including, but not limited to, those described herein. In some embodiments, the cancer immunogen comprises cancer cells. In some embodiments, the cancer cells have undergone freeze-thaw lysis. In some embodiments, the cancer cells have been exposed to UV radiation. In some embodiments, the cancer immunogen comprises one or a plurality of tumor associated antigens. In some embodiments, the tumor associated antigens are recombinantly produced. In some embodiments, the tumor associated antigens are purified. In some embodiments, the composition further comprises an adjuvant. The present invention is not limited to any particular adjuvant. Indeed, a variety of adjuvants can be utilized including those disclosed herein. In some embodiments, the adjuvant induces a T helper cell type 1 immune response when administered to a subject. In some embodiments, the composition is formulated for nasal administration. In some embodiments, the composition is formulated for other routes of administration including, but not limited to, intradermal, subcutaneous, transdermal, intramuscular, mucosal or other route of administration.

The present invention also provides a method of inducing a cancer specific immune response in a subject comprising: providing a composition for stimulating a cancer specific immune response comprising a nanoemulsion and a cancer immunogen; and a subject, and administering the composition to the subject under conditions such that the subject produces a cancer specific immune response. In some embodiments, the method decreases the incidence of cancer metastasis in the subject. The present invention is not limited by the type of cancer to which an immune response is generated. Indeed, an immune response can be generated against a variety of different types of cancer utilizing the compositions and methods described herein including, but not limited to, breast cancer, ovarian cancer, endometrial cancer, colorectal cancer, lung cancer, renal cancer, melanoma, kidney cancer, prostate cancer, brain cancer, sarcomas, or a combination thereof. In some embodiments, the cancer specific immune response provides an immunoprotective (e.g., comprising a memory immune response) and/or therapeutic response in the subject. In some embodiments, the method is utilized post-surgical removal of cancer in the subject. In some embodiments, the method produces a T helper cell type 1 response in the subject. In some embodiments, the method induces memory cytotoxic T lymphocytes in the subject. In some embodiments, the composition is administered via intranasal instillation. In some embodiments, the administration of the composition results in cancer immunogen delivered to immunological sites in the subject. In some embodiments, the immunological sites are the sinus, lymph nodes, and/or thymus, although the present invention is not so limited. In some embodiments, the subject is substantially susceptible to recurrence of cancer.

The present invention also provides a method of treating a disease comprising the step of administering to a subject a pharmaceutical composition comprising an immunologically effective amount of a composition comprising a nanoemulsion and a cancer immunogen. In some embodiments, the disease is a proliferative cell disorder (e.g., one of the various types of proliferative disorders described herein). In some embodiments, the disease is cancer. The present invention is not limited by the type of cancer treated. Indeed, a variety of different types of cancer are treatable utilizing the compositions and methods described herein including, but not limited to, breast cancer, ovarian cancer, endometrial cancer, colorectal cancer, lung cancer, renal cancer, melanoma, kidney cancer, prostate cancer, brain cancer, sarcomas, or a combination thereof.

In yet another aspect of the invention, there is provided a method of modulating an immune response to cancer in a subject comprising combining a cancer antigen/immunogen with a nanoemulsion composition of the present invention and administering an effective amount to the subject to modulate an immune response to cancer in the subject.

In a further aspect of the invention, there is provided a method of generating an immune response in a subject, including a human, comprising administering thereto an immunogenic nanoemulsion vaccine of the present invention (e.g., independently and/or in combination with one or more other therapeutics (e.g., anti-cancer drugs and/or chemotherapeutics). The immune response attained may be a humoral immune response and/or a cell-mediated immune response.

In some embodiments of the present invention, there is provided a kit for preparing an immunogenic nanoemulsion vaccine composition, comprising: (a) means for containing a nanoemulsion; and (b) means for containing at least one cancer antigen/immunogen; and (c) means for combining the nanoemulsion and at least one cancer antigen/immunogen to produce the immunogenic composition. The present invention provides several advantages over conventional vaccines including, but not limited to, ease of formulation; effectiveness of adjuvanticity; lack of unwanted toxicity and/or host morbidity; and compatibility of antigens/immunogens with the nanoemulsion composition.

In some embodiments, the present invention provides a method of inducing an immune response to one or a plurality of cancer immunogens (e.g., two or more (e.g., three, four, five, six, seven, eight, or more immunogens), comprising providing a nanoemulsion; and one or a plurality of cancer immunogens; combining the nanoemulsion with the cancer immunogens; and administering the combined nanoemulsion and immunogens to a subject under conditions such that the subject produces an immune response to the immunogens. In some embodiments, administering comprises mucosal administration. In some embodiments, inducing an immune response induces immunity to each of the plurality of immunogens in the subject. In some embodiments, immunity comprises systemic immunity. In some embodiments, immunity comprises mucosal immunity. In some embodiments, the immune response comprises increased expression of IFN-γ in the subject. In some embodiments, the immune response comprises increased expression of TNF-α in the subject. In some embodiments, the immune response comprises a systemic IgG response to the immunogens. In some embodiments, the immune response comprises a mucosal IgA response to the immunogens. In some embodiments, the composition comprises between 1 and 500 µg (e.g., between 15 and 75, 75-150, 150-300, 300-500 or more µg) of a recombinant cancer immunogen. The present invention is not limited to this amount of immunogen. Indeed, a variety of doses of immunogen are contemplated to be useful in the present invention.

The present invention further provides a kit comprising a vaccine, the vaccine comprising a nanoemulsion and one or more cancer immunogens, the nanoemulsion comprising an aqueous phase, an oil phase, and a solvent. In some embodiments, the kit further comprises instructions for using the kit for vaccinating a subject against the one or more immunogens.

The present invention is not limited to a particular oil. A variety of oils are contemplated, including, but not limited to, soybean, avocado, squalene, olive, canola, corn, rapeseed, safflower, sunflower, fish, flavor, and water insoluble vitamins. The present invention is also not limited to a particular solvent. A variety of solvents are contemplated including, but not limited to, an alcohol (e.g., including, but not limited to, methanol, ethanol, propanol, and octanol), glycerol, polyethylene glycol, and an organic phosphate based solvent.

In some embodiments, the emulsion further comprises a surfactant. The present invention is not limited to a particular surfactant. A variety of surfactants are contemplated including, but not limited to, nonionic and ionic surfactants (e.g., TRITON X-100; TWEEN 20; and TYLOXAPOL).

In certain embodiments, the emulsion further comprises a cationic halogen containing compound. The present invention is not limited to a particular cationic halogen containing compound. A variety of cationic halogen containing compounds are contemplated including, but not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides. The present invention is also not limited to a particular halide. A variety of halides are contemplated including, but not limited to, halide selected from the group consisting of chloride, fluoride, bromide, and iodide.

In still further embodiments, the emulsion further comprises a quaternary ammonium containing compound. The present invention is not limited to a particular quaternary ammonium containing compound. A variety of quaternary ammonium containing compounds are contemplated including, but not limited to, Alkyl dimethyl benzyl ammonium chloride, dialkyl dimethyl ammonium chloride, n-Alkyl dimethyl benzyl ammonium chloride, n-Alkyl dimethyl ethylbenzyl ammonium chloride, Dialkyl dimethyl ammonium chloride, and n-Alkyl dimethyl benzyl ammonium chloride.

In still further embodiments, the present invention provides a method of inducing immunity to one or more cancer immunogens, comprising providing a nanoemulsion adjuvant comprising an aqueous phase, an oil phase, and a solvent; and one or more immunogens; combining the emulsion with the one or more cancer immunogens to generate a vaccine composition; and administering the vaccine composition to a subject. In some embodiments, administering comprises contacting the vaccine composition with a mucosal surface of the subject. For example, in some embodiments, administering comprises intranasal administration. In some preferred embodiments, the administering occurs under conditions such that the subject generates immunity to the one or more cancer immunogens (e.g., via generating humoral immune responses to the one or more immunogens). In some embodiments, immune responses in the subject comprise generation of antibodies to the immunogens. In some embodiments, the antibodies generated comprise IgG and/or IgA antibodies. In some embodiments, the immune responses generated in a subject via administration of a nanoemulsion composition comprising a plurality of immunogens (e.g., two, three, four, five, six, seven, eight, or more immunogens) are similar to the immune responses that are generated in a subject via administration of a plurality of nanoemulsion compositions, wherein each nanoemulsion composition comprises a single immunogen (e.g., the antigen specific antibody titer levels in a subject administered a composition comprising plurality of immunogens is similar to the antigen specific antibody titer levels in a subject administered a plurality of nanoemulsion compositions wherein each composition comprises a single immunogen).

The present invention is not limited by the nature of the immune response generated. In some embodiments, a nanoemulsion vaccine described herein stimulates and/or elicits an adaptive and/or acquired immune response in a host. In some embodiments, a nanoemulsion vaccine provided herein skews an immune response toward a Th1 type response. In some embodiments, a nanoemulsion vaccine provided herein skews an immune response toward a Th2 type response. In some embodiments, a nanoemulsion vaccine provided herein provides a balanced Th1/Th2 response and/or polarization (e.g., an IgG subclass distribution and cytokine response indicative of a balanced Th1/Th2 response). Thus, a variety of immune responses may be generated and measured in a subject administered a nanoemulsion vaccine of the present invention including, but not limited to, activation, proliferation or differentiation of cells of the immune system (e.g., B cells, T cells, dendritic cells, antigen presenting cells (APCs), macrophages, natural killer (NK) cells, etc.); up-regulated or down-regulated expression of markers and cytokines; stimulation of IgA, IgM, and/or IgG titers; splenomegaly (e.g., increased spleen cellularity); hyperplasia, mixed cellular infiltrates in various organs, and/or other responses (e.g., of cells) of the immune system that can be assessed with respect to immune stimulation known in the art. In some embodiments, administering comprises contacting a mucosal surface of the subject with the vaccine. The present invention is not limited by the mucosal surface contacted. In some preferred embodiments, the mucosal surface comprises nasal mucosa. In some embodiments, the mucosal surface comprises vaginal mucosa. In some embodiments, administrating comprises parenteral administration. The present invention is not limited by the route chosen for administration of a vaccine of the present invention. In some embodiments, inducing an immune response primes the immune system of a host to respond to (e.g., to produce a Th1 and/or Th2 type response (e.g., thereby providing protective immunity) one or cancer targets (e.g., cancer cells that have otherwise evaded a host's immune system) in the host subject (e.g., human or animal subject). In some embodiments, the immunity comprises systemic immunity. In some embodiments, the immunity comprises mucosal immunity. In some embodiments, the immune response comprises increased expression of IFN-γ and/or TNF-α in the subject. In some embodiments, the immune response comprises a systemic IgG response. In some embodiments, the immune response comprises a mucosal IgA response. In some embodiments, the composition comprises a 10% nanoemulsion adjuvant solution. However, the present invention is not limited to this amount (e.g., percentage) of nanoemulsion. For example, in some embodiments, a composition comprises less than 10% nanoemulsion (e.g., 9%, 8%, 7%, 6%, 5%, 4%, 3%, 2% or 1%). In some embodiments, a composition comprises more than 10% nanoemulsion (e.g., 15%, 20%, 25%, 30%, 35%, 40%, 45%, 50%, 60% or more). In some embodiments, a vaccine of the present invention comprises any of the nanoemulsions described herein. In some embodiments, the nanoemulsion vaccine comprises $W_{20}5EC$. In some embodiments, the nanoemulsion vaccine comprises $W_{80}5EC$. In some embodiments, the nanoemulsion vaccine is X8P. In some embodiments, the nanoemulsion vaccine comprises $P_{407}5EC$. In some embodiments, immune responses resulting from administration of a nanoemulsion vaccine protects the subject from displaying signs or symptoms of disease (cancer). In some embodiments, immune responses resulting from administration of a nanoemulsion vaccine protects a subject from cancer metastasis and/or cancer growth at a primary site. In some embodiments, a nanoemulsion vaccine comprises one or more adjuvants. The present invention is not limited by the type of adjuvant utilized. In some embodiments, the adjuvant is a CpG oligonucleotide. In some embodiments, the adjuvant is monophosphoryl lipid A. A number of other adjuvants that find use in the present invention are described herein. In some embodiments, the subject is a human. In some embodiments, immune responses resulting from administration of a nanoemulsion vaccine reduces the risk of recurrence of cancer in the subject (e.g., post surgical removal of cancer from the subject).

DESCRIPTION OF THE FIGURES

The following figures form part of the present specification and are included to further demonstrate certain aspects and embodiments of the present invention. The invention may be better understood by reference to one or more of these figures in combination with the description of specific embodiments presented herein.

FIG. 1 shows the overall changes in gene expression from microarray analysis. The number of genes which exhibited an increase or decrease in gene expression are indicated for each condition tested.

FIG. 2 shows changes in expression of genes associated with the mitogen activated protein kinase (MAPK) pathway. a) Data represent pattern of gene expression grouped in the MAPK pathway. Red and pink colors indicate over a 4-fold and 2-4-fold increase, respectively, in a gene-specific transcript expression. Green color indicates more than a 2-fold decrease in transcript expression. Changes in gene expression were computed in comparison to non-treated controls. The number of genes that exhibited an increase or decrease in gene expression are indicated for each condition tested at 6 hours (b) and 24 hours (c).

FIG. 4 shows RNA expression of dendritic cell surface markers following exposure of cells to NE for 6 or 24 hours. Pink color indicates an increase in transcript expression as compared to non-treated controls, while the green indicates a decrease. Numbers reflect log 2 of expression change as compared to non-stimulated controls. DC40, CD80, CD83 and CD86 are dendritic cell maturation markers.

GENERAL DESCRIPTION OF THE INVENTION

Figure 3:
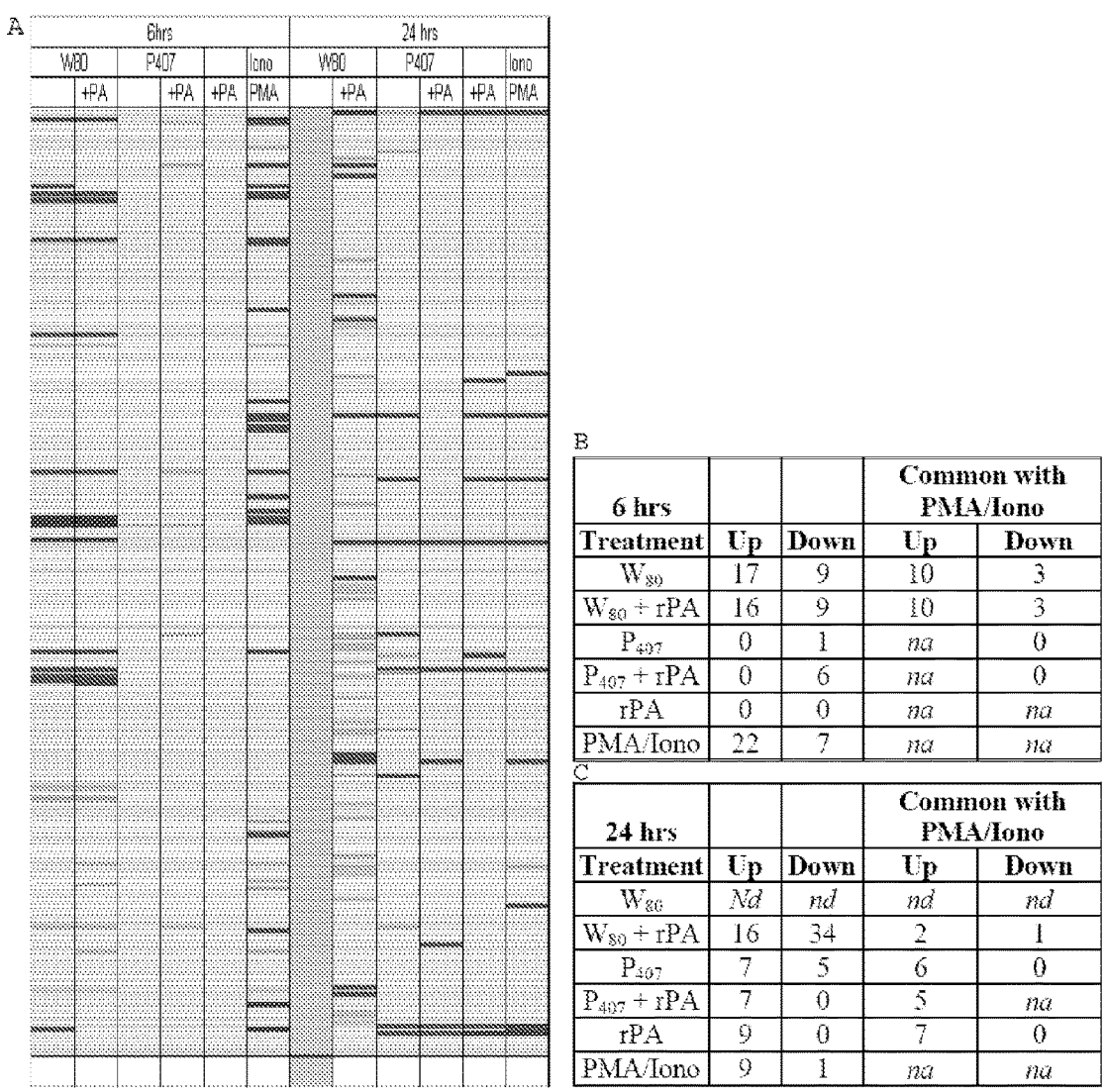
FIG. 3 shows changes in expression of genes associated T cell receptor (TCR) pathway. a) Data represent pattern of gene expression grouped in the TCR pathway. Red and pink colors indicate over a 4-fold and 2-4-fold increase, respectively, in a gene-specific transcript expression. Green color indicates more than a 2-fold decrease in transcript expression. Changes in gene expression were computed in comparison to non-treated controls. The number of genes that exhibited an increase or decrease in gene expression are indicated for each condition tested at 6 hours (b) and 24 hours (c).

The present invention provides compositions and methods for the stimulation of immune responses. In particular, the present invention provides nanoemulsion compositions (e.g., vaccines (e.g., cancer vaccines)) and methods of using the same for the induction of immune responses (e.g., innate and/or adaptive immune responses (e.g., for generation of host immunity against a tumor)).

In some embodiments, the present invention provides compositions and methods for the stimulation of immune responses. Specifically, the present invention provides nanoemulsion (NE) cancer vaccine compositions and methods of using the same (e.g., individually or together with one or more compositions (e.g., chemotherapeutics and/or anti-cancer drugs) and/or methods (e.g., T regulatory cell depletion) to induce an immune response in a subject (e.g., to prime, enable and/or enhance an immune response (e.g., innate and/or adaptive immune responses (e.g., for generation of host immunity against a tumor)). Compositions and methods of the present invention find use in, among other things, clinical (e.g. therapeutic and preventative medicine (e.g., vaccination)) and research applications. In some embodiments, a NE cancer vaccine of the invention comprises a NE and whole cancer cells (e.g., that have undergone freeze-thaw lysis). In some embodiments, a NE cancer vaccine of the invention comprises a NE and homogenized cells (e.g., cancer cells (e.g., a cancer cell line or genetically modified cancer cells). In some embodiments, a NE cancer vaccine of the invention comprises a NE and cells (e.g., cancer cells (e.g., that have been exposed to UV radiation). In some embodiments, a NE cancer vaccine of the invention comprises a NE and one or a plurality of tumor associated antigens. In some embodiments, a NE cancer vaccine of the invention comprises a NE and cells modified (e.g., genetically modified) to express (e.g., over-express) one or a plurality of tumor associated antigens. In some embodiments, one or a plurality of protein components (e.g., isolated and/or purified and/or recombinant protein) from one or a plurality of cancer cells are mixed with NE and utilized to induce an immune response in a subject. In some embodiments, a NE cancer vaccine of the invention comprises one or more adjuvants (e.g., a nanoemulsion adjuvant and/or non-nanoemulsion adjuvant).

Although an understanding of the mechanism is not necessary to practice the present invention and the present invention is not limited to any particular mechanism of action, in some embodiments, NE cancer vaccines of the present invention preserve important antigenic epitopes (e.g., recognizable by a subject's immune system), stabilizing their hydrophobic and hydrophilic components in the oil and water interface of the emulsion (e.g., thereby providing one or more immunogens (e.g., stabilized antigens (e.g., tumor associated antigens (TAAs)) against which a subject's immune system can mount an immune response). In other embodiments, because NE formulations penetrate the mucosa (e.g., through pores), the vaccine formulations carry NE cancer vaccine components (e.g., immunogens (e.g., TAAs) to submucosal locations (e.g., the sinus, submandibular lymph nodes, thymus, etc. (e.g., comprising dendritic cells (e.g., dendritic cells involved in initiating and/or stimulating an immune response)). Although an understanding of the mechanism is not necessary to practice the present invention and the present invention is not limited to any particular mechanism of action, in some embodiments, combining a NE and cells (e.g., cancer cells (e.g., lysed, UV irradiated, homogenized, genetically modified, etc.) and/or protein components (e.g., isolated and/or purified and/or recombinant protein from one or a plurality of cancer cells) stabilizes the cells and/or protein components and immunogenic portions thereof thereby providing a proper immunogenic material for generation of an immune response.

Dendritic cells avidly phagocytose nanoemulsion (NE) oil droplets and this may, in some embodiments, provide a means to prime, enable and/or enhance an immune response (e.g., an anti-tumor immune response) toward a Th1 and/or Th2 type response, as well as to internalize immunogens (e.g., antigenic proteins or peptide fragments thereof present in the NE) for antigen presentation. While some vaccines rely on inflammatory toxins or other immune stimuli for adjuvant activity (See, e.g., Holmgren and Czerkinsky, Nature Med. 2005, 11; 45-53), NEs have not been shown to be inflammatory when placed on the skin or mucous membranes in studies on animals and in humans. Thus, although an understanding of the mechanism is not necessary to practice the present invention and the present invention is not limited to any particular mechanism of action, in some embodiments, a composition comprising a NE of the present invention (e.g., a composition comprising NE cancer vaccine) acts as a "physical" adjuvant (e.g., that transports and/or presents immunogens (e.g., TAAs) to the immune system. In some embodiments, mucosal administration of a composition of the present invention generates mucosal (e.g., signs of mucosal immunity (e.g., generation of IgA antibody titers)) as well as systemic immunity. In some embodiments, mucosal administration of a NE vaccine of the invention generates an innate immune response (e.g., activates Toll-like receptor signaling and/or activation of NF-kB) in a subject.

Both cellular and humoral immunity play a role in protection against abnormal cellular growth and both can be induced with the NE vaccine formulations of the present invention. Thus, in some embodiments, administration (e.g., mucosal administration) of a nanoemulsion vaccine of the present invention primes, enables and/or enhances induction of both humoral (e.g., development of specific antibodies) and cellular (e.g., cytotoxic T lymphocyte) immune responses (e.g., against a tumor and/or against cancer metastasis). In some embodiments, nanoemulsions described herein are utilized in a vaccine (e.g., a cancer vaccine (e.g., a prophylactic vaccine and/or a therapeutic vaccine). Thus, in some embodiments, the present invention provides NE cancer vaccines and methods of utilizing the same to prevent tumor metastasis. In some embodiments, the present invention provides NE cancer vaccines and methods of utilizing the same to skew a subject's immune response toward an anti-tumor immune response (e.g., toward a Th1 type immune response). In some embodiments, the present invention provides NE cancer vaccines and methods of utilizing the same to prime professional antigen presenting cells (APCs)(e.g., to present cancer associated antigens to a subject's immune system). In some embodiments, the present invention provides NE cancer vaccines and methods of utilizing the same to expand a subject's CD8+ cytotoxic T lymphocyte population (e.g., anti-cancer/tumor CD8+ cytotoxic T lymphocyte population). In some embodiments, the present invention provides NE cancer vaccines and methods of utilizing the same to expand a subject's CD4+ T cells (e.g., involved in generation of CD8+ anti-cancer memory cells). In some embodiments, the present invention provides NE cancer vaccines and methods of utilizing the same to suppress development of T regulatory cells (Tregs). In some embodiments, NE cancer vaccines provided herein are utilized as mucosal vaccine (e.g., for administration to the nasal mucosa).

Definitions

To facilitate an understanding of the present invention, a number of terms and phrases are defined below:

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

The terms "host" or "subject," as used herein, refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention (e.g., a composition for inducing an immune response).

The terms "emulsion" and "nanoemulsion" as used herein, includes classic oil-in-water or water in oil dispersions or droplets, as well as other lipid structures that can form as a result of hydrophobic forces that drive apolar residues (e.g., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in some embodiments, the nanoemulsions comprise an oil phase having droplets with a mean particle size of approximately 0.1 to 5 microns (e.g., about 150, 200, 250, 300, 350, 400, 450, 500 nm or larger in diameter), although smaller and larger particle sizes are contemplated. The terms "emulsion" and "nanoemulsion" are often used herein, interchangeably, to refer to the nanoemulsions of the present invention.

As used herein, the terms "contact," "contacted," "expose," "exposed," and "mixed" when used in reference to a nanoemulsion and other material (e.g., cancer cells), refer to bringing one or more nanoemulsions into contact with the material. The present invention is not limited by the amount or type of nanoemulsion used for microorganism inactivation. A variety of nanoemulsions that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion and cancerous material (e.g., cancer cells, proteins, antigenic determinants, etc.) are contemplated in the present invention including, but not limited to, those described herein.

The term "surfactant" refers to any molecule having both a polar head group, which energetically prefers solvation by water, and a hydrophobic tail that is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described, for example, by Meyers, (See, e.g., Meyers, *Surfactant Science and Technology*, VCH Publishers Inc., New York, pp. 231-245 (1992)), incorporated herein by reference. As used herein where appropriate, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein the term "interaction enhancers" refers to compounds that act to enhance the interaction of an emulsion with a microorganism (e.g., with a cell wall of a bacteria (e.g., a Gram negative bacteria) or with a viral envelope (e.g., Vaccinia virus envelope)). Contemplated interaction enhancers include, but are not limited to, chelating agents (e.g., ethylenediaminetetraacetic acid (EDTA), ethylenebis (oxyethylenenitrilo)tetraacetic acid (EGTA), and the like) and certain biological agents (e.g., bovine serum albumin (BSA) and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., resulting in total or partial immunity to and/or clearance of an immunogen (e.g., tumor) and/or prevents growth and/or metastasis of an immunogen (e.g., tumor) in a subject). In some embodiments of the invention, the composition comprises a nanoemulsion and an antigen/immunogen (e.g., whole cancer cells (e.g., that have undergone freeze-thaw lysis and/or other type of membrane disruption), homogenized cells (e.g., cancer cells (e.g., a cancer cell line or genetically modified cancer cells), cells (e.g., cancer cells (e.g., that have been exposed to UV radiation), one or a plurality of tumor associated antigens (e.g., recombinant and/or purified protein antigens), cells modified (e.g., genetically modified) to express (e.g., over-express) one or a plurality of tumor associated antigens, one or a plurality of protein components (e.g., isolated and/or purified and/or recombinant protein) from one or a plurality of cancer cells, and/or one or more adjuvants (e.g., a nanoemulsion adjuvant and/or non-nanoemulsion adjuvant).

In some embodiments, the composition comprising a nanoemulsion and an immunogen comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response. Thus, in some preferred embodiments, a composition comprising a nanoemulsion and an immunogen is administered to a subject as a vaccine (e.g., to prevent or attenuate a disease (e.g., cancer (e.g., by providing to the subject total or partial immunity against the disease or the total or partial attenuation (e.g., suppression) of a sign, symptom or condition of the disease))).

As used herein, the term "adjuvant" refers to any substance that can stimulate an immune response (e.g., a mucosal immune response). Some adjuvants can cause activation of a cell of the immune system (e.g., an adjuvant can cause an immune cell to produce and secrete a cytokine). Examples of adjuvants that can cause activation of a cell of the immune system include, but are not limited to, the nanoemulsion formulations described herein, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). Traditional adjuvants are well known in the art and include, for example, aluminum phosphate or hydroxide salts ("alum"). In some embodiments, nanoemulsion cancer vaccine compositions are administered with one or more adjuvants (e.g., to skew the immune response towards a Th1 and/or Th2 type response).

As used herein, the term "an amount effective to induce an immune response" (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route.

As used herein, the term "under conditions such that said subject generates an immune response" refers to any qualitative or quantitative induction, generation, and/or stimulation of an immune response (e.g., innate or acquired).

As used herein, the term "immune response" refers to a response by the immune system of a subject. For example, immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the terms "toll receptors" and "TLRs" refer to a class of receptors (e.g., TLR1, TLR2, TLR3, TLR4, TLR5, TLR6, TLR7, TLR8, TLR9, TLRT0, TLR 11) that recognize special patterns of pathogens, termed pathogen-associated molecular patterns (See, e.g., Janeway and Medzhitov, (2002) Annu. Rev. Immunol 20, 197-216). These receptors are expressed in innate immune cells (e.g., neutrophils, monocytes, macrophages, dendritic cells) and in other types of cells such as endothelial cells. Their ligands include bacterial products such as LPS, peptidoglycans, lipopeptides, and CpG DNA. TLRs are receptors that bind to exogenous ligands and mediate innate immune responses leading to the elimination of invading microbes. The TLR-triggered signaling pathway leads to activation of transcription factors including NFkB, which is important for the induced expression of proinflammatory cytokines and chemokines. TLRs also interact with each other. For example, TLR2 can form functional heterodimers with TLR1 or TLR6. The TLR2/1 dimer has a different ligand binding profile than the TLR2/6 dimer (Ozinsky et al., 2000). In some embodiments, a nanoemulsion adjuvant activates cell signaling through a TLR (e.g., TLR2 and/or TLR4). Thus, in some embodiments, methods described herein include a nanoemulsion cancer vaccine that when administered to a subject, activates one or more TLRs and stimulates an immune response (e.g., innate and/or adaptive/acquired immune response) in a subject. Vaccine compositions described herein can in some embodiments activate TLRs (e.g., TLR2 and/or TLR4) by, for example, interacting with TLRs (e.g., NE binding to TLRs) or activating any downstream cellular pathway that occurs upon binding of a ligand to a TLR. In some embodiments, vaccine compositions described herein that activate TLRs also enhance the availability or accessibility of any endogenous or naturally occurring ligand of TLRs. In some embodiments, vaccine compositions described herein that activate one or more TLRs alter transcription of genes, increase translation of mRNA or increase the activity of proteins that are involved in mediating TLR cellular processes.

As used herein, the term "immunity" refers to protection from disease (e.g., preventing or attenuating (e.g., suppression) of a sign, symptom or condition of the disease (e.g., tumor metastasis)) upon exposure a vaccine composition described herein Immunity can be innate (e.g., non-adaptive (e.g., non-acquired) immune responses that exist in the absence of a previous exposure to an antigen) and/or acquired/adaptive (e.g., immune responses that are mediated by B and/or T cells following a previous exposure to antigen (e.g., that exhibit increased specificity and reactivity to the antigen)).

As used herein, the terms "immunogen" and "antigen" refer to an agent (e.g., whole cancer cells (e.g., that have undergone freeze-thaw lysis and/or other type of membrane disruption), homogenized cells (e.g., cancer cells (e.g., a cancer cell line or genetically modified cancer cells), cells (e.g., cancer cells (e.g., that have been exposed to UV radiation), one or a plurality of tumor associated antigens (e.g., recombinant and/or purified protein antigens), cells modified (e.g., genetically modified) to express (e.g., over-express) one or a plurality of tumor associated antigens, one or a plurality of protein components (e.g., isolated and/or purified and/or recombinant protein) from one or a plurality of cancer cells, and/or one or more adjuvants (e.g., a nanoemulsion adjuvant and/or non-nanoemulsion adjuvant) that is capable of eliciting an immune response in a subject. In preferred embodiments, immunogens elicit immunity against and/or clearance of, or prevent growth and/or metastasis of cancer (e.g., tumors) when administered in combination with a nanoemulsion of the present invention.

As used herein, the term "enhanced immunity" refers to an increase in the level of adaptive and/or acquired immunity in a subject to a given immunogen following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention (e.g., a composition for inducing an immune response (e.g., a composition comprising a nanoemulsion and an immunogen)) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, etc.), topically, and the like.

As used herein, the terms "co-administration" and "co-administering" refer to the administration of at least two agent(s) (e.g., a composition comprising a nanoemulsion and an immunogen and one or more other agents—e.g., an adjuvant) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "topically" refers to application of a compositions of the present invention (e.g., a composition comprising a nanoemulsion and an immunogen) to the surface of the skin and/or mucosal cells and tissues (e.g., alveolar, buccal, lingual, masticatory, vaginal or nasal mucosa, and other tissues and cells which line hollow organs or body cavities).

In some embodiments, the compositions of the present invention are administered in the form of topical emulsions, injectable compositions, ingestible solutions, and the like. When the route is topical, the form may be, for example, a spray (e.g., a nasal spray), a cream, or other viscous solution (e.g., a composition comprising a nanoemulsion and an immunogen in polyethylene glycol).

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethylene glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease (e.g., cancer).

"Nasal application", as used herein, means applied through the nose into the nasal or sinus passages or both. The application may, for example, be done by drops, sprays, mists, coatings or mixtures thereof applied to the nasal and sinus passages.

"Vaginal application", as used herein, means applied into or through the vagina so as to contact vaginal mucosa. The application may contact the urethra, cervix, formix, uterus or other area surrounding the vagina. The application may, for example, be done by drops, sprays, mists, coatings, lubricants or mixtures thereof applied to the vagina or surrounding tissue.

As used herein, the term "kit" refers to any delivery system for delivering materials. In the context of immunogenic agents (e.g., compositions comprising a nanoemulsion and an immunogen), such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunogenic agents (e.g., nanoemulsions) and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a nanoemulsion and an immunogen for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

As used herein, the term "immunoglobulin" or "antibody" refer to proteins that bind a specific antigen Immunoglobulins include, but are not limited to, polyclonal, monoclonal, chimeric, and humanized antibodies, Fab fragments, $F(ab')_2$ fragments, and includes immunoglobulins of the following classes: IgG, IgA, IgM, IgD, IbE, and secreted immunoglobulins (sIg) Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, $F(ab')_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (e.g., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the terms "epithelial tissue" or "epithelium" refer to the cellular covering of internal and external surfaces of the body, including the lining of vessels and other small cavities. Epithelium is classified into types on the basis of the number of layers deep and the shape of the superficial cells.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass or increased PSA level) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, etc.

As used herein, the term "post surgical tumor tissue" refers to cancerous tissue (e.g., prostate tissue) that has been removed from a subject (e.g., during surgery).

As used herein, the term "identifying the risk of said tumor metastasizing" refers to the relative risk (e.g., the percent chance or a relative score) of a tumor (e.g., prostate, colon, breast, etc. tumor) metastasizing.

The term "cancer" as used herein is defined as a tissue of uncontrolled growth or proliferation of cells, such as a tumor. The present invention is not limited by the type of cancer (e.g., prophylactically and/or therapeutically treated). Indeed, a variety of cancers may be treated with compositions and methods described herein including, but not limited to, epithelial cancer, breast cancer, ovarian cancer, endometrial cancer, colorectal cancer, lung cancer, renal cancer, melanoma, kidney cancer, prostate cancer, brain cancer, sarcomas, melanomas, carcinomas, and/or a combination thereof.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "identifying the risk of said tumor recurring" refers to the relative risk (e.g., the percent chance or a relative score) of a tumor (e.g., prostate tumor tissue) recurring in the same organ as the original tumor (e.g., prostate).

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer.

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize).

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk-cell lines, the CAD gene that is used in conjunction with CAD-deficient cells and the mammalian hypoxanthine-guanine phosphoribosyl transferase (hprt) gene that is used in conjunction with hprt-cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention provides methods and compositions for the stimulation of immune responses. In particular, the present invention provides nanoemulsion compositions (e.g., vaccines) and methods of using the same for the induction of immune responses (e.g., innate and adaptive immune responses (e.g., for generation of host immunity against a tumor)). Compositions and methods of the present invention find use in, among other things, clinical (e.g. therapeutic and preventative medicine (e.g., vaccination)) and research applications.

Nanoemulsion Cancer Vaccine Formulations and Methods of Inducing Immune Responses Evidence that an immune response to cancer exists in humans is provided by the existence of tumor reactive lymphocytes within melanoma deposits. These lymphocytes, when isolated, are capable of recognizing specific tumor antigens on autologous and allogeneic melanomas in an MHC restricted fashion. (See, e.g., Itoh, K. et al. (1986), Cancer Res. 46:3011-3017; Muul et al. (1987), J. Immunol. 138:989-995; Topalian et al., (1989) J. Immunol. 142:3714-3725; Darrow et al., (1989) J. Immunol. 142:3329-3335; Horn et al., (1991) J. Immunother. 10:153-164; Kawakami et al., (1992) J. Immunol. 148:638-643; Horn et al., (1993) J. Immunother. 13:18-30; O'Neil et al., (1993) J. Immunol. 151:1410-1418). Tumor infiltrating lymphocytes (TILs) from patients with metastatic melanoma recognize shared antigens including melanocyte-melanoma lineage specific tissue antigens in vitro (See, e.g., Kawakami et al, (1993) J. Immunother. 14:88-93; Anichini et al., J. Exp. Med. 177: 989-998). Anti-melanoma T-cells appear to be enriched in TILs, (See, e.g., Sensi et al., (1993) J. Exp. Med. 178:1231-1246).

Development of molecular therapies for cancer have historically focused on specific recognition of antigens by cellular immune effectors. The present invention provides novel strategies comprising methods of vaccinating (e.g., prophylactically and/or therapeutically) a subject with nanoemulsion vaccine compositions.

T lymphocytes recognize antigen in the form of peptide fragments that are bound to class I and class II molecules of the major histocompatability complex (MHC) locus. Major Histocompatability Complex (MHC) is a generic designation meant to encompass the histocompatibility antigen systems described in different species including the human leucocyte antigens (HLA). The T-cell receptor (TCR) for antigen is a complex of at least 8 polypeptide chains. (See, e.g., Basic and Clinical Immunology (1994) Stites, Terr and Parslow (eds) Appleton and Lange, Nenmack Conn.). Two of these chains (the alpha and beta chains) form a disulfide-linked dimer that recognizes antigenic peptides bound to MHC molecules and therefore is the actual ligand-binding structure within the TCR. The TCR alpha and beta chains are similar in many respects to immunoglobulin proteins. The amino-terminal regions of the alpha and beta chains are highly polymorphic, so that within the entire T-cell population there are a large number of different TCR alpha/beta dimers, each capable of recognizing or binding a particular combination of antigenic peptide and MHC.

In general, CD4+ T cell populations are considered to function as helpers/inducers through the release of lymphokines/cytokines when stimulated by a specific antigen. However, a subset of CD4+ cells also act as cytotoxic T lymphocytes (CTL). Similarly, CD8+ T cells are considered to function by directly lysing antigenic targets; however, under a variety of circumstances they can secrete lymphokines/cytokines to provide helper or delayed type hypersensitivity function. Despite the potential of overlapping function, the phenotypic CD4 and CD8 markers are linked to the recognition of peptides bound to class II or class I MHC antigens, respectively. The recognition of antigen in the context of class II or class I MHC translates into CD4+ and CD8+ T cells responding to different antigens or the same antigen presented under different circumstances. CD4+ and CD8+ T cells have broadly different functions and tend to recognize different antigens as a reflection of where the antigens normally reside. For example, binding of immunogenic peptides to class II MHC antigens most commonly occurs for antigens ingested by antigen presenting cells. In contrast, under normal circumstances, binding of peptides to class I MHC occurs for proteins present in the cytosol and/or synthesized by the target itself (e.g., generally excluding proteins from the external (e.g., non-target cell) environment). One exception is the binding of exogenous peptides with a precise class I binding motif which are present outside the cell (e.g., in high concentration).

In general, during an immune response to a peptide, T cells expressing a T cell receptor with high affinity binding for the peptide-MHC complex will bind to the peptide-MHC complex and thereby become activated and induced to proliferate. In a first encounter with a peptide, small numbers of immune T cells secrete lymphokines/cytokines, proliferate and differentiate into effector and memory T cells. Subsequent encounters with the same immunogen by the memory T cell will lead to a faster and more intense immune response (e.g., faster and more robust expression of cytokines).

Thus, in some embodiments, a NE cancer vaccine of the invention comprises one or more protein components (e.g., peptides (e.g., that bind to MHC class I and/or class II molecules)). The protein components may comprise whole cell (e.g., cancer cell) lysates, a fractionated and/or purified form thereof, or other components. For example, the protein component may comprise recombinant protein and/or peptides. In some embodiments, the protein components may be obtained from cells (e.g., cancer cells) genetically modified to over-express one or more tumor associated antigens (TAAs). A variety of techniques are well known to those of ordinary skill in the art for isolating and/or constructing peptides. For example, antigen can be produced by recombinant technology (e.g., either as soluble molecules in eukaryotic systems or as fusion proteins in bacterial systems). In some embodiments, synthetic peptides are made from a tumor antigen. The present invention is not limited to any particular protein antigens. Indeed, a variety of protein antigens may find use in a vaccine of the present invention including, but not limited to, those described in Pietersz et al., 2000 Cell. Mol. Life. Sci. 57:290-310; Pardoll, 2000 Clin. Immunol 95 (1): S44-S62; Rosenberg, 2000 Cancer J. 6, Supp. 2: S142-S149; Dalgleish, 2000 Br. J. Cancer 82(10): 1619-1624, each of which is incorporated by reference herein).

In some embodiments, administration of a NE cancer vaccine of the present invention to a subject (e.g., human subject) induces expansion of T cells (e.g., involved in prophylactic and/or therapeutic attack against a tumor). In some embodiments, a vaccine formulation of the invention comprises components additional immunostimulatory substances designed to enhance immunogenicity (e.g., in addition to cancer cell lysates). Examples of immunostimulatory substances (adjuvants) include, but are not limited to, N-acetylmuramyl-L-alanine-D-isoglutamine (MDP), lipopoly-saccharides (LPS), glucan, IL-12, GM-CSF, IFN-, IL-15, and others described herein.

In some embodiments, compositions and methods of the present invention are utilized for inducing an immune response in a subject that has developed resistance to conventional cancer treatments and/or that has a high probability of developing a recurrence following treatment. Thus, in some embodiments, compositions and methods of the present invention prevent cancer cells from evading a subject's immune system and/or evading immune responses, prevent and/or decrease the ability of cancer/tumors to anergize a subject's host immune system, and/or prevent or decrease the ability of cancer/tumor to create an immunosuppressive environment (e.g., via secreting immunosuppressive factors and/or by expressing factors that induce apoptosis of an offensive tumor antigen-specific killer cell).

In some embodiments, the present invention provides nanoemulsion compositions (e.g., vaccines) and methods of using the same for the induction of immune responses (e.g., innate and adaptive immune responses (e.g., for generation of host immunity against a tumor)). A variety of nanoemulsions that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes).

Nanoemulsion cancer vaccines of the present invention may be formulated in any suitable manner and administered utilizing a variety of delivery methods. Any suitable pharmaceutical formulation may be utilized, including, but not limited to, those disclosed herein. Suitable formulations may be tested for immunogenicity using any suitable method. For example, in some embodiments, immunogenicity is investigated by quantitating specific T-cell responses and/or antibody titer. Nanoemulsion compositions of the present invention may also be tested in animal models (e.g., animal cancer, tumor, and/or metastatic models).

Although an understanding of the mechanism is not necessary to practice the present invention and the present invention is not limited to any particular mechanism of action, in some embodiments, NE cancer vaccines of the present invention preserve important antigenic epitopes (e.g., recognizable by a subject's immune system), stabilizing their hydrophobic and hydrophilic components in the oil and water interface of the emulsion (e.g., thereby providing one or more immunogens (e.g., stabilized antigens (e.g., tumor associated antigens (TAAs)) against which a subject's immune system can mount an immune response). In other embodiments, because NE formulations penetrate the mucosa (e.g., through pores) (See, e.g., Example 7), the vaccine formulations carry NE cancer vaccine components (e.g., cancer/tumor antigens and/or immunogens (e.g., TAAs) to submucosal locations (e.g., the sinus, submandibular lymph nodes, thymus, etc. (e.g., comprising dendritic cells (e.g., dendritic cells involved in initiating and/or stimulating an immune response)). Although an understanding of the mechanism is not necessary to practice the present invention and the present invention is not limited to any particular mechanism of action, in some embodiments, combining a NE and cells (e.g., cancer cells (e.g., lysed, UV irradiated, homogenized, genetically modified, etc.) and/or protein components (e.g., isolated and/or purified and/or recombinant protein from one or a plurality of cancer cells) stabilizes the cells and/or protein components and immunogenic portions thereof thereby providing a proper immunogenic material for generation of an immune response (e.g., an anti-cancer, anti-tumor, and/or anti-metastasis immune response).

Dendritic cells avidly phagocytose nanoemulsion (NE) oil droplets and this may, in some embodiments, provide a means to prime, enable and/or enhance an immune response (e.g., an anti-tumor immune response) toward a Th1 and/or Th2 type response, as well as to internalize immunogens (e.g., antigenic proteins or peptide fragments thereof present in the NE) for antigen presentation. While some vaccines rely on inflammatory toxins or other immune stimuli for adjuvant activity (See, e.g., Holmgren and Czerkinsky, Nature Med. 2005, 11; 45-53), NEs have not been shown to be inflammatory when placed on the skin or mucous membranes in studies on animals and in humans. Thus, although an understanding of the mechanism is not necessary to practice the present invention and the present invention is not limited to any particular mechanism of action, in some embodiments, a composition comprising a NE of the present invention (e.g., a composition comprising NE cancer vaccine) acts as a "physical" adjuvant (e.g., that transports and/or presents immunogens (e.g., TAAs) to the immune system. In some embodiments, mucosal administration of a composition of the present invention generates mucosal (e.g., signs of mucosal immunity (e.g., generation of IgA antibody titers)) as well as systemic immunity. In some embodiments, mucosal administration of a NE vaccine of the invention generates an innate immune response (e.g., activates Toll-like receptor signaling and/or activation of NF-kB) in a subject.

Both cellular and humoral immunity play a role in protection against abnormal cellular growth and both can be induced with the NE vaccine formulations of the present invention. Thus, in some embodiments, administration (e.g., mucosal administration) of a nanoemulsion vaccine of the present invention primes, enables and/or enhances induction of both humoral (e.g., development of specific antibodies) and cellular (e.g., cytotoxic T lymphocyte) immune responses (e.g., against a tumor and/or against cancer metastasis). In some embodiments, nanoemulsions described herein are utilized in a vaccine (e.g., a cancer vaccine (e.g., a prophylactic vaccine and/or a therapeutic vaccine). Thus, in some embodiments, the present invention provides NE cancer vaccines and methods of utilizing the same to prevent tumor metastasis. In some embodiments, the present invention provides NE cancer vaccines and methods of utilizing the same to skew a subject's immune response toward an anti-tumor immune response (e.g., toward a Th1 type immune response). In some embodiments, the present invention provides NE cancer vaccines and methods of utilizing the same to prime professional antigen presenting cells (APCs)(e.g., to present cancer associated antigens to a subject's immune system). In some embodiments, the present invention provides NE cancer vaccines and methods of utilizing the same to expand a subject's CD8+ cytotoxic T lymphocyte population (e.g., anti-cancer/tumor CD8+ cytotoxic T lymphocyte population). In some embodiments, the present invention provides NE cancer vaccines and methods of utilizing the same to expand a subject's CD4+ T cells (e.g., involved in generation of CD8+ anti-cancer memory cells). In some embodiments, the present invention provides NE cancer vaccines and methods of utilizing the same to suppress development of T regulatory cells (Tregs). In some embodiments, NE cancer vaccines provided herein are utilized as mucosal vaccine (e.g., for administration to the nasal mucosa).

Nanoemulsion Vaccine Formulations Elicit Anti-Tumor Immune Responses

The present invention provides a variety of nanoemulsion (e.g., $W_{80}5EC$, $P_{407}5EC$, etc.) compositions for use in cancer vaccine formulations (e.g., with no significant inflammation in animals and no evidence of the composition in the olfactory bulb). In some embodiments, the present invention provides compositions and methods for inducing immune responses (e.g., anti-cancer/tumor and/or anti-metastasis immune responses) utilizing administration (e.g., mucosal administration) of a NE vaccine (e.g., that induces mucosal and/or cellular immune responses (e.g., responses not elicited by injected, non-nanoemulsion adjuvant-based (e.g., aluminum-based) vaccines (See, e.g., Example 8)).

In some embodiments, the present invention provides methods of inducing an immune response and compositions useful in such methods (e.g., a nanoemulsion vaccine formulation). In some embodiments, methods of inducing an immune response in a host subject provided by the present invention are used for vaccination (e.g., prophylactic and/or therapeutic vaccination).

In some embodiments, a NE cancer vaccine of the invention comprises a NE and whole cancer cells (e.g., that have undergone freeze-thaw lysis (See, e.g., Examples 8 and 9)). In some embodiments, a NE cancer vaccine of the invention comprises a NE and homogenized cells (e.g., cancer cells (e.g., a cancer cell line or genetically modified cancer cells). In some embodiments, a NE cancer vaccine of the invention comprises a NE and cells (e.g., cancer cells (e.g., that have been exposed to UV radiation). In some embodiments, a NE cancer vaccine of the invention comprises a NE and a fraction or component of cancer cells (e.g., a fractionated cell lysis component). The present invention is not limited by the type of cancer cell utilized. Indeed, a variety of cancer cells may be used including, but not limited to, cells obtained from carcinoma, lymphoma, blastoma, sarcoma, or leukemia. In some embodiments, cancer cells are derived from squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma or various types of head and neck cancer. In some embodiments, cancer cells are harvested from subject, grown in vitro, and combined with NE. In some embodiments, cancer cells are genetically modified (e.g., transformed with an expression vector to express one or more protein antigens.

In some embodiments, a NE cancer vaccine of the invention comprises a NE and one or a plurality of tumor associated antigens. In some embodiments, a NE cancer vaccine of the invention comprises a NE and cells modified (e.g., genetically modified) to express (e.g., over-express) one or a plurality of tumor associated antigens. In some embodiments, one or a plurality of protein components (e.g., isolated and/or purified and/or recombinant protein) from one or a plurality of cancer cells are mixed with NE and utilized to induce an immune response in a subject. In some embodiments, a NE cancer vaccine of the invention comprises one or more adjuvants (e.g., a nanoemulsion adjuvant and/or non-nanoemulsion adjuvant). In some embodiments the present invention provides methods of administering cancer vaccines (e.g., nasally administering) to a subject under conditions such that the subject generates an immune response to the cancer and/or tumor components of the vaccine (See, e.g., Examples 8 and 9). In some embodiments, administrating comprises mucosal administration. In some embodiments, inducing an immune response induces immunity to one or a plurality of cancer antigens in the subject. In some embodiments, inducing an immune response to the cancer antigens induces immunity to the cancer and/or tumor from which the antigens are derived. In some embodiments, immunity comprises systemic immunity. In some embodiments, immunity comprises mucosal immunity. In some embodiments, immunity comprises reduction and/or elimination of tumor metastasis in an immunized subject. In some embodiments, the immune response comprises increased expression of IFN—in the subject. In some embodiments, the immune response comprises a systemic IgG response to the immunogens (e.g., comparable to monovalent vaccine formulations). In some embodiments, the immune response comprises a mucosal IgA response to the immunogens. In some embodiments, the immune response is characterized by a balanced Th1/Th2 polarization (e.g., an IgG subclass distribution and cytokine response indicative of a balanced Th1/Th2 response). Although an understanding of the mechanism is not necessary to practice the invention and the invention is not limited to any particular mechanism of action, in some embodiments, an immunogenic composition comprising a nanoemulsion and a cancer immunogen elicits an immune response distinct from an immune response elicited independently by a cancer immunogen or by the cancer immunogen in the presence of a non-nanoemulsion substance (e.g., a non-nanoemulsion adjuvant). In some embodiments, a cancer immunogen in the presence of a nanoemulsion elicits an immune response (e.g., an adaptive immune response (e.g., comprising generation of anti-cancer antibodies)) that prevents metastasis of cancer.

Thus, in some embodiments, the present invention provides immunogenic compositions that elicit an immune response by the host (e.g., host cells) to which it is administered (e.g., including the production of cytokines and other immune factors). In some embodiments, an vaccine composition is formulated to include at least one antigen. An antigen may be an protein or polypeptide or an antigenic fraction thereof. An antigenic fraction can be produced by means of chemical or physical decomposition methods, followed, if desired, by separation of a fraction by means of chromatography, centrifugation and similar techniques. Alternatively, antigens or haptens can be prepared by means of organic synthetic methods, or, in the case of, for example, polypeptides and proteins, by means of recombinant DNA methods.

In some embodiments, the present invention demonstrates that specific nanoemulsion adjuvants (e.g., $W_{80}5EC$) possess the ability to alter expression of genes associated with certain types of immune responses while other forms of nanoemulsion adjuvant do not. Accordingly, in some embodiments, the present invention provides a method of inducing an immune response in a subject comprising administering to a subject a composition comprising a nanoemulsion vaccine under conditions such that the expression of one or more genes associated with an immune response (e.g., a Th1 type immune response and/or a Th2 type immune response) is altered (e.g., enhances or reduced) in the subject (e.g., within dendritic cells (e.g., eliciting and/or augmenting an anti-cancer (e.g., anti-tumor and/or anti-metastasis) immune response in a subject)).

In some embodiments, the present invention provides nanoemulsion compositions that stimulate and/or elicit immune responses (e.g., innate immune responses) when administered to a subject (e.g., a human subject)).

The innate immune response enables a host to differentiate self from non-self and provide a rapid inflammatory response, including production of cytokines and chemokines, elaboration of effector molecules, such as NO, and interactions with the adaptive immune response (See, e.g., Janeway and Medzhitov, (2002) Annu. Rev. Immunol. 20, 197-216). Molecular understanding of innate immunity in humans evolved the mid-1990s when the *Drosophila* protein Toll was shown to be critical for defending flies against fungal infections (See, e.g., Lemaitre et al., (1996). Cell 86, 973-983). The human Toll-like receptor (TLR) family includes at least ten receptors that play important roles in innate immunity (See, e.g., Akira et al., (2006) Cell 124, 783-801; Beutler et al., (2006) Annu. Rev. Immunol 24, 353-380; and Takeda et al., (2003). Annu. Rev. Immunol. 21, 335-376).

In general, TLRs recognize and respond to diverse non-self (e.g., microbial) molecules and enable the innate immune system to discriminate among groups of non-self materials and to induce an appropriate cascade of effector responses. Individual TLRs recognize a distinct repertoire of conserved molecules (e.g., microbial products). For example, well-characterized receptor-ligand pairs include TLR4 and LPS (lipopolysaccharide), TLR5 and flagellin, TLR1/TLR2/TLR6 and lipoproteins, and TLR3/TLR7/TLR8/TLR9 and different nucleic acid motifs. Collectively, the family of TLRs allows a host's innate immune system to detect the presence of foreign, non-self molecules (e.g., microbial products of most microbial pathogens or other substances).

Figure 5:
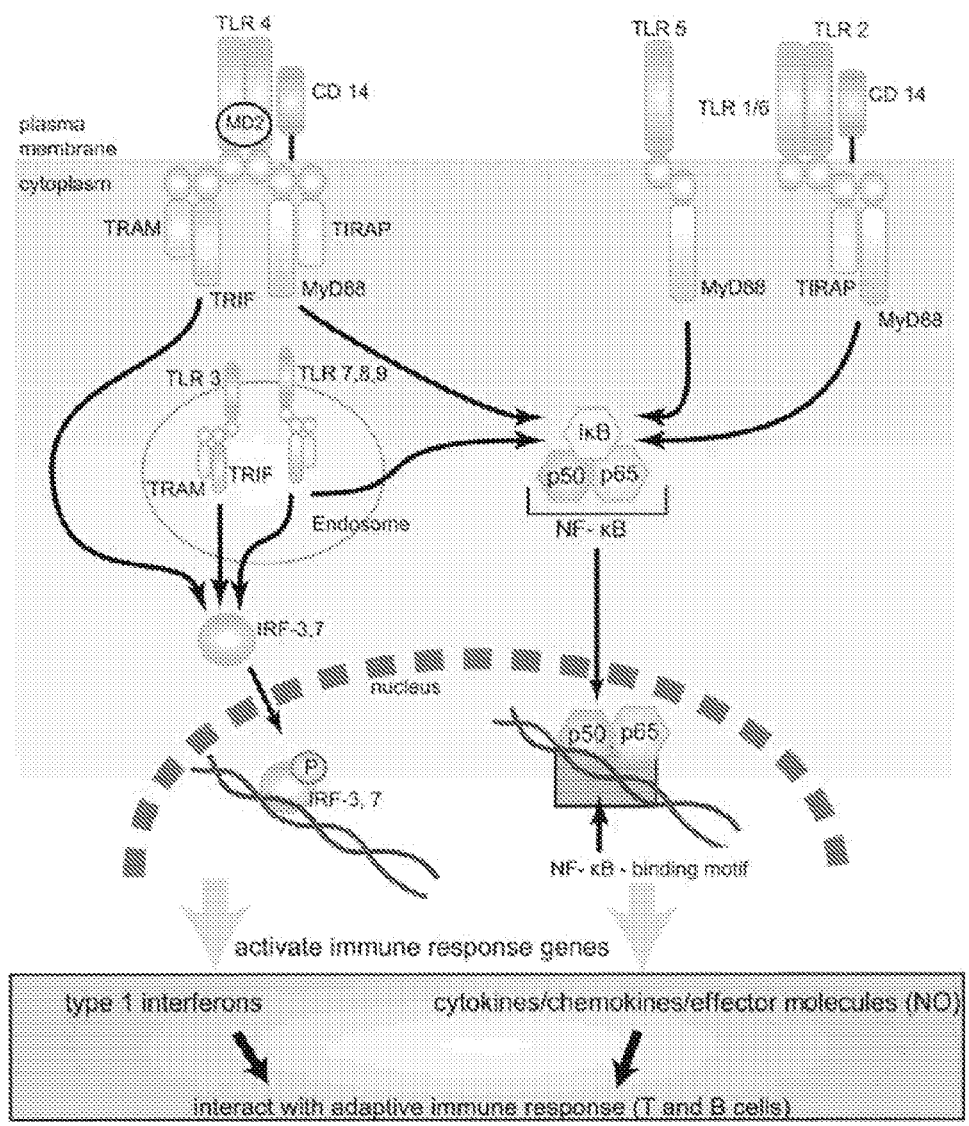
FIG. 5 provides a diagram depicting TLRs trigger a complex cascade of events that lead to the induction of a range of proinflammatory genes.
Figure 6:
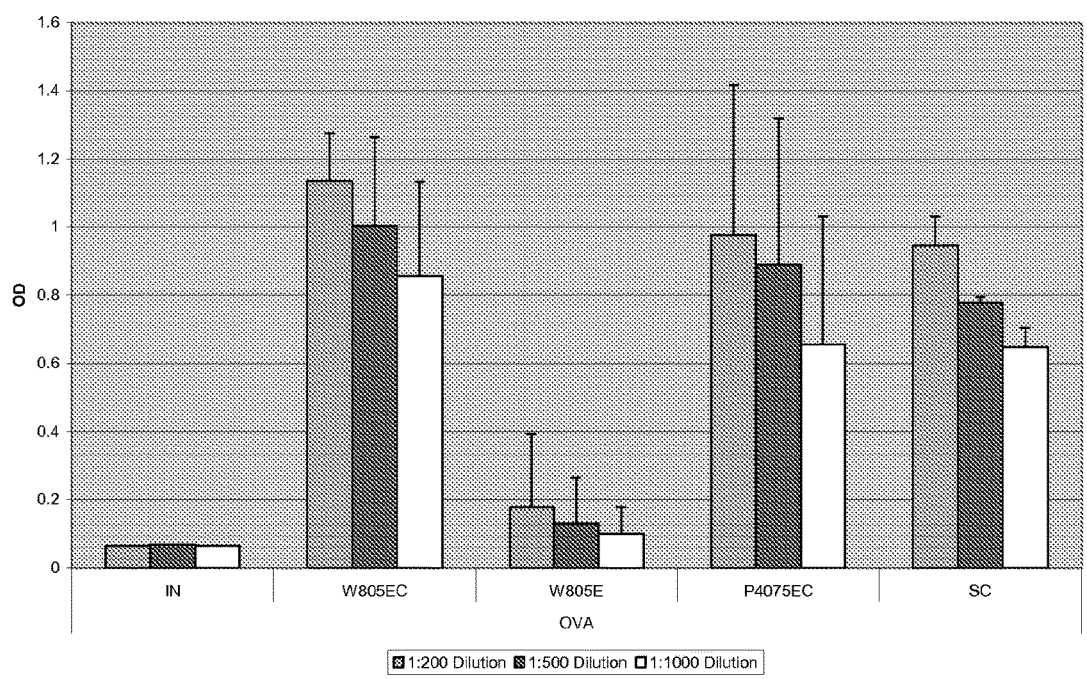
FIG. 6 provides mouse serum IgG levels at 9 weeks post intranasal administration of OVA in W805EC, W805E or P4075EC, and controls.
Figure 7:
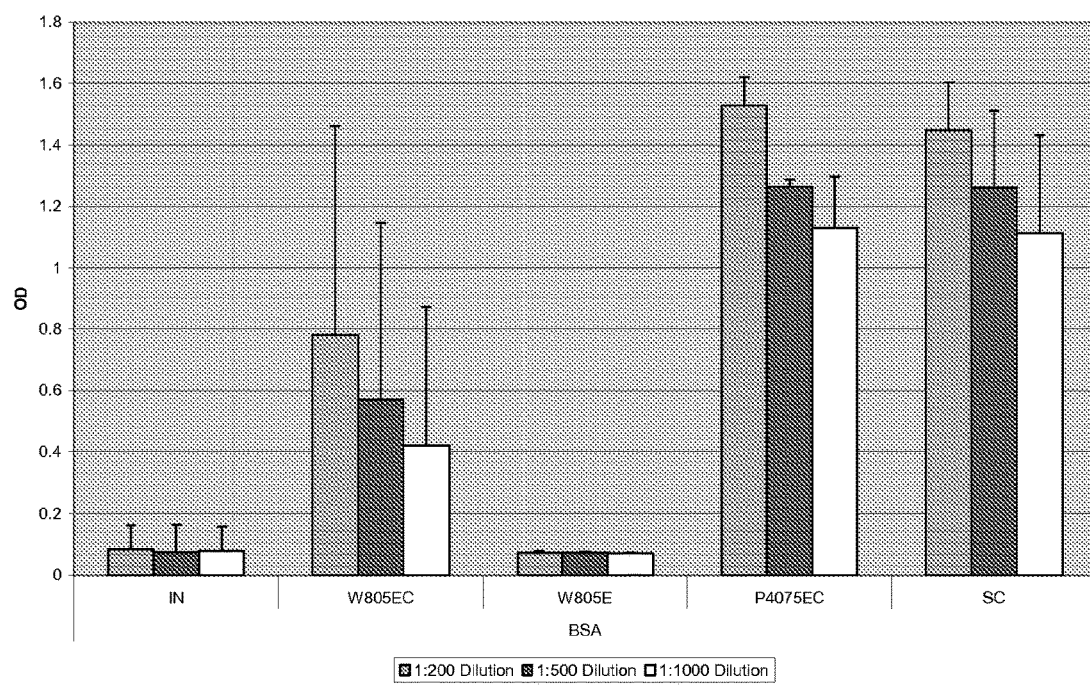
FIG. 7 provides mouse serum IgG levels at 9 weeks post intranasal administration of BSA in W805EC, W805E or P4075EC, and controls.
Figure 8:
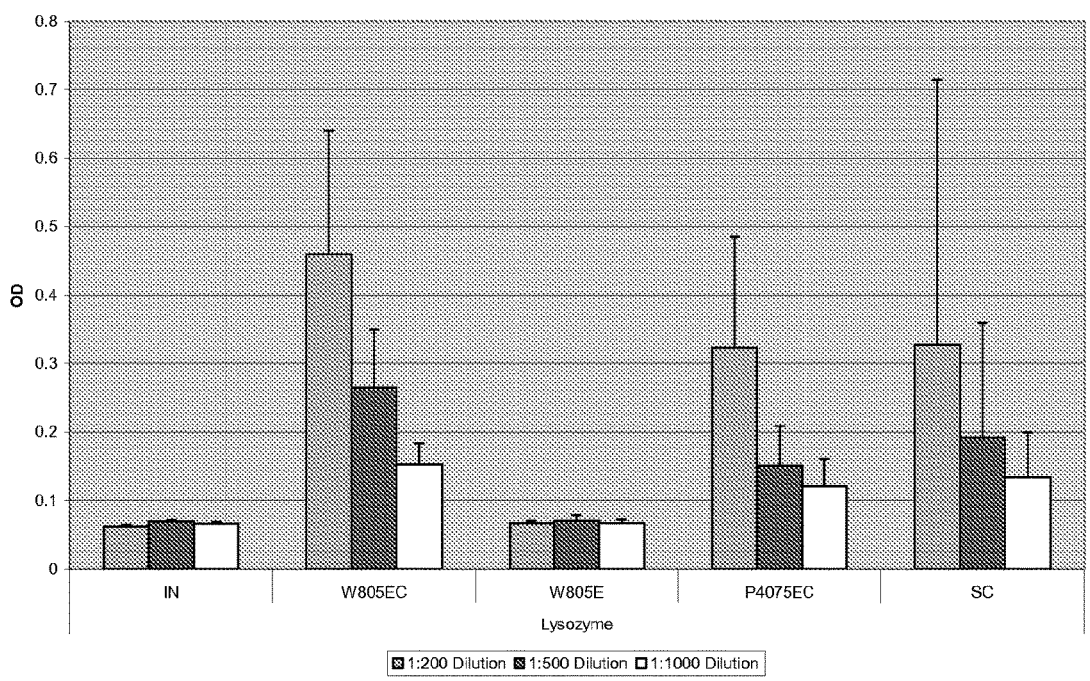
FIG. 8 provides mouse serum IgG levels at 2 weeks post intranasal administration of lysozyme in W805EC, W805E or P4075EC, and controls.

TLRs are classified as members of the IL-1R (IL-1 receptor) superfamily on the basis of a shared cytoplasmic region known as the TIR (Toll/IL-1R) domain. The extracellular portions of TLRs are rather diverse, comprising varying numbers of leucine-rich repeats. Following encounter with a microbe, TLRs trigger a complex cascade of events that lead to the induction of a range of proinflammatory genes (See, e.g., Yamamoto et al., (2002) Nature 420, 324-329 (See, e.g., Misch and Hawn, Clin Sci 2008, 114, 347-360, and also FIG. 5)). Ligand binding results in the recruitment of several molecules to the receptor complex. These include TIR-domain-containing adaptor molecules such as MyD88 (myeloid differentiation primary response gene 88), TIRAP/Mal (TIR-domain-containing adapter/MyD88 adaptor-like), TICAM1/TRIF (TIR-domain-containing adaptor molecule 1/TIR-domain-containing adaptor-inducing interferon b) and TRAM (TRIF-related adaptor molecule). Further recruitment of molecules includes IRAKs (IL-1R-associated kinases (IRAK1, 2, 3 (M) and 4)) as well as TRAF6 (TNF receptor-associated factor 6). IRAK1 and TRAF6 then dissociate and bind another complex that comprises TAK1 (TGF (transforming growth factor)-b-activated kinase 1) and TAB1, 2 and 3 (TAK-1-binding proteins 1, 2 and 3). TAK1 then activates IKK (IkB (inhibitor of NF-kB (nuclear factor kB)) kinase). The activity of this complex is regulated by IKKg [also known as NEMO (NF-kB essential modulator)]. IKK-mediated phosphorylation of IkB leads to its degradation, allowing NF-kB to translocate to the nucleus and promote the transcription of multiple proinflammatory genes, including TNF, IL-1b and IL-6.

TLR activation by pathogens, or by molecules derived therefrom, induces intracellular signaling that primarily results in activation of the transcription factor NF-kB (See, e.g., Beg, 2002, Trends Immunol. 2002 23 509-12.) and modulation of cytokine production. However, a series of other pathways can also be triggered, including p38 mitogen activated kinase, c-Jun-N-terminal kinase and extracellular signal related kinase pathways (See, e.g., Flohe, et al., 2003, J Immunol, 170 2340-2348; Triantafilou & Triantafilou, 2002, Trends Immunol, 23 301-304). The patterns of gene expression induced by ligation of the different TLRs are distinct but often overlap. For instance a large proportion of the genes upregulated by TLR3 agonists and double stranded RNA are also upregulated by TLR4 agonists and LPS (See, e.g., Doyle et al., 2002, Immunity, 17 251-263). TLR4 activation by LPS in macrophages results in TNF-α, IL-12 IL-1β, RANTES and MIP1β secretion (See, e.g., Flohe et al., supra; Jones et al., 2002, J Leukoc Biol, 69 1036-1044).

In some embodiments, the present invention provides that positively charged nanoemulsions (e.g., comprising a positive surface charge (e.g., due to the presence of a cationic compound (e.g., CPC))) possess greater efficacy at eliciting immune responses (e.g., innate immune responses and/or adaptive/acquired immune responses) than nanoemulsion adjuvants lacking a positive charge (e.g., lacking a positive surface charge (e.g., due to the absence of a cationic compound (e.g., CPC))) (See, e.g., Example 5). Although an understanding of a mechanism is not necessary to practice the present invention, and the present invention is not limited to any particular mechanism of action, in some embodiments, a nanoemulsion adjuvant possessing a positive charge (e.g., a positive surface charge (e.g., due to the presence of a cationic compound in the nanoemulsion (e.g., CPC))) possesses greater adhesion to mucosa (e.g., when administered intranasally) than non-positively charged emulsions (e.g., due to the positively charged surface of the emulsion). In some embodiments, a nanoemulsion adjuvant possessing a positive charge (e.g., a positive surface charge (e.g., due to the presence of a cationic compound in the nanoemulsion (e.g., CPC))) is more readily internalized by phagocytic cells (e.g., macrophages, dendritic cells, B cells, etc.) or other cells than is a non-positively charged nanoemulsion (e.g., leading to greater internalization of antigen (e.g., by antigen presenting cells), processing of antigen, and/or presentation of antigen to B and/or T cells). Thus, in some embodiments, greater internalization and/or processing of antigen and/or presentation of antigen to B and/or T cells leads to a stronger, more robust immune responses (e.g., to an antigen administered in a nanoemulsion possessing a positive charge (e.g., a positive surface charge (e.g., due to the presence of a cationic compound in the nanoemulsion (e.g., CPC))).

In some embodiments, a nanoemulsion of the invention is utilized to stimulate and/or elicit host innate immune responses (e.g., enhanced NF-kB activity and/or activation of Toll-like receptor (TLR) signaling) (See, e.g., Example 6). For example, as described herein, the present invention provides nanoemulsions comprising a polysorbate detergent that display the ability to induce signaling via TLRs (e.g., TLR2 and TLR4 (See FIG. 11)). Although an understanding of a mechanism is not necessary to practice the present invention, and the present invention is not limited to any particular mechanism of action, in some embodiments, nanoemulsions provided herein activate NF-κB response by stimulation of TLRs (e.g., TLR2 and TLR4). Thus, in some embodiments, the present invention provides nanoemulsions (e.g., possessing a positive charge (e.g., a positive surface charge (e.g., due to the presence of a cationic compound in the nanoemulsion (e.g., CPC))) that are utilized to increase mucosal adhesion and internalization (e.g., by dendritic cells) and/or that are utilized to induce innate immune responses (e.g., TLR signaling, activation of NF-kB and expression of cytokines) in a host subject. The present invention is not limited to any particular polysorbate detergent. Indeed, a variety of polysorbates may be utilized in a nanoemulsion adjuvant including, but not limited to, TWEEN 20, TWEEN 40, TWEEN 60, TWEEN 80, etc.

Thus, in some embodiments, the present invention provides adjuvants that reduce the number of booster injections required to achieve protection. In some embodiments, the present invention provides nanoemulsions that result in a higher proportion of recipients achieving seroconversion. In some embodiments, the present invention provides nanoemulsions that are useful (e.g., in the context of a cancer vaccine) for selectively skewing adaptive immunity toward Th1, Th2, or cytotoxic T cell responses (e.g., allowing effective immunization by distinct routes (e.g., such as via the skin or mucosa)). In some embodiments, the present invention provides nanoemulsions that elicit optimal responses in very young and/or very old populations (e.g., in whom most contemporary vaccination strategies are not optimally effective). In some embodiments, the present invention provides nanoemulsions that provide efficacy and safety needed for vaccination regimens that involve different delivery routes and elicitation of distinct types of immunity. In some embodiments, the present invention provides nanoemulsions that stimulate antibody responses and have little toxicity and that can be utilized with a range of antigens (e.g., cancer antigens (e.g., cancer cells, cancer cell fractions, tumor associated antigens, etc.) for which they provide adjuvanticity and the types of immune responses they elicit. In some embodiments, the present invention provides nanoemulsions that meet global supply requirements (e.g., in response to increased incidence of cancer (e.g., among an aging population)).

Vaccines containing peptides are generally known in the art, as exemplified by U.S. Pat. Nos. 4,601,903; 4,599,231; 4,599,230; and 4,596,792; each of which is hereby incorporated by reference.

The use of peptides in vivo may first require their chemical modification since the peptides themselves may not have a sufficiently long serum and/or tissue half-life and/or sufficient immunogenicity. For this purpose, the antigens/immunogens of the invention may optionally be linked to a carrier molecule. Many suitable linkages are known, e.g., using the side chains of Tyr residues. Suitable carriers include, e.g., keyhole limpet hemocyanin (KLH), serum albumin, purified protein derivative of tuberculin (PPD), ovalbumin, non-protein carriers (e.g., conjugation to one or more polysaccharides), and many others.

In addition, it may be advantageous to modify antigens/immunogens in order to impose a conformational restraint upon them. This might be useful, for example, to mimic a naturally-occurring conformation of the antigen/immunogen in the context of the native protein in order to optimize the effector immune responses that are elicited. One example of an antigen/immunogen that can be modified is a peptide.

Modified peptides are referred to herein as "peptide analogs". The term "peptide analog" extends to any functional chemical equivalent of a peptide characterized by its increased stability and/or efficacy and immunogenicity in vivo or in vitro in respect of the practice of the invention. The term "peptide analog" is also used herein to extend to any amino acid derivative of the peptides as described herein. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

It will be apparent that the peptides employed herein as antigens can be modified in a variety of different ways without significantly affecting the functionally important immunogenic behavior thereof. Possible modifications to the peptide sequence may include the following: One or more individual amino acids can be substituted by amino acids having comparable or similar properties, thus: V may be substituted by I; T may be substituted by S; K may be substituted by R; or L may be substituted by I, V or M. One or more of the amino acids of peptides of the invention can be replaced by a "retro-inverso" amino acid, i.e., a bifunctional amine having a functional group corresponding to an amino acid, as discussed in published International application WO 91/13909. One or more amino acids can be deleted. Structural analogs mimicking the 3-dimensional structure of the peptide can be used in place of the peptide.

Examples of side chain modifications contemplated by the present invention include modification of amino groups, such as by reductive alkylation by reaction with an aldehyde followed by reduction with $NaBH_4$; amidation with methylacetimidate; acetylation with acetic anhydride; carbamylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents, such as 2,3-butanedione, phenylglyoxal and glyoxal. The carboxyl group may be modified by carbodiimide activation via o-acylisourea formation followed by subsequent derivatisation, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Nanoemulsions

The present invention is not limited by the type of nanoemulsion utilized (e.g., in a cancer vaccine formulation (e.g., for mucosal administration)). Indeed, a variety of nanoemulsions are contemplated to be useful in the present invention.

The term "nanoemulsion", as defined herein, refers to a dispersion or droplet or any other lipid structure. Typical lipid structures contemplated in the invention include, but are not limited to, unilamellar, paucilamellar and multilamellar lipid vesicles, micelles and lamellar phases.

The nanoemulsion of the present invention comprises droplets having an average diameter size of less than about 1,000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, or any combination thereof. In one embodiment, the droplets have an average diameter size greater than about 125 nm and less than or equal to about 300 nm. In a different embodiment, the droplets have an average diameter size greater than about 50 nm or greater than about 70 nm, and less than or equal to about 125 nm. In other embodiments of the invention, the nanoemulsion droplets have an average diameter of from about 300 nm to about 600 nm; or the nanoemulsion droplets have an average diameter of from about 150 nm to about 400 nm.

In some embodiments, a nanoemulsion comprises (i) an aqueous phase; and (ii) an oil phase. In some embodiments, a nanoemulsion comprises (i) an aqueous phase; (ii) an oil phase; and (iii) at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in a nanoemulsion of the present invention include, but are not limited to, one or more organic, and more particularly, organic phosphate based solvents, surfactants and detergents, cationic halogen containing compounds, germination enhancers, interaction enhancers, food additives (e.g., flavorings, sweeteners, bulking agents, and the like) and pharmaceutically acceptable compounds. Certain exemplary embodiments of the various compounds contemplated for use in the compositions of the present invention are presented below. Unless described otherwise, nanoemulsions are described in undiluted form.

In one embodiment of the invention, the nanoemulsion comprises: (a) an aqueous phase; (b) about 1% oil to about 80% oil; (c) about 0.1% organic solvent to about 50% organic solvent; (d) about 0.001% surfactant or detergent to about 10% surfactant or detergent; (e) about 0.0005% to about 1.0% of a chelating agent; or (e) any combination thereof. In another embodiment of the invention, the nanoemulsion comprises: (a) about 10% oil to about 80% oil; (b) about 1% organic solvent to about 50% organic solvent; (c) at least one non-ionic surfactant present in an amount of about 0.1% to about 10%; (d) at least one cationic agent present in an amount of about 0.01% to about 3%; or any combination thereof.

In another embodiment, the nanoemulsion comprises a cationic surfactant which is either cetylpyridinium chloride (CPC) or benzalkonium chloride, or alkyl dimethyl benzyl ammonium chloride (BTC 824), or combination thereof. The cationic surfactant may have a concentration in the nanoemulsion of less than about 5.0% and greater than about 0.001%, or further, may have a concentration of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, and greater than about 0.010%.

In a further embodiment, the nanoemulsion comprises a non-ionic surfactant, and may have a concentration of about 0.01% to about 10.0%, or about 0.1% to about 3% of a non-ionic surfactant, such as a polysorbate.

In yet other embodiments of the invention, the nanoemulsion: (a) comprises at least one cationic surfactant; (b) comprises a cationic surfactant which is either cetylpyridinium chloride or benzalkonium chloride, or alkyl dimethyl benzyl ammonium chloride (BTC 824), or combination thereof; (c) comprises a cationic surfactant, and wherein the concentration of the cationic surfactant is less than about 5.0% and greater than about 0.001%; (d) comprises a cationic surfactant, and wherein the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, and greater than about 0.010%; or (e) any combination thereof. In yet other embodiments, (a) the nanoemulsion comprises at least one cationic surfactant and at least one non-cationic surfactant; (b) the nanoemulsion comprises at least one cationic surfactant and at least one non-cationic surfactant, wherein the non-cationic surfactant is a nonionic surfactant; (c) the nanoemulsion comprises at least one cationic surfactant and at least one non-cationic surfactant, wherein the non-cationic surfactant is a polysorbate nonionic surfactant; (d) the nanoemulsion comprises at least one cationic surfactant and at least one non-cationic surfactant, wherein the non-cationic surfactant is a nonionic surfactant, and the non-ionic surfactant is present in a concentration of about 0.05% to about 10%, about 0.05% to about 7.0%, about 0.1% to about 7%, or about 0.5% to about 5%; (e) the nanoemulsion comprises at least one cationic surfactant and at least one a nonionic surfactant, wherein the cationic surfactant is present in a concentration of about 0.05% to about 2% or about 0.01% to about 2%; or (f) any combination thereof.

In other embodiments, the nanoemulsion comprises: (a) water; (b) ethanol or glycerol (glycerine), or a combination thereof; (c) either cetylpyridinium chloride (CPC), or benzalkonium chloride, or alkyl dimethyl benzyl ammonium chloride (BTC 824), or a combination thereof; (c) soybean oil; and (e) Poloxamer 407, Tween 80, or Tween 20. The nanoemulsion can further comprise EDTA.

These quantities of each component present in the nanoemulsion refer to a therapeutic nanoemulsion, and not to a nanoemulsion to be tested in vitro. This is significant, as nanoemulsions tested in vitro generally have lower concentrations of oil, organic solvent, surfactant or detergent, and (if present) chelating agent than that present in a nanoemulsion intended for therapeutic use, e.g., topical use. This is because in vitro studies do not require the nanoemulsion droplets to traverse the skin. For topical, aerosol, intradermal etc. use, the concentrations of the components must be higher to result in a therapeutic nanoemulsion. However, the relative quantities of each component used in a nanoemulsion tested in vitro are applicable to a nanoemulsion to be used therapeutically and, therefore, in vitro quantities can be scaled up to prepare a therapeutic composition, and in vitro data is predictive of topical application success.

1. Aqueous Phase

The aqueous phase can comprise any type of aqueous phase including, but not limited to, water (e.g., $H_2O$, distilled water, tap water) and solutions (e.g., phosphate buffered saline (PBS) solution). In certain embodiments, the aqueous phase comprises water at a pH of about 4 to 10, preferably about 6 to 8. The water can be deionized (hereinafter "$DiH_2O$"). In some embodiments the aqueous phase comprises phosphate buffered saline (PBS). The aqueous phase may further be sterile and pyrogen free.

2. Organic Solvents

Organic solvents in the nanoemulsions of the invention include, but are not limited to, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the invention, the organic solvent is an alcohol chosen from a nonpolar solvent, a polar solvent, a protic solvent, or an aprotic solvent.

Suitable organic solvents for the nanoemulsion include, but are not limited to, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof.

3. Oil Phase

The oil in the nanoemulsion of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (simmondsia chinensis seed oil), Grapeseed oil, *Macadamia* oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, *cassia* Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, *chenopodium* oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

4. Surfactants/Detergents

The surfactant or detergent in the nanoemulsion of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference.

Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a nonpolar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thighlycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl disterate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23.

In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N—N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis (imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl (tetradecyl)ammonium bromide, 1,3,5-Triazine-1,3,5(2H, 4H,6H)-triethanol, 1-Decanaminium, N-decyl-N,N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy) ethyl dimethyl benzyl ammonium chloride, Alkyl 1 or 3 benzyl-1-(2-hydroxethyl)-2-imidazolinium chloride, Alkyl bis(2-hydroxyethyl) benzyl ammonium chloride, Alkyl demethyl benzyl ammonium chloride, Alkyl dimethyl 3,4-dichlorobenzyl ammonium chloride (100% C12), Alkyl dimethyl 3,4-dichlorobenzyl ammonium chloride (50% C14, 40% C12, 10% C16), Alkyl dimethyl 3,4-dichlorobenzyl ammonium chloride (55% C14, 23% C12, 20% C16), Alkyl dimethyl benzyl ammonium chloride, Alkyl dimethyl benzyl ammonium chloride (100% C14), Alkyl dimethyl benzyl ammonium chloride (100% C16), Alkyl dimethyl benzyl ammonium chloride (41% C14, 28% C12), Alkyl dimethyl benzyl ammonium chloride (47% C12, 18% C14), Alkyl dimethyl benzyl ammonium chloride (55% C16, 20% C14), Alkyl dimethyl benzyl ammonium chloride (58% C14, 28% C16), Alkyl dimethyl benzyl ammonium chloride (60% C14, 25% C12), Alkyl dimethyl benzyl ammonium chloride (61% C11, 23% C14), Alkyl dimethyl benzyl ammonium chloride (61% C12, 23% C14), Alkyl dimethyl benzyl ammonium chloride (65% C12, 25% C14), Alkyl dimethyl benzyl ammonium chloride (67% C12, 24% C14), Alkyl dimethyl benzyl ammonium chloride (67% C12, 25% C14), Alkyl dimethyl benzyl ammonium chloride (90% C14, 5% C12), Alkyl dimethyl benzyl ammonium chloride (93% C14, 4% C12), Alkyl dimethyl benzyl ammonium chloride (95% C16, 5% C18), Alkyl didecyl dimethyl ammonium chloride, Alkyl dimethyl benzyl ammonium chloride (C12-16), Alkyl dimethyl benzyl ammonium chloride (C12-18), dialkyl dimethyl benzyl ammonium chloride, Alkyl dimethyl dimethybenzyl ammonium chloride, Alkyl dimethyl ethyl ammonium bromide (90% C14, 5% C16, 5% C12), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% C14), Alkyl dimethyl isopropylbenzyl ammonium chloride (50% C12, 30% C14, 17% C16, 3% C18), Alkyl trimethyl ammonium chloride (58% C18, 40% C16, 1% C14, 1% C12), Alkyl trimethyl ammonium chloride (90% C18, 10% C16), Alkyldimethyl(ethylbenzyl) ammonium chloride (C12-18), Di-(C8-10)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis(2-hydroxyethyl) octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with a particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4,1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio) propanesulfonate inner salt, 3-(N,N-Dimethylpalmitylammonio)propanesulfonate, semi-synthetic derivatives thereof, and combinations thereof.

In some embodiments, the nanoemulsion comprises a cationic surfactant, which can be cetylpyridinium chloride. In other embodiments of the invention, the nanoemulsion comprises a cationic surfactant, and the concentration of the cationic surfactant is less than about 5.0% and greater than about 0.001%. In yet another embodiment of the invention, the nanoemulsion comprises a cationic surfactant, and the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, or less than about 0.10%. Further, the concentration of the cationic agent in the nanoemulsion is greater than about 0.002%, greater than about 0.003%, greater than about 0.004%, greater than about 0.005%, greater than about 0.006%, greater than about 0.007%, greater than about 0.008%, greater than about 0.009%, greater than about 0.010%, or greater than about 0.001%. In one embodiment, the concentration of the cationic agent in the nanoemulsion is less than about 5.0% and greater than about 0.001%.

In another embodiment of the invention, the nanoemulsion comprises at least one cationic surfactant and at least one non-cationic surfactant. The non-cationic surfactant is a nonionic surfactant, such as a polysorbate (Tween), such as polysorbate 80 or polysorbate 20. In one embodiment, the non-ionic surfactant is present in a concentration of about 0.05% to about 7.0%, or the non-ionic surfactant is present in a concentration of about 0.5% to about 4%. In yet another embodiment of the invention, the nanoemulsion comprises a cationic surfactant present in a concentration of about 0.01% to about 2%, in combination with a nonionic surfactant.

5. Additional Ingredients

Additional compounds suitable for use in the nanoemulsions of the invention include but are not limited to one or more solvents, such as an organic phosphate-based solvent, bulking agents, coloring agents, pharmaceutically acceptable excipients, a preservative, pH adjuster, buffer, chelating agent, etc. The additional compounds can be admixed into a previously emulsified nanoemulsion, or the additional compounds can be added to the original mixture to be emulsified. In certain of these embodiments, one or more additional compounds are admixed into an existing nanoemulsion composition immediately prior to its use.

Suitable preservatives in the nanoemulsions of the invention include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis(p-chlorophenyldiguanido) hexane), chlorphenesin (3-(-4-chlorophenoxy) propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

The nanoemulsion may further comprise at least one pH adjuster. Suitable pH adjusters in the nanoemulsion of the invention include, but are not limited to, diethyanolamine, lactic acid, monoethanolamine, triethylanolamine, sodium hydroxide, sodium phosphate, semi-synthetic derivatives thereof, and combinations thereof.

In addition, the nanoemulsion can comprise a chelating agent. In one embodiment of the invention, the chelating agent is present in an amount of about 0.0005% to about 1.0%. Examples of chelating agents include, but are not limited to, phytic acid, polyphosphoric acid, citric acid, gluconic acid, acetic acid, lactic acid, ethylenediamine, ethylenediaminetetraacetic acid (EDTA), and dimercaprol, and a preferred chelating agent is ethylenediaminetetraacetic acid.

The nanoemulsion can comprise a buffering agent, such as a pharmaceutically acceptable buffering agent. Examples of buffering agents include, but are not limited to, 2-Amino-2-methyl-1,3-propanediol, ≥99.5% (NT), 2-Amino-2-methyl-1-propanol, ≥99.0% (GC), L-(+)-Tartaric acid, ≥99.5% (T), ACES, ≥99.5% (T), ADA, ≥99.0% (T), Acetic acid, ≥99.5% (GC/T), Acetic acid, for luminescence, ≥99.5% (GC/T), Ammonium acetate solution, for molecular biology, ~5 M in $H_2O$, Ammonium acetate, for luminescence, ≥99.0% (calc. on dry substance, T), Ammonium bicarbonate, ≥99.5% (T), Ammonium citrate dibasic, ≥99.0% (T), Ammonium formate solution, 10 M in $H_2O$, Ammonium formate, ≥99.0% (calc. based on dry substance, NT), Ammonium oxalate monohydrate, ≥99.5% (RT), Ammonium phosphate dibasic solution, 2.5 M in $H_2O$, Ammonium phosphate dibasic, ≥99.0% (T), Ammonium phosphate monobasic solution, 2.5 M in $H_2O$, Ammonium phosphate monobasic, ≥99.5% (T), Ammonium sodium phosphate dibasic tetrahydrate, ≥99.5% (NT), Ammonium sulfate solution, for molecular biology, 3.2 M in $H_2O$, Ammonium tartrate dibasic solution, 2 M in $H_2O$ (colorless solution at 20° C.), Ammonium tartrate dibasic, ≥99.5% (T), BES buffered saline, for molecular biology, 2× concentrate, BES, ≥99.5% (T), BES, for molecular biology, ≥99.5% (T), BICINE buffer Solution, for molecular biology, 1 M in $H_2O$, BICINE, ≥99.5% (T), BIS-TRIS, ≥99.0% (NT), Bicarbonate buffer solution, >0.1 M $Na_2CO_3$, >0.2 M $NaHCO_3$, Boric acid, ≥99.5% (T), Boric acid, for molecular biology, ≥99.5% (T), CAPS, ≥99.0% (TLC), CHES, ≥99.5% (T), Calcium acetate hydrate, ≥99.0% (calc. on dried material, KT), Calcium carbonate, precipitated, ≥99.0% (KT), Calcium citrate tribasic tetrahydrate, ≥98.0% (calc. on dry substance, KT), Citrate Concentrated Solution, for molecular biology, 1 M in $H_2O$, Citric acid, anhydrous, ≥99.5% (T), Citric acid, for luminescence, anhydrous, ≥99.5% (T), Diethanolamine, ≥99.5% (GC), EPPS, ≥99.0% (T), Ethylenediaminetetraacetic acid disodium salt dihydrate, for molecular biology, ≥99.0% (T), Formic acid solution, 1.0 M in $H_2O$, Gly-Gly-Gly, ≥99.0% (NT), Gly-Gly, ≥99.5% (NT), Glycine, ≥99.0% (NT), Glycine, for luminescence, ≥99.0% (NT), Glycine, for molecular biology, ≥99.0% (NT), HEPES buffered saline, for molecular biology, 2× concentrate, HEPES, ≥99.5% (T), HEPES, for molecular biology, ≥99.5% (T), Imidazole buffer Solution, 1 M in $H_2O$, Imidazole, ≥99.5% (GC), Imidazole, for luminescence, ≥99.5% (GC), Imidazole, for molecular biology, ≥99.5% (GC), Lipoprotein Refolding Buffer, Lithium acetate dihydrate, ≥99.0% (NT), Lithium citrate tribasic tetrahydrate, ≥99.5% (NT), MES hydrate, ≥99.5% (T), MES monohydrate, for luminescence, ≥99.5% (T), MES solution, for molecular biology, 0.5 M in $H_2O$, MOPS, ≥99.5% (T), MOPS, for luminescence, ≥99.5% (T), MOPS, for molecular biology, ≥99.5% (T), Magnesium acetate solution, for molecular biology, ~1 M in $H_2O$, Magnesium acetate tetrahydrate, ≥99.0% (KT), Magnesium citrate tribasic nonahydrate, ≥98.0% (calc. based on dry substance, KT), Magnesium formate solution, 0.5 M in $H_2O$, Magnesium phosphate dibasic trihydrate, ≥98.0% (KT), Neutralization solution for the in-situ hybridization for in-situ hybridization, for molecular biology, Oxalic acid dihydrate, ≥99.5% (RT), PIPES, ≥99.5% (T), PIPES, for molecular biology, ≥99.5% (T), Phosphate buffered saline, solution (autoclaved), Phosphate buffered saline, washing buffer for peroxidase conjugates in Western Blotting, 10× concentrate, piperazine, anhydrous, ≥99.0% (T), Potassium D-tartrate monobasic, ≥99.0% (T), Potassium acetate solution, for molecular biology, Potassium acetate solution, for molecular biology, 5 M in H$_2$O, Potassium acetate solution, for molecular biology, ~1 M in H$_2$O, Potassium acetate, ≥99.0% (NT), Potassium acetate, for luminescence, ≥99.0% (NT), Potassium acetate, for molecular biology, ≥99.0% (NT), Potassium bicarbonate, ≥99.5% (T), Potassium carbonate, anhydrous, ≥99.0% (T), Potassium chloride, ≥99.5% (AT), Potassium citrate monobasic, ≥99.0% (dried material, NT), Potassium citrate tribasic solution, 1 M in H$_2$O, Potassium formate solution, 14 M in H$_2$O, Potassium formate, ≥99.5% (NT), Potassium oxalate monohydrate, ≥99.0% (RT), Potassium phosphate dibasic, anhydrous, ≥99.0% (T), Potassium phosphate dibasic, for luminescence, anhydrous, ≥99.0% (T), Potassium phosphate dibasic, for molecular biology, anhydrous, ≥99.0% (T), Potassium phosphate monobasic, anhydrous, ≥99.5% (T), Potassium phosphate monobasic, for molecular biology, anhydrous, ≥99.5% (T), Potassium phosphate tribasic monohydrate, ≥95% (T), Potassium phthalate monobasic, ≥99.5% (T), Potassium sodium tartrate solution, 1.5 M in H$_2$O, Potassium sodium tartrate tetrahydrate, ≥99.5% (NT), Potassium tetraborate tetrahydrate, ≥99.0% (T), Potassium tetraoxalate dihydrate, ≥99.5% (RT), Propionic acid solution, 1.0 M in H$_2$O, STE buffer solution, for molecular biology, pH 7.8, STET buffer solution, for molecular biology, pH 8.0, Sodium 5,5-diethylbarbiturate, ≥99.5% (NT), Sodium acetate solution, for molecular biology, ~3 M in H$_2$O, Sodium acetate trihydrate, ≥99.5% (NT), Sodium acetate, anhydrous, ≥99.0% (NT), Sodium acetate, for luminescence, anhydrous, ≥99.0% (NT), Sodium acetate, for molecular biology, anhydrous, ≥99.0% (NT), Sodium bicarbonate, ≥99.5% (T), Sodium bitartrate monohydrate, ≥99.0% (T), Sodium carbonate decahydrate, ≥99.5% (T), Sodium carbonate, anhydrous, ≥99.5% (calc. on dry substance, T), Sodium citrate monobasic, anhydrous, ≥99.5% (T), Sodium citrate tribasic dihydrate, ≥99.0% (NT), Sodium citrate tribasic dihydrate, for luminescence, ≥99.0% (NT), Sodium citrate tribasic dihydrate, for molecular biology, ≥99.5% (NT), Sodium formate solution, 8 M in H$_2$O, Sodium oxalate, ≥99.5% (RT), Sodium phosphate dibasic dihydrate, ≥99.0% (T), Sodium phosphate dibasic dihydrate, for luminescence, ≥99.0% (T), Sodium phosphate dibasic dihydrate, for molecular biology, ≥99.0% (T), Sodium phosphate dibasic dodecahydrate, ≥99.0% (T), Sodium phosphate dibasic solution, 0.5 M in H$_2$O, Sodium phosphate dibasic, anhydrous, ≥99.5% (T), Sodium phosphate dibasic, for molecular biology, ≥99.5% (T), Sodium phosphate monobasic dihydrate, ≥99.0% (T), Sodium phosphate monobasic dihydrate, for molecular biology, ≥99.0% (T), Sodium phosphate monobasic monohydrate, for molecular biology, ≥99.5% (T), Sodium phosphate monobasic solution, 5 M in H$_2$O, Sodium pyrophosphate dibasic, ≥99.0% (T), Sodium pyrophosphate tetrabasic decahydrate, ≥99.5% (T), Sodium tartrate dibasic dihydrate, ≥99.0% (NT), Sodium tartrate dibasic solution, 1.5 M in H$_2$O (colorless solution at 20° C.), Sodium tetraborate decahydrate, ≥99.5% (T), TAPS, ≥99.5% (T), TES, ≥99.5% (calc. based on dry substance, T), TM buffer solution, for molecular biology, pH 7.4, TNT buffer solution, for molecular biology, pH 8.0, TRIS Glycine buffer solution, 10× concentrate, TRIS acetate—EDTA buffer solution, for molecular biology, TRIS buffered saline, 10× concentrate, TRIS glycine SDS buffer solution, for electrophoresis, 10× concentrate, TRIS phosphate-EDTA buffer solution, for molecular biology, concentrate, 10× concentrate, Tricine, ≥99.5% (NT), Triethanolamine, ≥99.5% (GC), Triethylamine, ≥99.5% (GC), Triethylammonium acetate buffer, volatile buffer, ~1.0 M in H$_2$O, Triethylammonium phosphate solution, volatile buffer, ~1.0 M in H$_2$O, Trimethylammonium acetate solution, volatile buffer, ~1.0 M in H$_2$O, Trimethylammonium phosphate solution, volatile buffer, ~1 M in H$_2$O, Tris-EDTA buffer solution, for molecular biology, concentrate, 100× concentrate, Tris-EDTA buffer solution, for molecular biology, pH 7.4, Tris-EDTA buffer solution, for molecular biology, pH 8.0, Trizma® acetate, ≥99.0% (NT), Trizma® base, ≥99.8% (T), Trizma® base, ≥99.8% (T), Trizma® base, for luminescence, ≥99.8% (T), Trizma® base, for molecular biology, ≥99.8% (T), Trizma® carbonate, ≥98.5% (T), Trizma® hydrochloride buffer solution, for molecular biology, pH 7.2, Trizma® hydrochloride buffer solution, for molecular biology, pH 7.4, Trizma® hydrochloride buffer solution, for molecular biology, pH 7.6, Trizma® hydrochloride buffer solution, for molecular biology, pH 8.0, Trizma® hydrochloride, ≥99.0% (AT), Trizma® hydrochloride, for luminescence, ≥99.0% (AT), Trizma® hydrochloride, for molecular biology, ≥99.0% (AT), and Trizma® maleate, ≥99.5% (NT).

The nanoemulsion can comprise one or more emulsifying agents to aid in the formation of emulsions. Emulsifying agents include compounds that aggregate at the oil/water interface to form a kind of continuous membrane that prevents direct contact between two adjacent droplets. Certain embodiments of the present invention feature nanoemulsions that may readily be diluted with water to a desired concentration without impairing their antiviral properties.

6. Active Agents Incorporated into a Nanoemulsion of the Invention

In a further embodiment of the invention, a nanoemulsion comprises an additional active agent, such as an antibiotic or a palliative agent (such as for cancer treatment). Addition of another agent may enhance the therapeutic effectiveness of the nanoemulsion. Any) agent suitable for treating cancer can be incorporated into the topical nanoemulsions of the invention.

Examples of antibiotic agents include, but are not limited to, aminoglycosides, Ansamycins, Carbacephems, Carbapenems, Cephalosporins, Glycopeptides, Macrolides, Monobactams, Penicillins, Polypeptides, Polymyxin, Quinolones, Sulfonamides, Tetracyclines, and others (e.g., Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in US), Thiamphenicol, Tinidazole, Dapsone, and lofazimine).

Examples of these classes of antibiotics include, but are not limited to, Amikacin, Gentamicin, Kanamycin, Neomycin, Netilmicin, Streptomycin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Azithromycin, Clarithromycin, Dirithromycin, Erythromycin, Roxithromycin, Troleandomycin, Telithromycin, Spectinomycin, Aztreonam, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Bacitracin, Colistin, Polymyxin B, Ciprofloxacin, Enoxacin, Gatifloxacin, Levofloxacin, Lomefloxacin, Moxifloxacin, Norfloxacin, Ofloxacin, Trovafloxacin, Grepafloxacin, Sparfloxacin, Temafloxacin, Mafenide, Sulfonamidochrysoidine (archaic), Sulfacetamide, Sulfadiazine, Sulfamethizole, Sulfanilimide (archaic), Sulfasalazine, Sulfisoxazole, Trimethoprim, rimethoprim-Sulfamethoxazole (Co-trimoxazole) (TMP-SMX), Demeclocycline, Doxycycline, Minocycline, Oxytetracycline, and Tetracycline.

Examples of palliative agents which may be incorporated into the nanoemulsions of the invention include, but are not limited to, menthol, camphor, phenol, allantoin, benzocaine, corticosteroids, phenol, zinc oxide, camphor, pramoxine, dimethicone, meradimate, octinoxate, octisalate, oxybenzone, dyclonine, alcohols (e.g., benzyl alcohol), mineral oil, propylene glycol, titanium dioxide, silver nitrate ($AgNO_3$), silver sulfadiazine, mafenide acetate, nanocrystalline impregnated silver dressings, a p38 MAPK inhibitor, and magnesium stearate.

Exemplary Nanoemulsions

Several exemplary nanoemulsions are described below, although the methods of the invention are not limited to the use of such nanoemulsions. The components and quantity of each can be varied as described herein in the preparation of other nanoemulsions. ("CPC" refers to cetylpyridinium chloride, which is a cationic surfactant present in the nanoemulsions). Compositions are yaw % unless otherwise noted.

TABLE 1

Exemplary Nanoemulsions

| Nanoemulsion | Component | Weight Percent |
|---|---|---|
| $W_{20}5EC$ ED | Distilled Water | 23.418% |
| | EDTA | 0.0745% |
| | Cetylpyridinium Chloride | 1.068% |
| | Tween 20 | 5.92% |
| | Ethanol | 6.73% |
| | Soybean Oil | 62.79% |
| $P_{407}5EC$ | Distilled Water | 23.49% |
| | CPC | 1.068% |
| | Poloxamer 407 | 5.92% |
| | Ethanol | 6.73% |
| | Soybean Oil, NP | 62.79% |
| $W_{20}5GBA_2$ (v/v %) | Distilled Water | 20.93% |
| | BTC 824 | 2% |
| | Tween 20 | 5% |
| | Glycerine | 8% |
| | Soybean Oil | 64% |
| $W_{80}5EC$ | Water | 23.490% |
| | Ethanol | 6.730% |
| | Cetylpyridinium Chloride | 1.068% |
| | Polysorbate 80 | 5.920% |
| | Refined Soybean Oil | 62.790% |

The following nanoemulsions have an average particle (droplet) size of about 300 nm to about 600 nm: $W_{20}5EC$ ED, $P_{407}5EC$, $W_{20}5$ $GBA_2$, $W_{80}5EC$, and $W_{20}5$ $GBA_2ED$. The formulations listed in the table above are "neat" or "concentrated" formulations, meaning that the formulation intended for therapeutic use can be diluted as desired.

Methods of Manufacture

The nanoemulsions of the invention can be formed using classic emulsion forming techniques. See e.g., U.S. 2004/0043041. See also U.S. Pat. Nos. 6,015,832, 6,506,803, 6,559,189, 6,635,676, and US Patent Publication No. 20040043041, all of which are incorporated herein by reference. In addition, methods of making emulsions are described in U.S. Pat. Nos. 5,103,497 and 4,895,452 (herein incorporated by reference). In an exemplary method, the oil is mixed with the aqueous phase under relatively high shear forces (e.g., using high hydraulic and mechanical forces) to obtain a nanoemulsion comprising oil droplets having an average diameter of less than about 1000 nm. Some embodiments of the invention employ a nanoemulsion having an oil phase comprising an alcohol such as ethanol. The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In an exemplary embodiment, the nanoemulsions used in the methods of the invention comprise droplets of an oily discontinuous phase dispersed in an aqueous continuous phase, such as water. The nanoemulsions of the invention are stable, and do not decompose even after long storage periods. Certain nanoemulsions of the invention are non-toxic and safe when swallowed, inhaled, or contacted to the skin of a subject.

The compositions of the invention can be produced in large quantities and are stable for many months at a broad range of temperatures. The nanoemulsion can have textures ranging from that of a semi-solid cream to that of a thin lotion, and can be applied topically by hand, and can be sprayed onto a surface or nebulized.

As stated above, at least a portion of the emulsion may be in the form of lipid structures including, but not limited to, unilamellar, multilamellar, and paucliamellar lipid vesicles, micelles, and lamellar phases.

The present invention contemplates that many variations of the described nanoemulsions will be useful in the methods of the present invention. To determine if a candidate nanoemulsion is suitable for use with the present invention, three criteria are analyzed. Using the methods and standards described herein, candidate emulsions can be easily tested to determine if they are suitable. First, the desired ingredients are prepared using the methods described herein, to determine if a nanoemulsion can be formed. If a nanoemulsion cannot be formed, the candidate is rejected. Second, the candidate nanoemulsion should form a stable emulsion. A nanoemulsion is stable if it remains in emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate nanoemulsion should have efficacy for its intended use. For example, the emulsions of the invention should kill or disable microorganisms in vitro. To determine the suitability of a particular candidate nanoemulsion against a desired microorganism, the nanoemulsion is exposed to the microorganism for one or more time periods in a side-by-side experiment with an appropriate control sample (e.g., a negative control such as water) and determining if, and to what degree, the nanoemulsion kills or disables the microorganism.

The nanoemulsion of the invention can be provided in many different types of containers and delivery systems. For example, in some embodiments of the invention, the nanoemulsions are provided as a liquid, lotion, cream or other solid or semi-solid form. The nanoemulsions of the invention may be incorporated into hydrogel formulations.

The nanoemulsions can be delivered (e.g., to a subject or customers) in any suitable container. Suitable containers can be used that provide one or more single use or multi-use dosages of the nanoemulsion for the desired application. In some embodiments of the invention, the nanoemulsions are provided in a suspension or liquid form. Such nanoemulsions can be delivered in any suitable container including spray bottles (e.g., pressurized spray bottles, nebulizers).

In some embodiments, a nanoemulsion comprises from about 5 vol. % of TWEEN 80, from about 8 vol. % of ethanol, from about 1 vol. % of CPC, about 64 vol. % of oil (e.g., soybean oil), and about 22 vol. % of DiH$_2$O (designated herein as W$_{80}$5EC). In yet another alternative embodiment, a nanoemulsion comprises from about 5 vol. % of TWEEN 80, from about 8 vol. % of ethanol, about 64 vol. % of oil (e.g., soybean oil), and about 23 vol. % of DiH$_2$O (designated herein as W$_{80}$5E).

In some embodiments, the present invention provides a nanoemulsion comprising from about 5 vol. % of Poloxamer-407, from about 8 vol. % of ethanol, from about 1 vol. % of CPC, about 64 vol. % of oil (e.g., soybean oil), and about 22 vol. % of DiH$_2$O (designated herein as P$_{407}$5EC). Although an understanding of the mechanism is not necessary to practice the present invention, and the present invention is not limited to any particular mechanism, in some embodiments, a nanoemulsion comprising Poloxamer-407 does not elicit and/or augment immune responses (e.g., in the lung) in a subject. In some embodiments, various dilutions of a nanoemulsion provided herein (e.g., P$_{407}$5EC) can be utilized to treat (e.g., kill and/or inhibit growth of) bacteria. In some embodiments, undiluted nanoemulsion is utilized. In some embodiments, P$_{407}$5EC is diluted (e.g., in serial, two fold dilutions) to obtain a desired concentration of one of the constituents of the nanoemulsion (e.g., CPC).

In still other embodiments of the present invention, a nanoemulsion comprises from about 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC).

In some embodiments of the present invention, a nanoemulsion comprises from about 4 to 8 vol. % of TRITON X-100, from about 5 to 8 vol. % of TBP, about 30 to 70 vol. % of oil (e.g., soybean or olive oil), and about 0 to 30 vol. % of aqueous phase (e.g., DiH$_2$O or PBS). Additionally, certain of these embodiments further comprise about 1 vol. % of CPC, about 1 vol. % of benzalkonium chloride, about 1 vol. % cetylyridinium bromide, about 1 vol. % cetyldimethyletylammonium bromide, 500 µM EDTA, about 10 mM ammonium chloride, about 5 mM Inosine, and about 5 mM L-alanine. For example, in a certain preferred embodiment, a nanoemulsion comprises about 8 vol. % of TRITON X-100, about 8 vol. % of TBP, about 64 vol. % of soybean oil, and about 20 vol. % of DiH$_2$O (designated herein as X8P). In another embodiment of the present invention, a nanoemulsion comprises about 8 vol. % of TRITON X-100, about 8 vol. % of TBP, about 1% of CPC, about 64 vol. % of soybean oil, and about 19 vol. % of DiH$_2$O (designated herein as X8PC).

The candidate emulsion should form a stable emulsion. An emulsion is stable if it remains in emulsion form for a sufficient period to allow its intended use (e.g., to generate an immune response in a subject). For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% TWEEN 10, 1% CPC, 64% soybean oil, and 22% DiH$_2$O does not form a stable emulsion. In some embodiments, nanoemulsions of the present invention are stable for over a week, over a month, or over a year.

The present invention is not limited by the type of subject administered a composition of the present invention. The present invention is not limited by the particular formulation of a composition comprising a nanoemulsion adjuvant of the present invention. Indeed, a composition comprising a nanoemulsion of the present invention may comprise one or more different agents in addition to the nanoemulsion. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a nanoemulsion of the present invention comprises an agent and/or co-factor that enhance the ability of the nanoemulsion to induce an immune response. In some preferred embodiments, the presence of one or more co-factors or agents reduces the amount of nanoemulsion required for inducing an immune response. The present invention is not limited by the type of co-factor or agent used in a therapeutic agent of the present invention.

In some embodiments, a co-factor or agent used in a nanoemulsion composition is a bioactive agent. For example, in some embodiments, the bioactive agent may be a bioactive agent useful in a cell (e.g., a cell expressing a cancer antigen). Bioactive agents, as used herein, include diagnostic agents such as radioactive labels and fluorescent labels. Bioactive agents also include molecules affecting the metabolism of a cell (e.g., a cell expressing a cancer antigen), including peptides, nucleic acids, and other natural and synthetic drug molecules. Bioactive agents include, but are not limited to, adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; anti-peristaltic, antipneumocystic; antiproliferative; antiprostatic hypertrophy; antiprotozoal; antipruritic; antipsychotic; anti-rheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratolytic; LHRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine A1 antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; amyotrophic lateral sclerosis agent; cerebral ischemia agent; Paget's disease agent; unstable angina agent; uricosuric; vasoconstrictor; vasodilator; vulnerary; wound healing agent; xanthine oxidase inhibitor.

Molecules useful as antimicrobials can be delivered by the methods and compositions of the invention. Antibiotics that may find use in co-administration with a composition comprising a nanoemulsion of the present invention include, but are not limited to, agents or drugs that are bactericidal and/or bacteriostatic (e.g., inhibiting replication of bacteria or inhibiting synthesis of bacterial components required for survival of the infecting organism), including, but not limited to, almecillin, amdinocillin, amikacin, amoxicillin, amphomycin, amphotericin B, ampicillin, azacitidine, azaserine, azithromycin, azlocillin, aztreonam, bacampicillin, bacitracin, benzyl penicilloyl-polylysine, bleomycin, candicidin, capreomycin, carbenicillin, cefaclor, cefadroxil, cefamandole, cefazoline, cefdinir, cefepime, cefixime, cefinenoxime, cefinetazole, cefodizime, cefonicid, cefoperazone, cefzinir, cefotaxime, cefotetan, cefotiam, cefoxitin, cefpiramide, cefpodoxime, cefprozil, cefsulodin, ceftazidime, ceftibuten, ceftizoxime, ceftriaxone, cefuroxime, cephacetrile, cephalexin, cephaloglycin, cephaloridine, cephalothin, cephapirin, cephradine, chloramphenicol, chlortetracycline, cilastatin, cinnamycin, ciprofloxacin, clarithromycin, clavulanic acid, clindamycin, clioquinol, cloxacillin, colistimethate, colistin, cyclacillin, cycloserine, cyclosporine, cyclo-(Leu-Pro), dactinomycin, dalbavancin, dalfopristin, daptomycin, daunorubicin, demeclocycline, detorubicin, dicloxacillin, dihydrostreptomycin, dirithromycin, doxorubicin, doxycycline, epirubicin, erythromycin, eveminomycin, floxacillin, fosfomycin, fusidic acid, gemifloxacin, gentamycin, gramicidin, griseofulvin, hetacillin, idarubicin, imipenem, iseganan, ivermectin, kanamycin, laspartomycin, linezolid, linocomycin, loracarbef, magainin, meclocycline, meropenem, methacycline, methicillin, mezlocillin, minocycline, mitomycin, moenomycin, moxalactam, moxifloxacin, mycophenolic acid, nafcillin, natamycin, neomycin, netilmicin, niphimycin, nitrofurantoin, novobiocin, oleandomycin, oritavancin, oxacillin, oxytetracycline, paromomycin, penicillamine, penicillin G, penicillin V, phenethicillin, piperacillin, plicamycin, polymyxin B, pristinamycin, quinupristin, rifabutin, rifampin, rifamycin, rolitetracycline, sisomicin, spectrinomycin, streptomycin, streptozocin, sulbactam, sultamicillin, tacrolimus, tazobactam, teicoplanin, telithromycin, tetracycline, ticarcillin, tigecycline, tobramycin, troleandomycin, tunicamycin, tyrthricin, vancomycin, vidarabine, viomycin, virginiamycin, BMS-284,756, L-749,345, ER-35,786, S-4661, L-786,392, MC-02479, Pep5, RP 59500, and TD-6424.

In some embodiments, a composition comprising a nanoemulsion of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a nanoemulsion) enhances an immune response in a host subject due to an increase in duration and/or amount of exposure to the nanoemulsion that a subject experiences when a mucoadhesive is used compared to the duration and/or amount of exposure to the nanoemulsion in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, pulmonary, subcutaneous, intramuscular, intraperitoneal, intravenous, or administration via other routes may be found in Remington's Pharmaceutical Sciences, Mack Publishing Company, Easton, Pa.

A composition comprising a nanoemulsion of the present invention can be used therapeutically or as a prophylactic. A composition comprising a nanoemulsion of the present invention can be administered to a subject via a number of different delivery routes and methods.

For example, the compositions of the present invention can be administered to a subject (e.g., mucosally or by pulmonary route) by multiple methods, including, but not limited to: being applied to a surface; being sprayed onto a surface using a spray applicator; being mixed with a mucoadhesive and applied (e.g., sprayed or wiped) onto a surface (e.g., mucosal or pulmonary surface); being placed on or impregnated onto a nasal and/or pulmonary applicator and applied; being applied by a controlled-release mechanism; applied using a nebulizer, aerosolized, being applied as a liposome; or being applied on a polymer.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal and pulmonary techniques), as well as European Publication No. 517,565 and Ilium et al., J. Controlled Rel., 1994, 29:133-141 (e.g., for techniques of intranasal administration), each of which is hereby incorporated by reference in its entirety). The present invention is not limited by the route of administration.

Methods of intranasal and pulmonary administration are well known in the art, including the administration of a droplet or spray form of the nanoemulsion into the nasopharynx of a subject to be treated. In some embodiments, a nebulized or aerosolized composition comprising a nanoemulsion is provided. Enteric formulations such as gastro resistant capsules for oral administration, suppositories for rectal or vaginal administration may also form part of this invention. Compositions of the present invention may also be administered via the oral route. Under these circumstances, a composition comprising a nanoemulsion may comprise a pharmaceutically acceptable excipient and/or include alkaline buffers, or enteric capsules. Formulations for nasal delivery may include those with dextran or cyclodextran and saponin as an adjuvant.

In some embodiments, a nanoemulsion vaccine of the present invention is administered via a pulmonary delivery route and/or means. For example, in some embodiments, an aqueous solution containing the nanoemulsion is gently and thoroughly mixed to form a solution. The solution is sterile filtered (e.g., through a 0.2 micron filter) into a sterile, enclosed vessel. Under sterile conditions, the solution is passed through an appropriately small orifice to make droplets (e.g., between 0.1 and 10 microns).

The particles may be administered using any of a number of different applicators. Suitable methods for manufacture and administration are described in the following U.S. Pat. Nos. 6,592,904; 6,518,239; 6,423,344; 6,294,204; 6,051,256 and 5,997,848 to INHALE (now NEKTAR); and U.S. Pat. No. 5,985,309; RE37,053; U.S. Pat. Nos. 6,436,443; 6,447,753; 6,503,480; and 6,635,283, to Edwards, et al. (MIT, AIR), each of which is hereby incorporated by reference in its entirety.

Thus, in some embodiments, compositions of the present invention are administered by pulmonary delivery. For example, a composition of the present invention can be delivered to the lungs of a subject (e.g., a human) via inhalation (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colo.; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)). In some embodiments, a composition comprising a nanoemulsion is administered to a subject by more than one route or means (e.g., administered via pulmonary route as well as a mucosal route).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the ULTRAVENT nebulizer (Mallinckrodt Inc., St. Louis, Mo.); the ACORN II nebulizer (Marquest Medical Products, Englewood, Colo.); the VENTOLIN metered dose inhaler (Glaxo Inc., Research Triangle Park, N.C.); and the SPINHALER powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising a nanoemulsion of the present invention may be used to protect and/or treat a subject susceptible to, or suffering from, a disease (e.g., cancer) by means of administering compositions comprising a nanoemulsion by mucosal, intramuscular, intraperitoneal, intradermal, transdermal, pulmonary, intravenous, subcutaneous or other route of administration described herein. Methods of systemic administration of the nanoemulsion and/or agent co-administered with the nanoemulsion may include conventional syringes and needles, or devices designed for ballistic delivery (See, e.g., WO 99/27961, hereby incorporated by reference), or needleless pressure liquid jet device (See, e.g., U.S. Pat. No. 4,596,556; U.S. Pat. No. 5,993,412, each of which are hereby incorporated by reference), or transdermal patches (See, e.g., WO 97/48440; WO 98/28037, each of which are hereby incorporated by reference). In some embodiments, the present invention provides a delivery device for systemic administration, pre-filled with the nanoemulsion vaccine composition of the present invention.

In some embodiments, a nanoemulsion cancer vaccine of the invention is administered to a subject with cancer. A subject may be one who has (e.g., that is clinically diagnosed (e.g., via biopsy, x-ray, blood test, etc.) as having) or that suspected of having cancer (e.g., of any stage or progression state (e.g., metastatic cancer)). In some embodiments, a subject administered a vaccine of the invention is a subject that has undergone surgery to remove cancer. In some embodiments, a subject administered a vaccine of the invention is a subject that is in remission. In some embodiments, a subject administered a vaccine of the invention is a subject that has one or more lymph nodes that test positive for cancer.

As described above, the present invention is not limited by the type of subject administered a composition of the present invention. Indeed, a wide variety of subjects are contemplated to be benefited from administration of a composition of the present invention. In some embodiments, the subject is a human. In some embodiments, human subjects are of any age (e.g., adults, children, infants, etc.) that have, have had, or that are likely to have recurrence of (e.g., that are in remission) cancer.

In some embodiments a composition comprising a nanoemulsion of the present invention is administered (e.g., to a subject (e.g., via pulmonary and/or mucosal route)) as a therapeutic or as a prophylactic to prevent cancer, cancer growth and/or cancer metastasis (e.g., tumor metastasis).

In some embodiments, vaccine compositions of the invention comprise adjunct components conventionally found in pharmaceutical compositions. For example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the nanoemulsion. In some embodiments, nanoemulsion vaccine compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, an immunogenic vaccine composition of the invention is mixed with a pharmaceutically acceptable excipient, more preferably with an adjuvant to form a vaccine.

In some embodiments, a cancer vaccine of the invention comprises one or more adjuvants (e.g., a non-specific stimulator of an immune response). In some embodiments, the adjuvant is any immunostimulatory compound including, but not limited to, cytokines, chemokines, cofactors, toxins, plasmodia, and/or synthetic compositions. Exemplary adjuvants include, but are not limited to, IL-1, IL-2, IL-4, IL-7, IL-12, interferon-γ, GMCSP, BCG, aluminum hydroxide, MDP compounds, such as thur-MDP and nor-MDP, CGP (MTP-PE), lipid A, and monophosphoryl lipid A (MPL), RIBI, which contains three components extracted from bacteria, MPL, trehalose dimycolate (TDM) and cell wall skeleton (CWS) in a 2% squalene/Tween 80 emulsion is also contemplated. MHC antigens may be used. Other adjuvants include complete Freund's adjuvant (a non-specific stimulator of the immune response containing killed *Mycobacterium tuberculosis*), incomplete Freund's adjuvants and aluminum hydroxide adjuvant.

In some embodiments, a cancer vaccine of the invention is coadministered with a biologic response modifiers (BRM) (e.g., that has been shown to upregulate T cell immunity or downregulate suppressor cell activity). Exemplary BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as interferon-γ, IL-2, or IL-12 or genes encoding proteins involved in immune helper functions, such as B-7. A subject can be administered a vaccine generally as described herein. The vaccine may be mixed with an adjuvant. Booster administrations with the same or different vaccine may occur (e.g., at approximately two, three, four, five, six, seven, eight, nine, ten-week or more (e.g., 3, 4, 5, 6, 7, 8, 9, 10, 11 month or more (e.g., 1, 2, 3, 4, 5, 6, 7, 8, 9 year or more)) intervals.

Thus, in some embodiments, vaccines of the present invention are preferably adjuvanted. As described herein, suitable adjuvants include an aluminum salt such as aluminum hydroxide gel (alum) or aluminium phosphate, but may also be a salt of calcium, magnesium, iron or zinc, or may be an insoluble suspension of acylated tyrosine, or acylated sugars, cationically or anionically derivatized polysaccharides, or polyphosphazenes.

In some embodiments, the adjuvant is selected to be a preferential inducer of either a TH1 or a TH2 type of response. High levels of Th1 type cytokines tend to favor the induction of cell mediated immune responses to a given antigen, while high levels of Th2 type cytokines tend to favor the induction of humoral immune responses to the antigen.

Distinctions between Th1 and Th2 type immune response are not absolute. In reality a subject will support an immune response which is described as being predominantly Th1 or predominantly Th2. However, it is often convenient to consider the families of cytokines in terms of that described in murine CD4 +ve T cell clones (See, e.g., Mosmann, and Coffman, (1989) Annual Review of Immunology, 7, p145173). Traditionally, Th1 type responses are associated with the production of INF-γ and IL2 cytokines by Tlymphocytes. Other cytokines often directly associated with the induction of Th1 type immune responses are not produced by Tcells, such as IL12. In contrast, Th2 type responses are associated with the secretion of 114, IL5, IL6, IL10. Suitable adjuvant systems that promote a predominantly Th1 response include: Monophosphoryl lipid A or a derivative thereof, particularly 3deOacylated monophosphoryl lipid A (3DMPL) (for its preparation see, e.g., GB 2220211 A); and a combination of monophosphoryl lipid A, preferably 3deOacylated monophosphoryl lipid A, together with an aluminium salt (for example aluminium phosphate or aluminium hydroxide). In such combinations, antigen and 3DMPL are contained in the same particulate structures, allowing for more efficient delivery of antigenic and immunostimulatory signals. Studies have shown that 3DMPL is able to further enhance the immunogenicity of an alumadsorbed antigen (See, e.g., Thoelen et al. Vaccine (1998) 16:70814; EP 689454B1].

In some embodiments, a vaccine comprises the combination of a monophosphoryl lipid A and a saponin derivative, particularly the combination of QS21 and 3DMPL as disclosed in WO 94/00153, or a less reactogenic composition where the QS21 is quenched with cholesterol as disclosed in WO 96/33739. For example, the adjuvant formulation comprises liposomes containing QS21 and 3DMPL which is either within the vesicle membrane or added following the formulation of the liposomes so that it is associated with the vesicle membrane but not within the vesicle membrane. A particularly potent adjuvant formulation involving QS21, 3DMPL and tocopherol in an oil in water emulsion is described in WO 95/17210, and is a preferred formulation. Preferably the vaccine additionally comprises a saponin, more preferably QS21. The vaccine compositions may also comprise a nanoemulsion and tocopherol (WO 95/17210). The present invention also provides a method for producing a vaccine formulation comprising mixing a protein of the present invention together with a pharmaceutically acceptable excipient, such as 3DMPL. Unmethylated CpG containing oligonucleotides (WO 96/02555) are also preferential inducers of a TH1 response and are suitable for use in the present invention.

In some embodiments, a vaccine composition of the invention is utilized with compositions forming a liposome structure. Liposomes preferably contain a neutral lipid, for example phosphatidylcholine, which is preferably noncrystalline at room temperature, for example eggyolk phosphatidylcholine, dioleoyl phosphatidylcholine or dilauryl phosphatidylcholine. The liposomes may also contain a charged lipid which increases the stability of the vaccine comprising lipids. In these cases the amount of charged lipid is preferably 1-20% w/w, most preferably 5-10%.

In some embodiments, compositions of the invention contain MPL (3deacylated monophosphoryl lipid A, also known as 3DMPL). 3DMPL is a mixture of 3 types of De-O-acylated monophosphoryl lipid A with 4, 5 or 6 acylated chains and is manufactured by Ribi Immunochem, Montana.

Suitable compositions of the invention are those wherein liposomes are initially prepared without MPL, and MPL is then added, preferably as 100 nm particles. The MPL is therefore not contained within the vesicle membrane (known as MPL out). Compositions where the MPL is contained within the vesicle membrane (known as MPL in) also form an aspect of the invention. The antigen can be contained within the vesicle membrane or contained outside the vesicle membrane. Preferably soluble antigens are outside and hydrophobic or lipidated antigens are either contained inside or outside the membrane.

Vaccine preparations of the present invention may be administered (e.g., therapeutically and/or prophylactically) to protect or treat a subject by means of administering the vaccine via systemic or mucosal route. These administrations may include injection via the intramuscular, intraperitoneal, intradermal or subcutaneous routes; or via mucosal administration to the oral/alimentary, respiratory, genitourinary tracts. In some preferred embodiments, administration is intranasal. Although a vaccine of the invention may be administered as a single dose, components thereof may also be co-administered together at the same time or at different times (for example, whole cell vaccines may be administered separately, at the same time or 12 weeks after the administration of any protein component of the vaccine for optimal coordination of the immune responses with respect to each other). For co-administration, the optional adjuvant (e.g., Th1 and/or Th2 adjuvant) may be present in any or all of the different administrations. In addition to a single route of administration, two or more different routes of administration may be used. For example, whole cell lysate vaccines may be nasally administered and vaccines comprising a protein component may be administered via intra-dermally. In addition, the vaccines of the invention may be administered for priming doses and/or for booster doses.

The amount of cancer antigen in each vaccine dose is selected as an amount that induces an immunoprotective response without significant, adverse side effects in typical vaccines. Such amount will vary depending upon which specific cancer immunogen/antigen and/or plurality thereof are employed and how it is presented. In some embodiments, the amount of immunogen (e.g., cancer antigen) is an amount effective at inducing an immune response to the immunogen.

In some embodiments, vaccines comprising protein components (e.g., a protein subcomponent of a cancer cell (e.g., recombinant cancer cell protein) generally comprise from 0.0001-0.1 µg, 0.1-100 µg, 100-200 µg, 200-500 µg, 500-1000 µg, or more of antigen, preferably 0.1-50 µg, preferably 0.1-10 µg, more preferably 1-10 µg, of which 1 to 5 µg is a more preferable range.

In some embodiments, the content of protein antigens in the vaccine will typically be in the range 1-100 µg, preferably 5-50 µg, most typically in the range 5-25 µg. Following an initial vaccination, subjects may receive one or several booster immunizations adequately spaced.

Vaccines of the present invention may be stored in solution or lyophilized. Preferably the solution is lyophilized in the presence of a sugar such as sucrose, trehalose or lactose. In some embodiments, it is preferable that the vaccines are lyophilized and extemporaneously reconstituted prior to use.

Antibodies and Passive Immunization

Another aspect of the invention is a method of preparing an immune globulin for use in prevention or treatment of cancer comprising the steps of immunizing a subject with an immunogenic composition comprising a nanoemulsion and one or more cancer immunogens of the invention and isolating immune globulin from the recipient. An immune globulin prepared by this method is a further aspect of the invention. A pharmaceutical composition comprising the immune globulin of the invention and a pharmaceutically acceptable carrier is a further aspect of the invention (e.g., that are utilized in the manufacture of a medicament for the treatment or prevention of cancer). A method for treatment or prevention of cancer comprising a step of administering to a subject an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a subject and the inoculated subject is then maintained for a time sufficient for the antigenic composition to induce protective antibodies.

The antibodies can be isolated to the extent desired by well known techniques such as affinity chromatography (See, e.g., Harlow and Lane Antibodies; a laboratory manual 1988).

Antibodies include antiserum preparations from a variety of commonly used animals e.g. goats, primates, rabbits, donkeys, swine, horses, guinea pigs, rats or man. The animals are bled and serum recovered.

An immune globulin produced in accordance with the present invention can include whole antibodies, antibody fragments or subfragments. Antibodies can be whole immunoglobulins of any class e.g. IgG, IgM, IgA, IgD or IgE, chimeric antibodies or hybrid antibodies with dual specificity to two or more antigens of the invention. They may also be fragments e.g. F(ab')2, Fab', Fab, Fv and the like including hybrid fragments. An immune globulin also includes natural, synthetic or genetically engineered proteins that act like an antibody by binding to specific antigens to form a complex.

Monoclonal antibodies that specifically bind to cancer (e.g., a cancer antigen and/or immunogen) can be prepared using any technique which provides for the production of antibody molecules by continuous cell lines in culture. These techniques include, but are not limited to, the hybridoma technique, the human B cell hybridoma technique, and the EBV hybridoma technique (See, e.g., Kohler et al., Nature 256, 495 497, 1985; Kozbor et al., J. Immunol. Methods 81, 3142, 1985; Cote et al., Proc. Natl. Acad. Sci. 80, 2026 2030, 1983; Cole et al., Mol. Cell. Biol. 62, 109 120, 1984).

In addition, techniques developed for the production of "chimeric antibodies," the splicing of mouse antibody genes to human antibody genes to obtain a molecule with appropriate antigen specificity and biological activity, can be used (See, e.g., Morrison et al., Proc. Natl. Acad. Sci. 81, 68516855, 1984; Neuberger et al., Nature 312, 604 608, 1984; Takeda et al., Nature 314, 452 454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (See, e.g., Burton, Proc. Natl. Acad. Sci. 88, 11120 23, 1991).

Single-chain antibodies also can be constructed using a DNA amplification method, such as PCR, using hybridoma cDNA as a template (See, e.g., Thirion et al., 1996, Eur. J. Cancer Prev. 5, 507-11). Single-chain antibodies can be mono- or bispecific, and can be bivalent or tetravalent. Construction of tetravalent, bispecific single-chain antibodies is taught, for example, in Coloma & Morrison, 1997, Nat. Biotechnol. 15, 159-63. Construction of bivalent, bispecific single-chain antibodies is taught, for example, in Mallender & Voss, 1994, J. Biol. Chem. 269, 199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (See, e.g., Verhaar et al., 1995, Int. J. Cancer 61, 497-501; Nicholls et al., 1993, J. Immunol. Meth. 165, 81-91).

Antibodies which specifically bind to a particular antigen also can be produced by inducing in vivo production in the lymphocyte population or by screening immunoglobulin libraries or panels of highly specific binding reagents as disclosed in the literature (See, e.g., Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared. Antibodies can be purified by methods well known in the art. For example, antibodies can be affinity purified by passage over a column to which the relevant antigen is bound. The bound antibodies can then be eluted from the column using a buffer with a high salt concentration.

A vaccine of the present invention can be administered to a subject who then acts as a source of immune globulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat staphylococcal infection. Hyperimmune globulins of the invention are particularly useful for treatment or prevention of staphylococcal disease in infants, immune compromised individuals or where treatment is required and there is no time for the individual to produce antibodies in response to vaccination.

An additional aspect of the invention is a pharmaceutical composition comprising two of more monoclonal antibodies (or fragments thereof; preferably human or humanized) reactive against at least two constituents of the immunogenic composition of the invention, which could be used to treat or prevent cancer and/or cancer metastasis.

Such pharmaceutical compositions comprise monoclonal antibodies that can be whole immunoglobulins of any class e.g. IgG, IgM, IgA, IgD or IgE, chimeric antibodies or hybrid antibodies with specificity to two or more antigens of the invention. They may also be fragments e.g. F(ab')2, Fab', Fab, Fv and the like including hybrid fragments.

Methods of making monoclonal antibodies are well known in the art and can include the fusion of splenocytes with myeloma cells (See, e.g., Kohler and Milstein 1975 Nature 256; 495; Antibodies—a laboratory manual Harlow and Lane 1988). Alternatively, monoclonal Fv fragments can be obtained by screening a suitable phage display library (See, e.g., Vaughan T J et al 1998 Nature Biotechnology 16; 535). Monoclonal antibodies may be humanized or part humanized by known methods.

The invention also encompasses method of making the immunogenic compositions and vaccines of the invention.

A preferred process of the invention, is a method to make a vaccine comprising the steps of mixing one or more antigens and one or more nanoemulsions to make an immunogenic composition of the invention. Optionally, a pharmaceutically acceptable excipient and/or adjuvant is added.

Methods of Treatment

The invention also encompasses method of treatment and/or prevention of cancer and/or cancer metastasis. In some embodiments, a vaccine composition of the invention is utilized with other types of cancer treatment or therapy. For example, in some embodiments, a vaccine composition is utilized together with (e.g., before, during and/or after) surgery to remove cancer. Such patients will know the date of surgery in advance and could be inoculated in advance. As described herein, the amount of antigen/immunogen (e.g., whole cancer cells (e.g., that have undergone freeze-thaw lysis and/or other type of membrane disruption), homogenized cells (e.g., cancer cells (e.g., a cancer cell line or genetically modified cancer cells), cells (e.g., cancer cells (e.g., that have been exposed to UV radiation), one or a plurality of tumor associated antigens (e.g., recombinant and/or purified protein antigens), cells modified (e.g., genetically modified) to express (e.g., over-express) one or a plurality of tumor associated antigens, one or a plurality of protein components (e.g., isolated and/or purified and/or recombinant protein) from one or a plurality of cancer cells, and/or one or more adjuvants (e.g., a nanoemulsion adjuvant and/or non-nanoemulsion adjuvant) is selected as an amount which induces an immunoprotective and/or therapeutic response without significant, adverse side effects in typical vaccines.

Although the vaccines of the present invention may be administered by any route, administration of the described vaccines to intranasal mucosa forms a preferred embodiment of the invention. In some embodiments, a vaccine is injected into the skin, and in particular the dermis, to stimulate an immune response. In some embodiments, intradermal vaccination with the vaccines described herein forms a preferred embodiment of the invention.

Devices that are specifically designed to administer liquid agents into or across the skin have been described, for example the devices described in WO 99/34850 and EP 1092444, also the jet injection devices described for example in WO 01/13977; U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

In some embodiments, when the vaccines of the present invention are to be administered (e.g., via mucosal route, intradermally, etc.), the vaccine is in a low liquid volume, particularly a volume of between about 0.025 ml and 0.5 ml, or more preferably 0.05 ml and 0.2 ml, although lower and higher volume doses may be utilized. In some embodiments, the content of antigens in the intradermal and/or mucosal vaccines of the present invention may be similar to conventional doses as found in intramuscular vaccines.

In some embodiments, the present invention provides a use of the immunogenic composition of the invention in the manufacture of a vaccine for treatment or prevention of cancer.

The present invention also includes methods involving co-administration of a composition comprising a nanoemulsion vaccine with one or more additional active agents. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., anti-cancer agents (e.g., chemotherapeutic), a second type of nanoemulsion vaccine, etc.) can be any of the well-known agents in the art, including, but not limited to, those that are currently in clinical use.

In some embodiments, a composition comprising a nanoemulsion is administered to a subject via more than one route. For example, a subject may benefit from receiving mucosal administration (e.g., nasal administration or other mucosal routes described herein) and, additionally, receiving one or more other routes of administration (e.g., pulmonary administration (e.g., via a nebulizer, inhaler, or other methods described herein).

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

The present invention is not limited by the amount of nanoemulsion vaccine used. The amount will vary depending upon which specific nanoemulsion vaccine (s) is/are employed, and can vary from subject to subject, depending on a number of factors including, but not limited to, the species, age and general condition (e.g., health) of the subject, and the mode of administration. Procedures for determining the appropriate amount of nanoemulsion vaccine administered to a subject to induce an immune response in a subject can be readily determined using known means by one of ordinary skill in the art.

In some embodiments, it is expected that each dose (e.g., of a composition comprising a nanoemulsion vaccine comprises 1-40% nanoemulsion, in some embodiments, 20% nanoemulsion, in some embodiments less than 20% (e.g., 15%, 10%, 8%, 5% or less nanoemulsion), and in some embodiments greater than 20% nanoemulsion (e.g., 25%, 30%, 35%, 40% or more nanoemulsion). An optimal amount for a particular administration can be ascertained by one of skill in the art using standard studies involving observation of immune responses described herein.

In some embodiments, it is expected that each dose (e.g., of a composition comprising a nanoemulsion vaccine is from 0.001 to 40% or more (e.g., 0.001-10%, 0.5-5%, 1-3%, 2%, 6%, 10%, 15%, 20%, 30%, 40% or more) by weight nanoemulsion.

Similarly, the present invention is not limited by the duration of time a vaccine is administered to a subject (e.g., to induce immune priming and/or responses). In some embodiments, a vaccine is administered one or more times (e.g. twice, three times, four times or more) daily. In some embodiments, a composition comprising a vaccine is administered one or more times a day until a suitable level of immune response is generated and/or the immune response is sustained. In some embodiments, a composition comprising a vaccine of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the vaccine present in the concentrated composition. Concentrated compositions are contemplated to be useful in a setting in which large numbers of subjects may be administered a composition of the present invention.

In some embodiments, a composition comprising a nanoemulsion vaccine of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Dosage units may be proportionately increased or decreased based on several factors including, but not limited to, the weight, age, and health status of the subject. In addition, dosage units may be increased or decreased for subsequent administrations.

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The formulations can be tested in vivo in a number of animal models developed for the study of pulmonary, mucosal and other routes of delivery. As is readily apparent, the compositions of the present invention are useful for preventing and/or treating a wide variety of cancers and/or metastasis and/or other types of abnormal tissue or cellular growth. Not only can the compositions be used prophylactically or therapeutically, the compositions can also be used, as described above, in order to prepare antibodies (immune globulins), both polyclonal and monoclonal. In some embodiments, preparation of an immune globulin as described herein is utilized for the immunopurification of an antigen (e.g., a cancer antigen) of interest.

In one embodiment, the nanoemulsion vaccines of the present invention are useful for generating antigen-specific antibodies that are useful in the specific identification of that antigen (e.g., cancer antigen) in an immunoassay according to a diagnostic embodiment. Such immunoassays include enzyme-linked immunosorbent assays (ELISA), RIAs and other non-enzyme linked antibody binding assays or procedures known in the art. In ELISA assays, the antigen-specific antibodies are immobilized onto a selected surface; for example, the wells of a polystyrene microtiter plate. After washing to remove incompletely adsorbed antibodies, a nonspecific protein, such as a solution of bovine serum albumin (BSA) or casein, that is known to be antigenically neutral with regard to the test sample may be bound to the selected surface. This allows for blocking of nonspecific adsorption sites on the immobilizing surface and thus reduces the background caused by nonspecific bindings of antigens onto the surface. The immobilizing surface is then contacted with a sample, such as clinical or biological materials, to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for about 2 to 4 hours, at temperatures such as of the order of about 25-37° C. Following incubation, the sample-contacted surface is washed to remove non-immunocomplexed material. The washing procedure may include washing with a solution such as PBS/Tween, or a borate buffer.

Following formation of specific immunocomplexes between the antigen in the test sample and the bound antigen-specific antibodies, and subsequent washing, the occurrence, and even amount, of immunocomplex formation may be determined by subjecting the immunocomplex to a second antibody having specificity for the antigen. To provide detecting means, the second antibody may have an associated activity, such as an enzymatic activity, that will generate, for example, a color development upon incubating with an appropriate chromogenic substrate. Quantification may then be achieved by measuring the degree of color generation using, for example, a visible spectra spectrophotometer. In an additional embodiment, the present invention includes a diagnostic kit comprising antigen-specific antibodies generated by immunization of a host with immunogenic compositions produced according to the present invention.

In some embodiments, the present invention provides a kit comprising a composition comprising a nanoemulsion vaccine. In some embodiments, the kit further provides a device for administering the composition. The present invention is not limited by the type of device included in the kit. In some embodiments, the device is configured for nasal and/or pulmonary application of the composition of the present invention (e.g., a nasal inhaler or nasal mister). In some embodiments, a kit comprises a composition comprising a nanoemulsion vaccine in a concentrated form (e.g., that can be diluted prior to administration to a subject).

In some embodiments, all kit components are present within a single container (e.g., vial or tube). In some embodiments, each kit component is located in a single container (e.g., vial or tube (e.g., a nanoemulsion adjuvant is present in one container and an immunogen is present in a second, separate container)). In some embodiments, one or more kit components are located in a single container (e.g., vial or tube) with other components of the same kit being located in a separate container (e.g., vial or tube). In some embodiments, a kit comprises a buffer. In some embodiments, the kit further comprises instructions for use.

Animal Models

In some embodiments, nanoemulsion vaccine compositions (e.g., for generating an immune response) are tested in animal models of cancer, metastasis and/or other type of abnormal cellular growth. The use of well-developed animal models provides a method of measuring the effectiveness and safety of a vaccine before administration to human subjects.

Assays for Evaluation of Adjuvants and Vaccines

In some embodiments, nanoemulsion vaccines are evaluated using one of several suitable model systems. For example, cell-mediated immune responses can be evaluated in vitro. In addition, an animal model may be used to evaluate in vivo immune responses (e.g., toward irregular cell and/or tissue growth and/or metastasis in a subject).

In addition, the stability of emulsion-developed vaccines is evaluated, particularly over time and storage condition, to ensure that vaccines are effective long-term. The ability of other stabilizing materials (e.g., dendritic polymers) to enhance the stability and immunogenicity of vaccines is also evaluated.

Once a given nanoemulsion vaccine has been formulated, the ability of the vaccine to elicit an immune response (e.g., and provide prophylactic and/or therapeutic benefits) is optimized. For example, the timing and dosage of the vaccine can be varied and the most effective dosage and administration schedule determined. The level of immune response is quantified by measuring serum antibody levels. In addition, in vitro assays are used to monitor proliferation activity by measuring $H^3$-thymidine uptake. In addition to proliferation, Th1 and Th2 cytokine responses (e.g., including but not limited to, levels of include IL-2, TNF-α, IFN-γ, IL-4, IL-6, IL-11, IL-12, etc.) are measured to qualitatively evaluate the immune response.

Finally, animal models are utilized to evaluate the effect of a nanoemulsion mucosal vaccine. In some embodiments, the level of immune response is evaluated by challenging animals (e.g., with specific cancerous and/or metastatic cells and/or agents) and subsequently evaluating the level of disease (e.g., presence of cancer and/or metastasis (See, e.g., Example 8). The level of immunity is measured over time to determine the necessity and spacing of booster immunizations.

In some embodiments, a composition comprising a nanoemulsion adjuvant described herein (e.g., with or without an immunogen) comprises one or more additional adjuvants that induce and/or skew toward a Th1-type response. However, in other embodiments, it will be preferred that a composition comprising a nanoemulsion adjuvant described herein (e.g., with or without an immunogen) comprises one or more additional adjuvants that induce and/or skew toward a Th2-type response.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

In some embodiments, a composition comprising a vaccine of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. In some embodiments, one or more components of the vaccine function as a mucoadhesive (e.g., individually, or in combination with other components of the NE adjuvant). Although an understanding of the mechanism is not necessary to practice the present invention and the present invention is not limited to any particular mechanism of action, in some embodiments, use of a mucoadhesive (e.g., in a composition comprising a vaccine) enhances induction of an immune response (e.g., an innate and/or adaptive immune response) in a subject (e.g., a subject administered a composition of the present invention) due to an increase in duration and/or amount of exposure to an immunogen that a subject experiences when a mucoadhesive is used compared to the duration and/or amount of exposure to an immunogen in the absence of using the mucoadhesive).

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some preferred embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science and Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the preferred route of administration as it has been shown that mucosal administration of antigens has a greater efficacy of inducing protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). More advantageously, in further preferred embodiments, in addition to inducing mucosal immune responses, mucosal vaccination also induces systemic immunity. In some embodiments, non-parenteral administration (e.g., muscosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a nanoemulsion adjuvant and an immunogen of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition comprising a nanoemulsion adjuvant and immunogen is provided. Enteric formulations such as gastro resistant capsules for oral administration, suppositories for rectal or vaginal administration also form part of this invention. Compositions of the present invention may also be administered via the oral route. Under these circumstances, a composition comprising a nanoemulsion adjuvant and an immunogen may comprise a pharmaceutically acceptable excipient and/or include alkaline buffers, or enteric capsules. Formulations for nasal delivery may include those with dextran or cyclodextran and saponin as an adjuvant.

Compositions of the present invention may also be administered via a vaginal route. In such cases, a vaccine may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, a vaccine may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response (e.g., using a composition comprising a nanoemulsion adjuvant and immunogen of the present invention).

For example, in some embodiments, a composition comprising a nanoemulsion vaccine is administered to a mucosal surface of a subject in either a priming or boosting vaccination regime. Alternatively, in some embodiments, a composition comprising a nanoemulsion vaccine is administered systemically in either a priming or boosting vaccination regime. In some embodiments, a composition comprising a nanoemulsion vaccine is administered to a subject in a priming vaccination regimen via mucosal administration and a boosting regimen via systemic administration. In some embodiments, a composition comprising a nanoemulsion vaccine is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colo.; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising a nanoemulsion adjuvant and an immunogen of the present invention may be used to protect and/or treat a subject susceptible to, or suffering from, a disease by means of administering a compositions comprising a nanoemulsion adjuvant and an immunogen by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. No. 4,596,556; U.S. Pat. No. 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

In some embodiments, each dose (e.g., of a composition comprising a nanoemulsion vaccine (e.g., administered to a subject to induce an immune response)) is from 0.001 to 25% or more (e.g., 0.001-10%, 0.5-5%, 1-3%, 2%, 6%, 10%, 25% or more) by weight immunogen (e.g., (e.g., whole cancer cells (e.g., that have undergone freeze-thaw lysis and/or other type of membrane disruption), homogenized cells (e.g., cancer cells (e.g., a cancer cell line or genetically modified cancer cells), cells (e.g., cancer cells (e.g., that have been exposed to UV radiation), one or a plurality of tumor associated antigens (e.g., recombinant and/or purified protein antigens), cells modified (e.g., genetically modified) to express (e.g., over-express) one or a plurality of tumor associated antigens, one or a plurality of protein components (e.g., isolated and/or purified and/or recombinant protein) from one or a plurality of cancer cells). In some embodiments, an initial or prime administration dose contains more immunogen than a subsequent boost dose Generally, the emulsion compositions of the invention will comprise at least 0.001% to 100%, preferably 0.01 to 90%, of emulsion per ml of liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention.

EXPERIMENTAL

The following examples are provided in order to demonstrate and further illustrate certain preferred embodiments and aspects of the present invention and are not to be construed as limiting the scope thereof.

Example 1

Methods of Formulating Emulsions

The emulsion is produced as follows: an oil phase is made by blending organic solvent, oil, and surfactant and then heating the resulting mixture at 37-90° C. for up to one hour. The emulsion is formed either with a reciprocating syringe instrumentation or Silverson high sheer mixer. The water phase is added to the oil phase and mixed for 1-30 minutes, preferably for 5 minutes. For emulsions containing volatile ingredients, the volatile ingredients are added along with the aqueous phase.

In one example, the emulsion was formed as follows: an oil phase was made by blending tri-butyl phosphate, soybean oil, and a surfactant (e.g., TRITON X-100) and then heating the resulting mixture at 86° C. for one hour. An emulsion was then produced by injecting water into the oil phase at a volume/volume ratio of one part oil phase to four parts water. The emulsion can be produced manually, with reciprocating syringe instrumentation, or with batch or continuous flow instrumentation. Methods of producing these emulsions are well known to those of skill in the art and are described in e.g., U.S. Pat. Nos. 5,103,497; and 4,895,452, and U.S. Pat. Nos. 6,015,832, 6,506,803, 6,559,189, 6,635,676, and U.S. Patent Publication No. 20040043041, all of which are incorporated herein by reference in their entireties. Table 2 shows the proportions of each component, the pH, and the size of the emulsion as measured on a Coulter LS130 laser sizing instrument equipped with a circulating water bath.

TABLE 2

| Chemical Components of Emulsion | Percentage of Each Component | pH | Mean Coulter Size (in Microns) | Mean Coulter Range (in Microns) |
|---|---|---|---|---|
| X8P | | | | |
| TRITON X-100 | 2% | | | |
| Tributyl phosphate | 2% | 5.16 | 1.074 | 0.758-1.428 |
| Oil (ex. Soy bean) | 16% | | | |
| Water | 80% | | | |
| X8P 0.1 * | | | | |
| TRITON X-100 | 0.20% | | | |
| Tributyl phosphate | 0.20% | 5.37 | 0.944 | 0.625-1.333 |
| Oil (ex. Soy bean) | 1.60% | | | |
| Water | 98% | | | |

* This emulsion was obtained by diluting the X8P emulsion with water in a ratio of 1:9

The emulsions utilized in the present invention are highly stable. Indeed, emulsions were produced as described above and allowed to stand overnight at room temperature in sealed, different sizes of polypropylene tubes, beakers or flasks. The emulsions were then monitored for signs of separation. Emulsions that showed no signs of separation were considered "stable." Stable emulsions were then monitored over 1 year and were found to maintain stability.

Emulsions were again produced as described above and allowed to stand overnight at −20° C. in sealed 50 mL polypropylene tubes. The emulsions were then monitored for signs of separation. Emulsions that showed no signs of separation were considered "stable." The X8P and X8P 0.1, emulsions have been found to be substantially unchanged after storage at room temperature for at least 24 months.

Example 2

Novel Adjuvant Composition and Methods of Using the Same to Skew T-Helper-Type Immune Responses Cells (JawsII) were treated in vitro with a 0.0001% dilution of Tween 80-based nanoemulsion (NE) ($W_{80}5EC$), or poloxamer 407-based NE ($P_{407}5EC$), with either the NE alone or mixed with recombinant protective antigen of B. anthracis (rPA). Control cells were incubated with either rPA alone, or with protein kinase C (PKC) pathway activators, phorbol myristate acetate (PMA) and ionomycin (Iono). Microarray analysis of transcription activation was performed after cells were treated continuously for 6 or 24 hours. RNA was subsequently isolated, amplified, and then gene expression analyzed using a 45,000 probeset mouse GENECHIP 430.20 at the University of Michigan Comprehensive Cancer Center (UMCCC) Microarray Core Facility. The GENECHIP 430.20 MAPK pathway includes 670 probesets and the GENECHIP 430.20 TCR pathway includes 268 probesets. Experiments were conducted to determine the ability of Tween and poloxamer-based nanoemulsions (e.g., $W_{80}5EC$ and $P_{407}5EC$) to skew immune responses (e.g., towards a Th1 or Th2 immune response). Gene expression profiling in dendritic cells was utilized as a qualitative and quantitative means of determining the ability of nanoemulsion adjuvants to skew immune responses.

Microarray analysis of the full 45,000 probset revealed significantly altered gene expression subsequent to administration of PMA/Iono (See FIG. 1). 1346 genes exhibited increases and 766 genes exhibited decreases after 6 hours. Administration of $W_{80}5EC$, with or without rPA, also resulted in large changes in gene expression. 898 genes exhibited increases and 514 genes exhibiting decreases after 6 hours. Administration of $P_{407}5EC$, with or without rPA, also altered gene expression, with 18 genes displaying enhanced expression and 116 displaying reduced expression after 6 hours of exposure to the nanoemulsion. Longer exposure periods resulted in an increase in the number of genes with alteration in expression (See FIG. 1).

Example 3

NE Adjuvant Alters Gene Expression

Analysis of gene transcription patterns demonstrated that $W_{80}5EC$ has a unique effect on gene expression in dendritic cells. $W_{80}$5EC-induced changes in JawsII transcription are not dependent on presence of antigenic rPA protein and are in stark contrast to the minimal effect of $P_{407}$5EC NE (See FIG. 1). Analysis of specific signaling pathways including mitogen activated protein kinase (MAPK), T-cell receptor (TCR), B-cell receptor, Toll-like receptors, apoptosis and others, indicate unique patterns of gene expression in cells, subsequent to administration of the NE to the cells. A significant increase in the protein kinase and MAPK associated gene transcripts was identified in all analyzed pathways.

Genes associated with the MAPK pathway displayed altered expression levels subsequent to administration of $W_{80}$5EC NE (See FIG. 2). A large number of alterations in gene expression were observed for the $W_{80}$5EC NE-treated cells, whereas fewer numbers of genes displaying altered expression was observed for the $P_{407}$5EC NE- or rPA-treated cells. Altered gene expression was observed at both 6 and 24 hours.

TCR pathway associated genes also exhibited significantly altered expression upon treatment with $W_{80}$5EC NE, whereas little or no effect was observed for the $P_{40}$75EC NE- or rPA-treated cells (FIG. 3). Altered TCR pathway associated gene expression was observed at both 6 and 24 hours.

An increase in the expression of dendritic cell maturation markers DC83 and CD86 was observed post-administration of NE (FIG. 4). There was no significant activation of Toll-like receptor transcription, or expression of hallmark inflammatory cytokines (e.g. INF-γ, TNF-α. IL-12 IL-4, IL-5, IL-13), under the experimental conditions tested.

Example 4

Novel Adjuvant Composition and Methods of Using the Same to Re-Direct Th2-Polarized Immune Responses Experiments were conducted to determine if Th1- and/or Th2-type immune response could be redirected (e.g., towards Th2-type or Th-1 type immune responses, respectively) by administration of an NE adjuvant. In order to elicit a Th2 immune response, mice (CD-1) were immunized intramuscularly with alum-adsorbed Hepatitis B virus surface antigen (HBsAg). Analysis of serum IgG subclass and cytokine expression confirmed prevalence of IgG1 subclass antibodies and Th2 pattern of cytokine expression, thus demonstrating that the mice had an established Th2-type immune response. The mice were then administered a single, intranasal immunization of nanoemulsion adjuvant (independently or with an immunogenic protein (e.g., HBsAg or rPA). Titers of IgG2a and IgG2b subclass antibodies rose in mice after NE nasal immunization, and their splenic lymphocytes produced IFN-γ, a Th1-type cytokine. Production of Th1-type cytokines demonstrated redirection of the established Th2-type immune response towards a Th1-type immune response. No local inflammatory response was observed in the nares of NE exposed animals, and no local production of IL-12 or other Th1-associated cytokines were observed. Thus, the present invention provides the ability to redirect Th2-polarized immune responses in a subject toward a Th1-type immune response via exposing the subject to (e.g., nasally administering) a NE adjuvant (e.g., in the presence or absence of other components (e.g., immunogenic antigens and/or polypeptides). In cases where NE adjuvant was administered with antigens (e.g., HBsAg), antigen was found throughout the immune system within 24 hours after nasal administration. Thus, in some embodiments, the present invention provides that dendritic cells engage (e.g., engulf) nanoemulsion and/or antigens present therein.

Example 5

Nanoemulsion Adjuvant Charge Alters Antigen Immunogenicity

Experiments were conducted to characterize nanoemulsion adjuvant components. Mice were vaccinated with three variant (e.g., that possess variant physical characteristics) antigens, ovalbumin (OVA, a main protein found in egg white), bovine serum albumin (BSA), and lysozyme. Each antigen was formulated separately in each of the following nanoemulsions: W805EC, W805E or P4075EC. Dilutions (1:200, 1:500 and 1:1000 dilutions) of each formulation were administered intranasally (IN) to mice. Antigens suspended in phosphate buffered saline (PBS) and administered intranasally (IN) or subcutaneously (SC) were utilized as controls. Mice were bled nine weeks post administration. Serum IgG was monitored using ELISA. The optical density (indicative of serum IgG concentration) was measured (See FIGS. 6-8).

Vaccines formulations containing W805E (lacking the cationic compound CPC) had a negative surface potential, while vaccine formulations with the cationic compound CPC (W805EC and P4075EC) had a positive surface potential. Formulations comprising W805E produced an immune response that was not above the level observed for control animals intranasally administered the antigen in Phosphate Buffered Saline (See FIGS. 6-8). Formulations comprising a positively charged nanoemulsion (e.g., comprising the cationic compound CPC) produced robust immune responses that were many times the level of the control animals (See FIGS. 6-8). Thus, the present invention provides that positively charged nanoemusion adjuvants (e.g., comprising a positive surface charge (e.g., due to the presence of a cationic compound (e.g., CPC))) possess greater efficacy at eliciting immune responses than nanoemulsion adjuvants lacking a positive charge (e.g., lacking a positive surface charge (e.g., due to the absence of a cationic compound (e.g., CPC))). Although an understanding of a mechanism is not necessary to practice the present invention, and the present invention is not limited to any particular mechanism of action, in some embodiments, a nanoemulsion adjuvant possessing a positive charge (e.g., a positive surface charge (e.g., due to the presence of a cationic compound in the nanoemulsion (e.g., CPC))) possesses greater adhesion to mucosa than non-positively charged emulsions (e.g., due to the positively charged surface of the emulsion). In some embodiments, a nanoemulsion adjuvant possessing a positive charge (e.g., a positive surface charge (e.g., due to the presence of a cationic compound in the nanoemulsion (e.g., CPC))) is more readily internalized by phagocytic cells (e.g., macrophages, dendritic cells, B cells, etc.) than is a non-positively charged nanoemulsion (e.g., leading to greater internalization of antigen (e.g., by antigen presenting cells), processing of antigen, and/or presentation of antigen to B and/or T cells). Thus, in some embodiments, greater internalization and/or processing of antigen, and/or presentation of antigen to B and/or T cells leads to a stronger, more robust immune response (e.g., to an antigen administered in a nanoemulsion possessing a positive charge (e.g., a positive surface charge (e.g., due to the presence of a cationic compound in the nanoemulsion (e.g., CPC))).

Example 6

Nanoemulsion Adjuvants Stimulate and/or Elicit Host Innate Immune Responses

Figure 9:
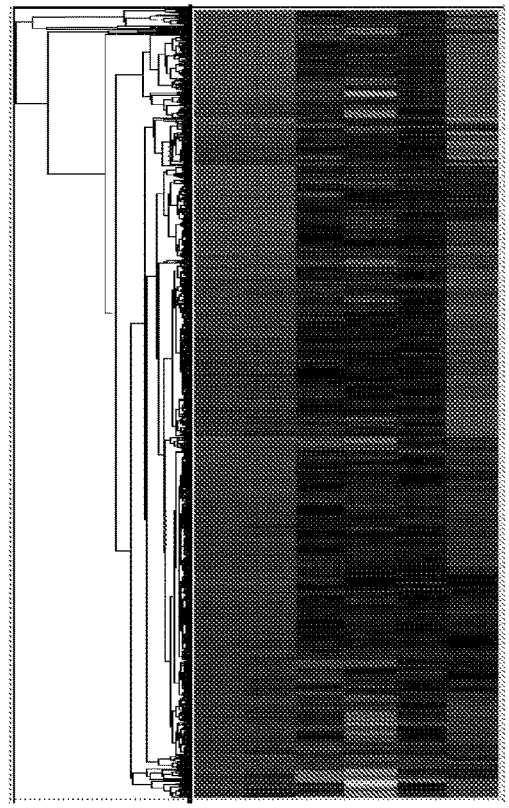
FIG. 9 shows microarray analysis (hierarchical clustering) of changes in gene expression in (A) JAWS II dendritic cells and (B) bone marrow derived dendritic cells (BMDC) administered W805EC, P4075EC or PMA/ionomycin.
Figure 9:
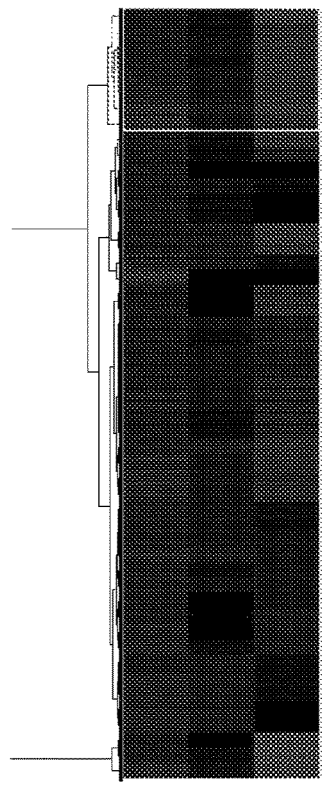

Dendritic cells (JAWS II) and bone marrow derived dendritic cells (BMDC) were administered W805EC, P4075EC or PMA/ionomycin and alteration in gene expression analyzed. FIG. 9 shows microarray analysis (hierarchical clustering) of changes in gene expression in (A) JAWS II dendritic cells and (B) bone marrow derived dendritic cells (BMDC). Thus, in some embodiments, nanoemulsion adjuvants (e.g., in the absence of immunogen) possess the ability to induce changes in cells administered the adjuvant (e.g., to alter gene expression in antigen presenting cells of the host). Experiments were conducted to further characterize the ability of nanoemulsion adjuvants provided herein to induce immune responses in host subjects.

Figure 10:
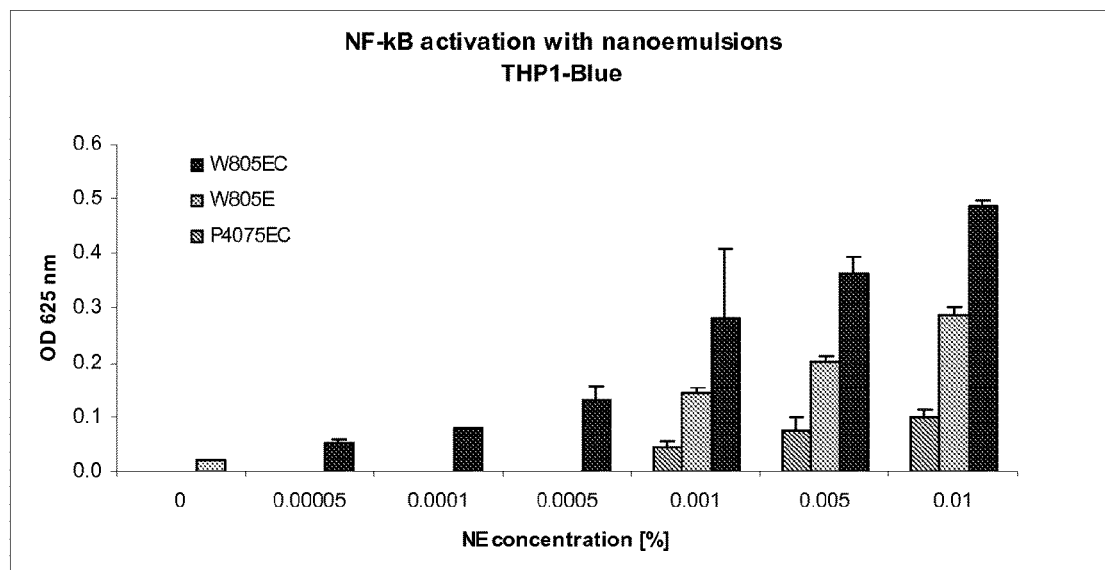
FIG. 10 shows that nanoemulsion adjuvant possesses ligand activity for toll-like receptors (TLRs) and activates NF-kB.

Nanoemulsion adjuvants were administered to human monocyte cells (THP1-Blue) over a range of different concentrations and the activity of NF-kB monitored. Nanoemulsion adjuvants comprising a polysorbate detergent (e.g., TWEEN-80) activated NF-kB in the cells, whereas nanoemulsion adjuvants lacking a polysorbate detergent were unable to activate NF-kB at low concentrations, and were displayed significantly reduced ability to activate NF-kB at higher concentrations compared to nanoemulsion adjuvants comprising a polysorbate detergent (See FIG. 10).

Figure 11:
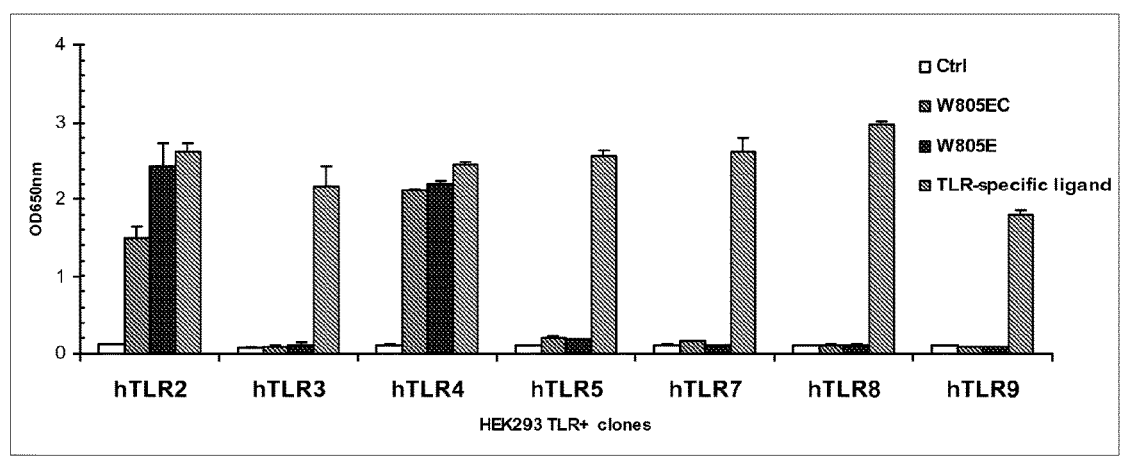
FIG. 11 shows NF-kB activation in human HEK293 clones engineered to express specific TLRs.

Experiments were conducted to determine if the bioactivity of the nanoemulsion adjuvants (e.g., as measured by the activation of transcriptional factor NF-κB) occurred through the activation of Toll-like receptors (TLRs). NF-κB activation was measured in human HEK293 clones engineered to express a single specific TLR (See FIG. 11). As shown in FIG. 11, nanoemulsion adjuvants comprising a polysorbate detergent display that ability to induce signaling via Toll-like receptor 2 and 4 (TLR2 and TLR4). Although an understanding of a mechanism is not necessary to practice the present invention, and the present invention is not limited to any particular mechanism of action, in some embodiments, nanoemulsion adjuvants provided herein activate NF-κB response by stimulation of TLRs (e.g., TLR2 and TLR4). Thus, in some embodiments, the present invention provides nanoemulsion adjuvants (e.g., possessing a positive charge (e.g., a positive surface charge (e.g., due to the presence of a cationic compound in the nanoemulsion (e.g., CPC))) that are utilized to increase mucosal adhesion and internalization (e.g., by dendritic cells) and/or that are utilized to induce innate immune responses (e.g., TLR signaling, activation of NF-kB and expression of cytokines) in a host subject.

Example 7

Intranasally Administered NE Facilitates Trafficking to Immunological Sites

Figure 12:
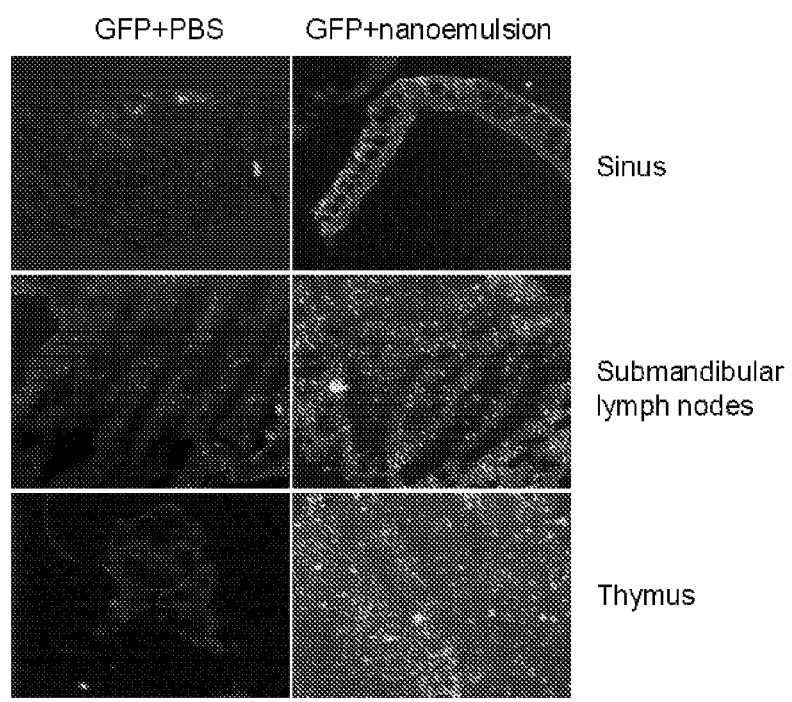
FIG. 12 shows that nasally administered NE can traffic material to the sinus, lymph nodes and thymus.

In order to determine whether NE could be utilized to traffic materials (e.g., cancer antigens) to immunologic sites, mice were intranasally administered with either NE mixed with green fluorescent protein (GFP), or phosphate buffered saline (PBS) mixed with GFP. Twenty-four hours post administration, mice were sacrificed and the sinus, the submandibular lymph nodes, and the thymus were examined for the presence of GFP. The NE facilitated trafficking of GFP to each of these sites (See, e.g., FIG. 12). Thus, in some embodiments, the present invention provides that NE can be utilized to deliver material mixed with the NE (e.g., antigens, cells, lysates, etc.) to immunologic sites (e.g., the sinus, lymph nodes, and/or thymus).

Example 8

Nanoemulsion Cancer Vaccine

Figure 13:
FIG. 13 shows a picture of a healthy lung and a lung with MC-38 metastases harvested from mice.
Figure 13:
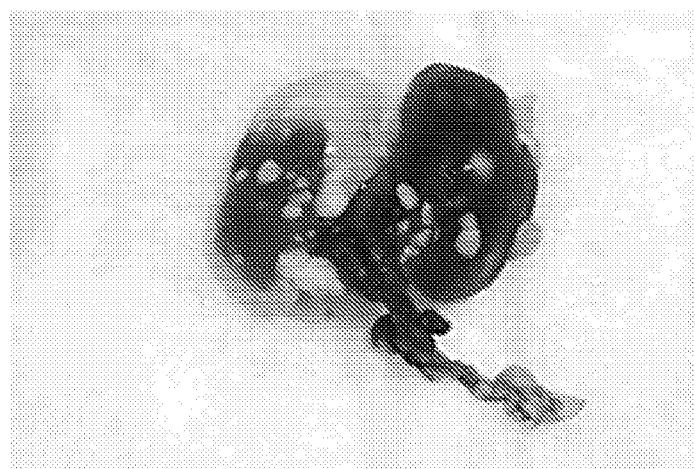

Experiments were conducted during development of embodiments of the invention in order to determine whether a nanoemulsion (NE) cancer vaccine could be utilized to alter a subject's immune response (e.g., to induce an immune response (e.g., against cancer (e.g., a tumor (e.g., one or more tumor associated antigens))) and/or to inhibit induction of an immune response (e.g., tumor-related immune tolerance (e.g., resulting from generation of T regulatory cells)). Female C57BL/B6 mice were immunized on day 0 and day 14 with MC-38 whole cell lysate mixed with NE. Briefly, MC-38 cells were grown to logarithmic phase, spun to pellet, washed in phosphate buffered saline, and spun to pellet. The cell pellet was placed at −20° C. and allowed to freeze, removed and placed at room temperature and allowed to thaw, and frozen again. The freeze-thaw cycle was repeated several times. The cells, post freeze-thaw cycling, were mixed (vol/vol) with 60% W805EC to obtain a NE cancer vaccine with a final NE concentration of 30%. The NE cancer vaccine was utilized for nasal administration (e.g., vaccination) in mice. The final concentration of ingredients in a 10 µl volume of vaccine was 25,000 MC-38 freeze-thawed cells in PBS (5 µl) mixed with 60% W805EC (5 µl). Control mice received PBS, NE+PBS or MC-38 freeze-thawed cells+PBS. On day 35, animals were injected intravenously with $2\times10^5$ MC-38 cells in 200 µL PBS per animal. On day 62, the animals were sacrificed and the numbers of lung metastases were counted. Examples of a healthy lung and a lung with MC-38 metastases are shown in FIG. 13.

Figure 14:
FIG. 14 shows inhibition of lung metastases in subjects immunized with NE+Ag.
Figure 14:
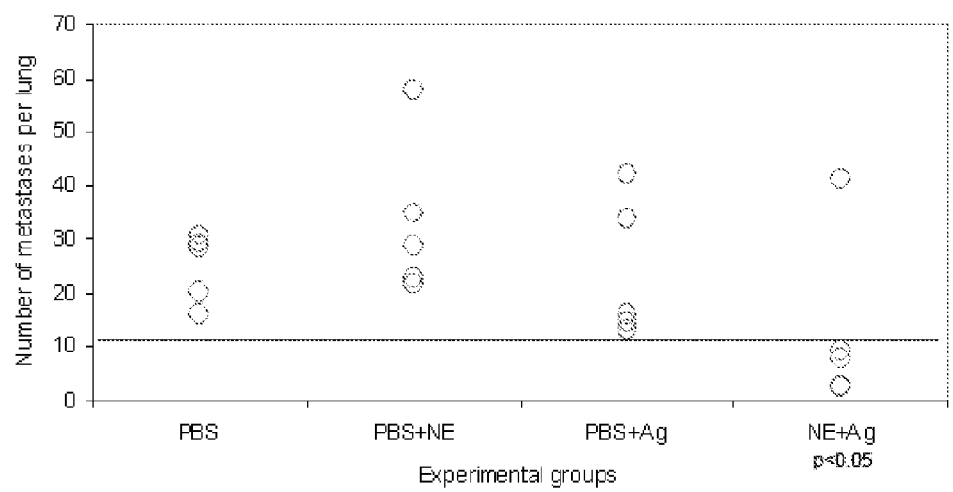

For assessment of metastases, the lung and trachea of each subject were transected, injected with India ink, and excised en bloc. Subsequently, the specimens are placed in Fekete solution for 24 hours to bleach tumor metastases in the lungs and visualize white pulmonary metastases. Significant inhibition ($p<0.05$) of metastases was observed in subjects immunized with the NE+freeze-thawed MC-38 cells compared with control groups (See, e.g., FIG. 14).

Figure 15:
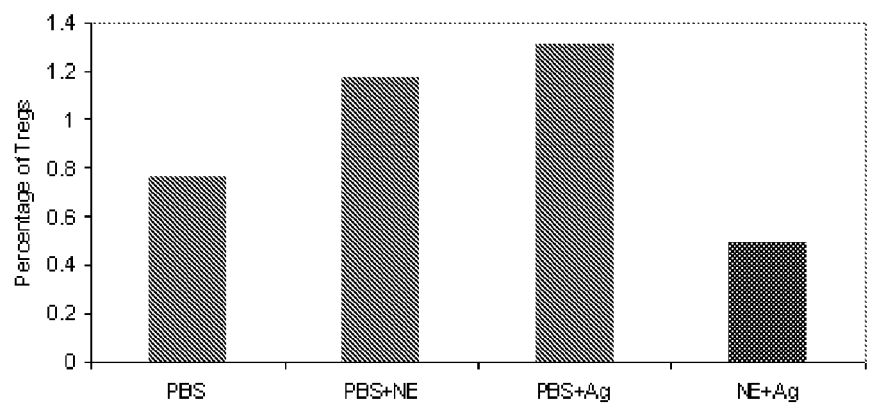
FIG. 15 shows flow cytometric analysis of Foxp3$^+$ T$_{regs}$ in mediastinal lymph nodes leucocytes (A) and CD4$^+$ lymphocyte population (B) in subjects immunized with NE+Ag.
Figure 15:
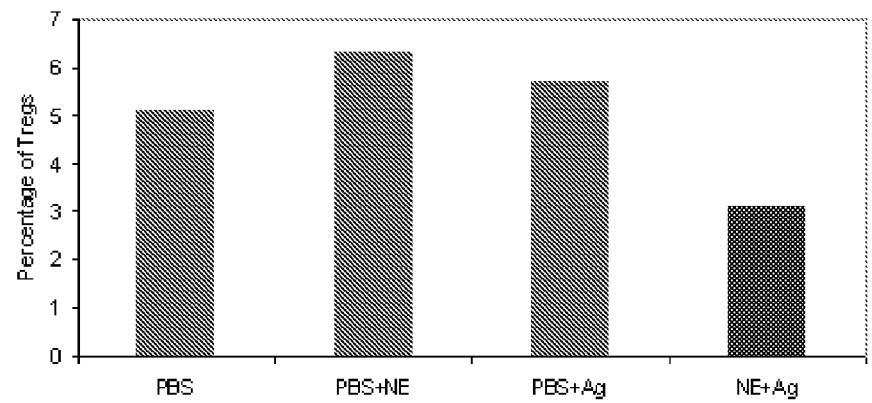

Experiments were also conducted to determine the number of $T_{regs}$ cells in the mediastinal lymph nodes of the subjects. Subjects were humanely euthanized and mediastinal lymph nodes removed. Cells (leukocytes) from mediastinal lymph nodes were isolated and pooled per experimental group. The cells were stained with anti-Foxp3 antibody (a cell marker of T regulatory cells). To further dissect the percentage of T regulatory cells in CD4 cell population, cells were stained with two antibodies: one anti-Foxp3 antibody and anti-CD4 antibody (a marker of T helper lymphocytes). In this way, the percentage of T regulatory cells was assessed exclusively in T helper cell population. The percentage of T regulatory cells (Foxp3 positive) was compared to number of all leukocytes (100%) as well as to the number of CD4 positive cells (100%). Remarkably, animals immunized with the NE-cancer vaccine (e.g., NE+freeze-thawed MC-38 cells) had, on average, the lowest number of $T_{regs}$ cells both in the leucocyte and in the CD4+ lymphocyte populations (See, e.g., FIG. 15). Thus, in some embodiments, the present invention provides NE cancer vaccine compositions and methods of using the same to inhibit and/or reduce tumor metastasis and/or cancer growth. In some embodiments, the present invention provides compositions (e.g., NE cancer vaccines) and methods using the same to induce anti-cancer and/or anti-tumor immune responses (e.g., against one or more tumor associated antigens (e.g., to vaccinate (e.g., prophylactically and/or therapeutically))) in a subject while concurrently suppressing development of T regulatory cells in the subject. Thus, in some embodiments, the present invention provides compositions and methods for avoiding immune tolerance (e.g., tumor-related immune tolerance).

Example 9

Nanoemulsion-Based Vaccine Against Cancer in Multiple Animal Models

Additional experiments were carried out to further characterize immune responses generated using compositions and methods of the invention. Two separate animal models were utilized. MC-38 murine colon tumor, grade III adenocarcinoma (See, e.g., Corbett et al., Cancer Res 1975, 35(9):2434-2439) and B16 F10 melanoma cells transfected with ovalbumin (See e.g., Falo et al., Nat Med 1995, 1(7):649-653); both cell lines grow and produce solid tumors and metastases when implanted into syngeneic C57BL/B6 mice (See, e.g., Tanigawa et al., J Immunother (1997) 2000, 23(5):528-535 and Kawano et al., J Immunol 1986, 136(12):4729-4734). The B6 animals were intranasally vaccinated with PBS, PBS+MC38 cell lysate, nanoemulsion (NE)+MC38 cell lysate, or NE+PBS. MC38 cell lysate was generated according to methods described in Example 8. Two weeks after the last vaccination all mice were injected IV with MC38 cells to induce pulmonary metastasis. Six weeks later mice were sacrificed, lungs excised and the number of metastases was counted. Cells from mediastinal nodes were isolated and stained with a set of surface and intracellular antibodies to define relative numbers of immuno-competent cells involved in the response to the tumor challenge.

In the second animal model, using B16 OVA cells, experiments were designed and performed as follows. The B6 mice were intranasally vaccinated with PBS, PBS+ovalbumin, NE+ovalbumin, or cholera toxin (CT)+ovalbumin. One week after the last vaccination all mice were injected with $10^5$ B16 OVA cells under the scapula to induce the growth of solid tumor. Mice were monitored for 50 days for tumor growth. Cells from draining nodes were isolated and stained with a set of surface and intracellular antibodies to define relative numbers of immuno-competent cells involved in the response to the tumor challenge. Sera from experimental animals were tested for specific anti-ovalbumin antibody production.

The B6 animals were intranasally (10 L volume/animal/vaccination) vaccinated with PBS, PBS+MC38 cell lysate (prepared from $2.5 \times 10^4$ cells/animal/vaccination), 20% $W_{80}5EC$+MC38 cell lysate, or $W_{80}5EC$+PBS. The MC38 cell lysate was produced by the freezing and thawing procedure described in Example 8 Animals were vaccinated two times, three weeks apart. Two weeks after the last vaccination all mice were challenged IV with $2 \times 10^5$ MC38 cells in 200 1 PBS to induce pulmonary metastasis. Six weeks later mice were sacrificed, lungs excised and stained with India ink, and the number of metastases counted. Cells from mediastinal nodes were isolated and stained with the following anti-mouse antibodies: anti-CD4, -CD8, -FoxP3, and IFN—to define the relative numbers of immuno-competent cells involved in the response to the tumor challenge.

Experiments were also designed and performed using another tumor model. The B6 mice were intranasally vaccinated with PBS, PBS+ovalbumin (20 g/animal/vaccination), 20% $W_{80}5EC$+ovalbumin, or cholera toxin (1 g/animal/vaccination)+ovalbumin four times, two weeks apart. One week after the last vaccination mice were injected with $10^5$ B16 OVA cells in 100 1 HBSS under the scapula. The mice were monitored two times a week for 50 days for tumor growth Animals with a tumor size no larger than 21 mm in diameter were humanely sacrificed. Cells from draining nodes were isolated and stained with the following anti-mouse antibodies: anti-GR-1, -CD11b, -CD11c, -CD45, -CD90, -CD8a, -IFN-, -IL-17, -IL-2.-FoxP3 to define the relative numbers of immuno-competent cells involved in response to the tumor challenge. Sera from experimental animals were tested for specific anti-ovalbumin antibody production and the IgG2c subclass of antibody was determined.

Figure 16:
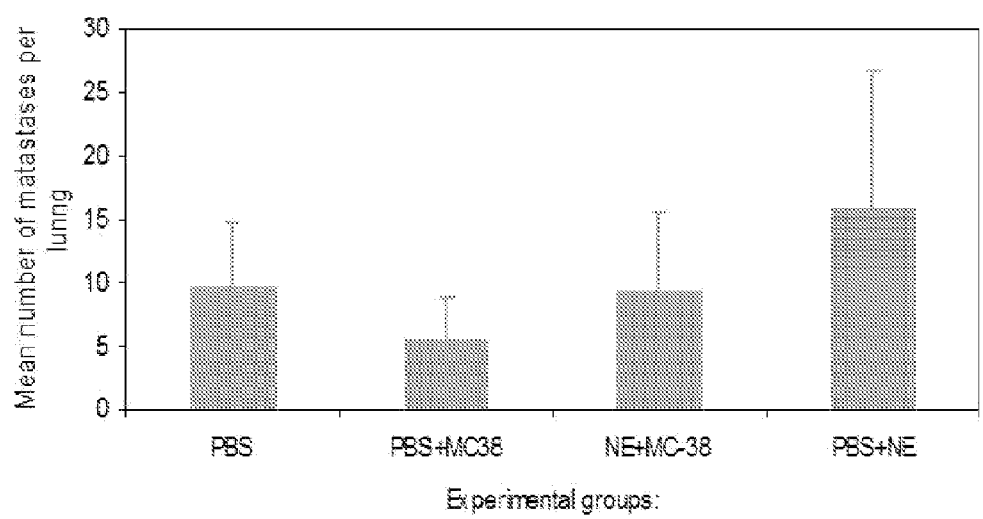
FIG. 16 shows the mean number of metastases in B6 mice vaccinated with MC38 cell lysate and challenged IV with MC38 cells.

B6 mice intranasally vaccinated with MC38 cell lysate as described above were challenged IV with MC38 cells to induce pulmonary metastasis. Specifically, B6 mice were intranasally vaccinated with PBS, PBS+MC38 cell lysate, 20% $W_{80}5EC$+MC38 cell lysate, or 20% $W_{80}5EC$+PBS two times, three weeks apart. Two weeks after the last vaccination all mice were injected IV with $2 \times 10^5$ MC38 cells in 200 1 PBS. Six weeks later the mice were sacrificed, lungs were excised and stained with India ink, and the number of metastases counted. FIG. 16 shows the number of metastases found in each experimental group of animals.

Figure 17:
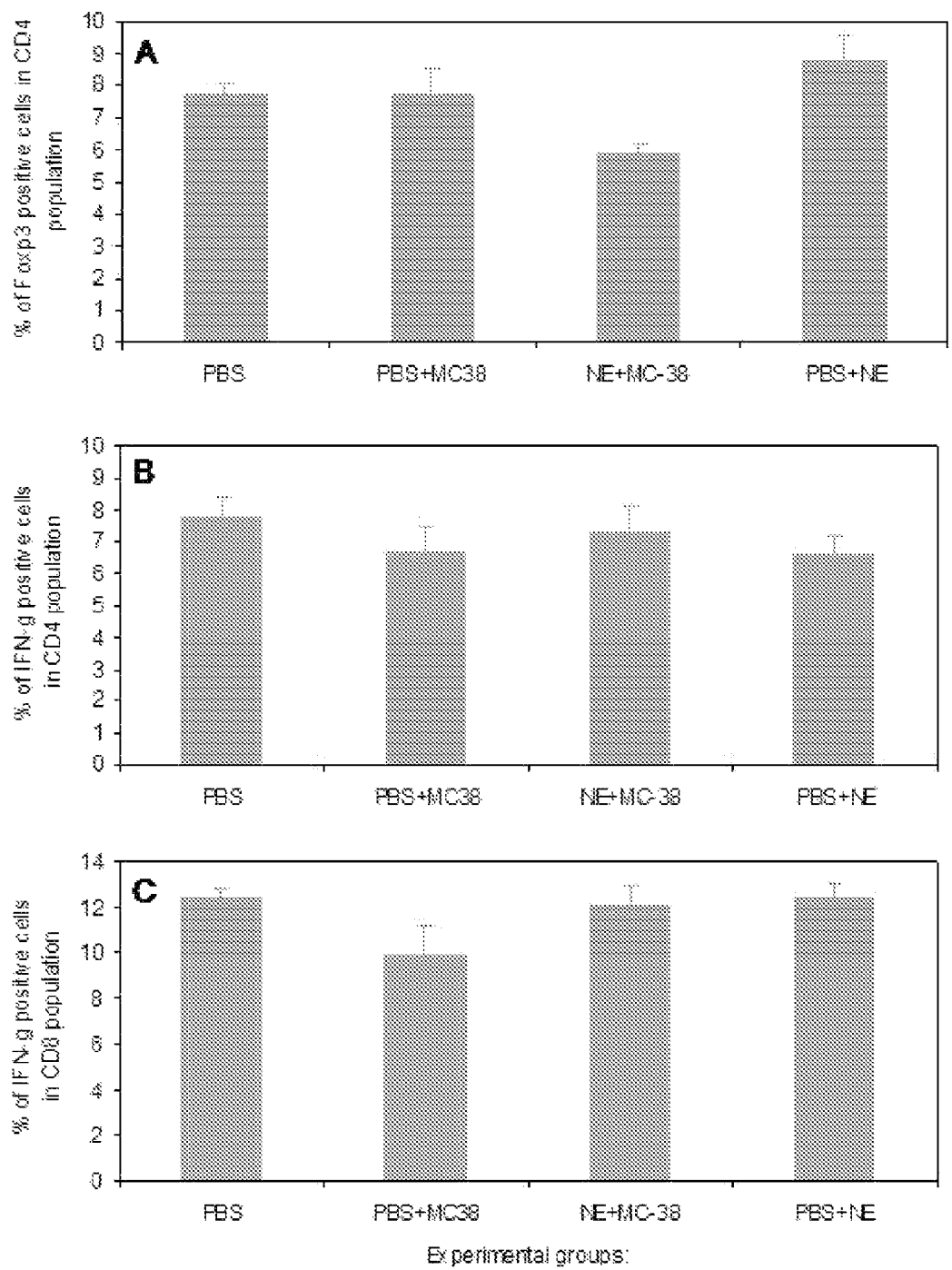
FIG. 17 shows the percentage of FoxP3 (A) and IFN-γ (B) positive cells in CD4 population and (C) percentage of IFN-γ positive cells in CD8 population.

The highest number of metastases was found in animals vaccinated with $W_{80}5EC$+PBS (average number of metastasis 16). In the experimental group vaccinated with $W_{80}5EC$+MC38 cell lysate the average number of metastases was 9.5. In order to examine the relative numbers of immuno-competent cells from all experimental groups, mediastinal nodes were harvested and cells isolated and stained with anti-CD4, -CD8, -FoxP3, and -IFN-antibodies. The percentage of CD4 or CD8 cells producing IFN—is shown in FIG. 17. The range of CD4/IFN- and CD8/IFN-double positive cells across all experimental groups was 6.7-7.8 and 10-12.5%, respectively. A slight decrease was observed in the percentage of FoxP3/CD4 double positive cells in the experimental group immunized with NE+MC38 cell lysate (See FIG. 17A).

Figure 18:
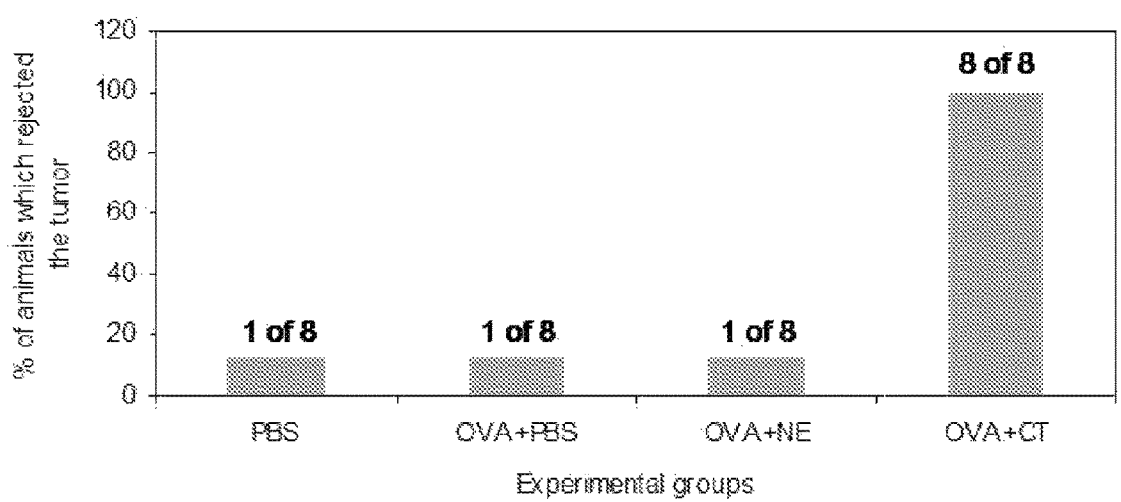
FIG. 18 shows rejection of tumor by animals immunized with ovalbumin prior to the challenge (50 day survival without signs of tumor).
Figure 19:
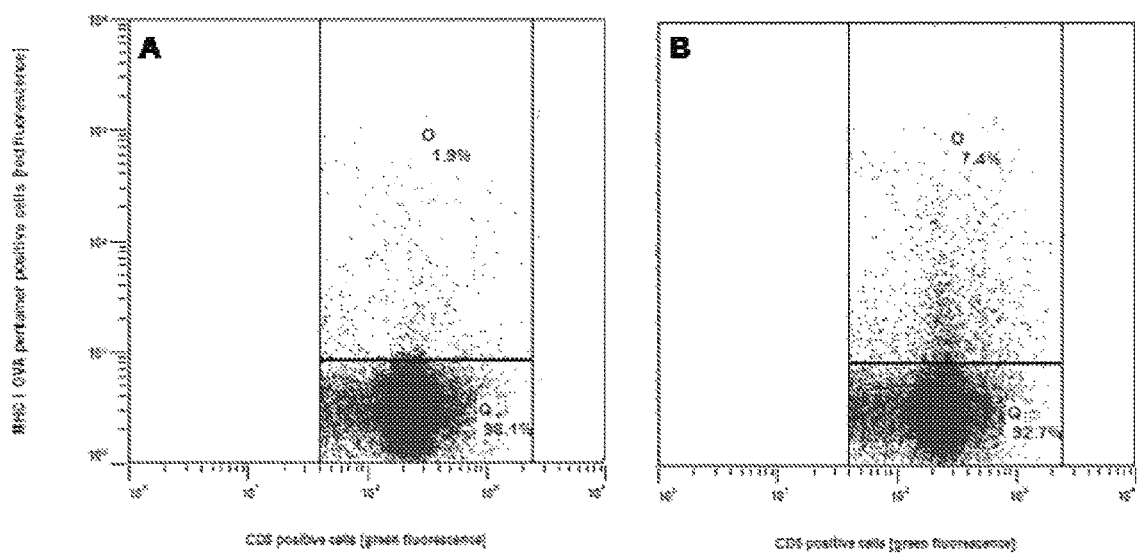
FIG. 19 shows draining lymph nodes cells stained with CD8 antibodies and MHC I OVA pentamer.

The B16 OVA tumor model was utilized to study the development of protective immunity against a challenge with B16 OVA cells after intranasal vaccination with ovalbumin. B6 mice were intranasally vaccinated with PBS, PBS+ovalbumin (20 g/animal/vaccination), 20% W$_{80}$5EC+ ovalbumin, or cholera toxin (CT) (1 g/animal/vaccination)+ ovalbumin four times, two weeks apart. One week after the last vaccination all mice were injected with $10^5$ B16 OVA cells in 100 l HBSS under the scapula. Mice were monitored two times a week for 50 days for tumor growth. Animals with tumor size approximately 20 mm in diameter were humanely sacrificed. The challenge data are presented in FIG. 18. Animals from the experimental group vaccinated with ovalbumin and CT did not develop tumors and through the end of the experiment (50 days after challenge) did not show any signs of disease whereas more than 80% of animals from all other groups developed tumors within 30 days. To assess the number of CD8 anti-ovalbumin specific cells in experimental animals cells from draining lymph nodes were isolated and stained simultaneously with MHC I OVA-PE pentamer (which binds to CD8 positive cells) and CD8a-FITC antibody (See FIG. 19). The percentage of MHC I OVA-PE pentamer positive cells out of CD8 positive cells is shown in Table 3 below.

TABLE 3

Percentage of double CD8 and MHC I OVA pentamer cells in draining lymph nodes.

| Experimental groups | N = | Percentage of CD8/ Pent. positive cells | SD |
|---|---|---|---|
| Naïve/no challenged | 3 | 2.7 | 0.6 |
| Naïve/challenged | 3 | 2.6 | 0.8 |
| OVA + NE/vaccinated/challenged | 3 | 6.1 | 1.9 |
| OVA + CT/vaccinated/challenged | 3 | 2.4 | 0.4 |
| OVA + PBS/vaccinated/challenged | 3 | 3.0 | 1.2 |

Figure 20:
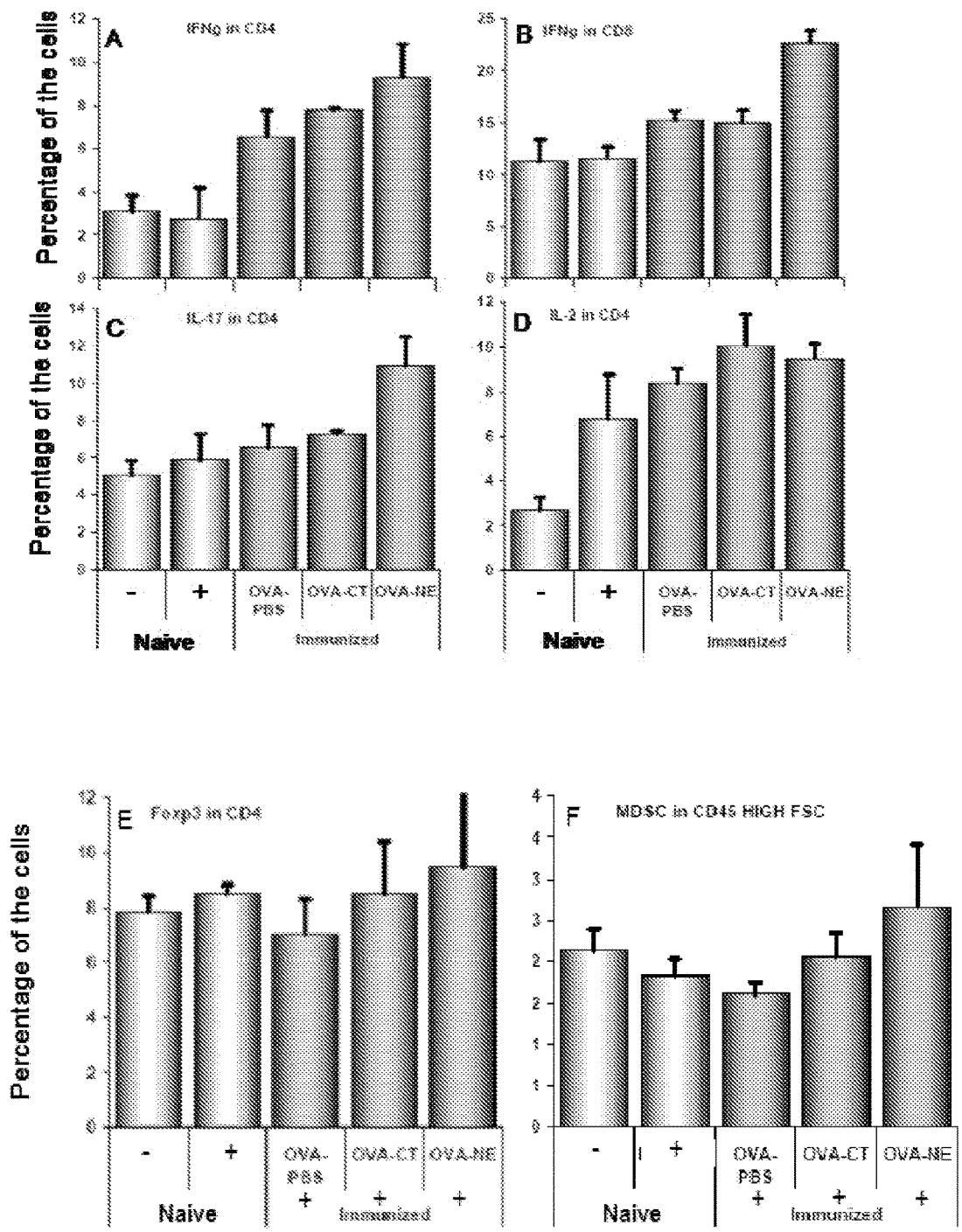
FIG. 20 shows the percentages of different subsets of cells isolated from draining lymph nodes.
Figure 21:
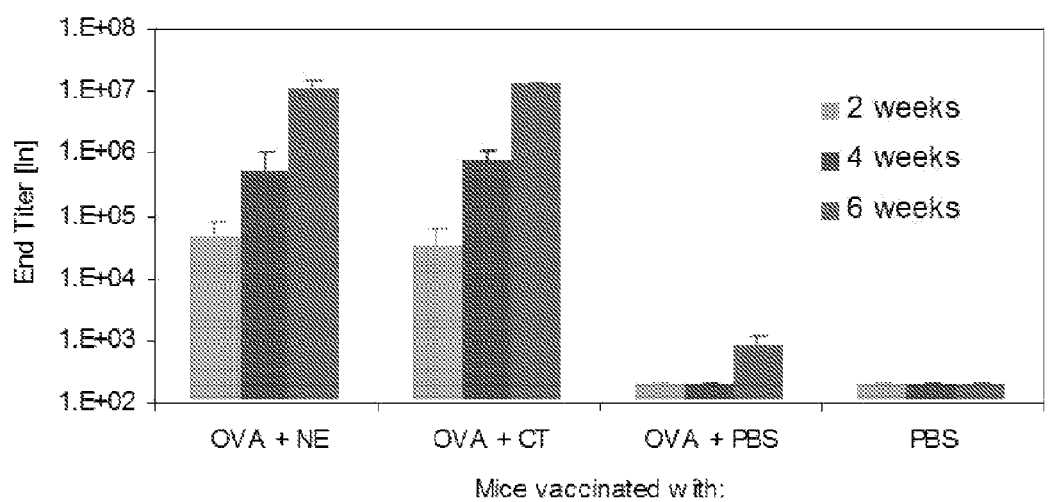
FIG. 21 shows the end titer of ovalbumin specific IgG in sera from vaccinated mice.
Figure 22:
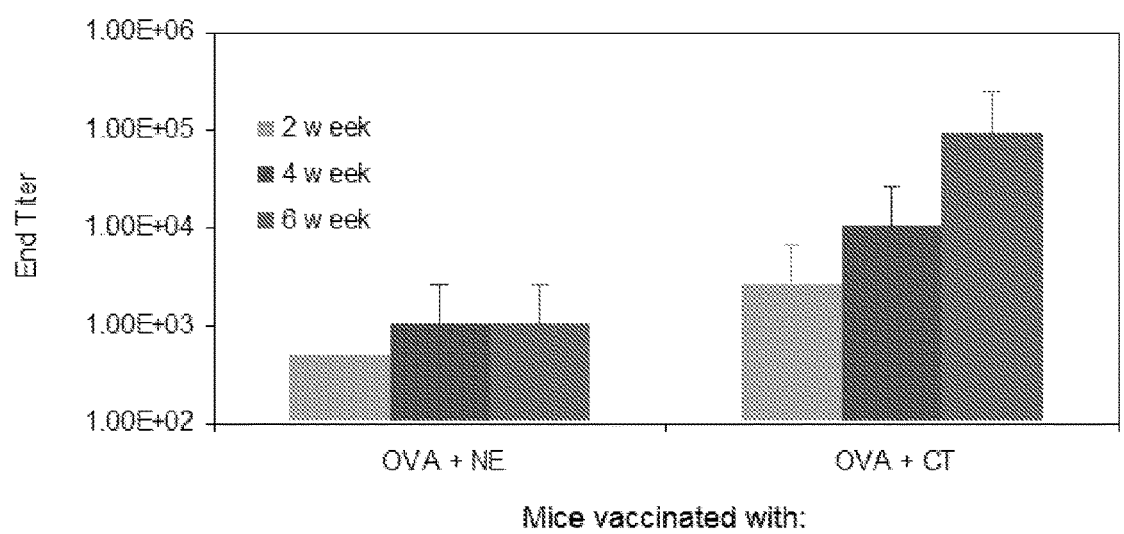
FIG. 22 shows the end titer of ovalbumin specific IgG2c in sera from vaccinated mice.

There was an increase in percentage of CD8$^+$/pentamer$^+$ in the experimental group of mice vaccinated with NE+OVA and challenged with B16 OVA as compared to other experimental groups. The percentage of different subsets of immuno-competent cells obtained from nave and vaccinated animals after a two week challenge with B16 OVA cells was also analyzed. FIG. 20 represents data obtained from this experiment. An increase in the percentage of both CD4 and CD8 cells which produced IFN—along with an increased percentage of CD4 cells which were IL-17 positive in the group of animals vaccinated with NE+ovalbumin was observed. The percentage of myeloid derived suppressor cells (MDSC) was to some extent elevated in the group vaccinated with NE+ovalbumin. Further, the titer of specific antibodies in the sera of experimental animals was measured. The IgG-all specific response to ovalbumin as well as the IgG2c subclass specific response was characterized. As shown in FIG. 21, NE+ovalbumin and CT+ovalbumin induced a similar quantity of specific IgG-all antibodies. A considerable difference in the quantity of specific IgG2c subclass antibodies between these two groups (FIG. 22) was also observed. The group of animals vaccinated with CT+ovalbumin developed more IgG2c subclass antibodies than mice vaccinated with NE+ovalbumin as measured by end titer using ELISA. The implication of IgG2c specific antibodies in the resistance to tumor challenge has been reported before by Lambert et al (See, e.g., Lambert et al., J Immunol 2004, 172(2):929-936).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. An immunogenic composition for stimulating a cancer specific immune response comprising:
    a) a nanoemulsion, wherein the nanoemulsion comprises oil, water, an organic solvent, a non-ionic surfactant, and a cationic surfactant; and
    b) a cancer immunogen comprising cancer cells that have undergone membrane disruption.

2. The immunogenic composition of claim 1, wherein said cancer cells that have undergone membrane disruption are selected from the group consisting of cancer cells that have undergone freeze-thaw lysis and cancer cells that have been exposed to UV radiation.

3. The immunogenic composition of claim 1, wherein the nanoemulsion comprises an organic solvent selected from ethanol, glycerol or a combination thereof; a cationic surfactant selected from cetylpyridinium chloride (CPC), benzalkonium chloride or a combination thereof; and a non-ionic surfactant selected from Poloxamer 407, polysorbate 80, or polysorbate 20.

4. The immunogenic composition of claim 1, wherein the nanoemulsion comprises:
    a) about 10% to about 80% oil;
    b) about 1% to about 50% organic solvent;
    c) about 0.1% to about 10% non-ionic surfactant; and
    d) about 0.01% to about 3% cationic surfactant.

5. The immunogenic composition of claim 1, wherein the nanoemulsion comprises:
    a) water;
    b) ethanol;
    c) cetylpyridinium chloride;
    d) polysorbate 80 or polysorbate 20; and
    e) soybean oil.

6. The immunogenic composition of claim 1, wherein the nanoemulsion further comprises a chelating agent.

7. The immunogenic composition of claim 6, wherein the nanoemulsion comprises about 0.0005% to about 1.0% of the chelating agent.

8. The immunogenic composition of claim 6, wherein the chelating agent is ethylenediaminetetraacetic acid (EDTA).

9. A method of using the immunogenic composition of claim 1 to induce a cancer-specific immune response in a subject comprising mucosally administering an effective amount of the immunogenic composition to the subject to produce a cancer specific immune response.

10. The method of claim 9, wherein the immunogenic composition is administered to the subject after surgical removal of cancer in the subject.

* * * * *